US011939619B2

(12) United States Patent
Miller et al.

(10) Patent No.: US 11,939,619 B2
(45) **Date of Patent: *Mar. 26, 2024**

(54) GLUCOAMYLASE ENGINEERED YEAST AND FERMENTATION METHODS

(71) Applicant: CARGILL, INCORPORATED, Wayzata, MN (US)

(72) Inventors: Chris Miller, Andover, MN (US); Brian Rush, Minneapolis, MN (US); Joshua Dunn, Boston, MA (US); Brynne Stanton, Boston, MA (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/657,241

(22) Filed: Mar. 30, 2022

(65) Prior Publication Data

US 2022/0228175 A1 Jul. 21, 2022

Related U.S. Application Data

(63) Continuation of application No. 16/976,550, filed as application No. PCT/US2019/019805 on Feb. 27, 2019, now Pat. No. 11,306,330.

(60) Provisional application No. 62/636,716, filed on Feb. 28, 2018.

(51) Int. Cl.

| | |
|---|---|
| ***C12P 7/10*** | (2006.01) |
| ***C12N 1/18*** | (2006.01) |
| ***C12N 9/34*** | (2006.01) |
| ***C12R 1/865*** | (2006.01) |

(52) U.S. Cl.

CPC .............. *C12P 7/10* (2013.01); *C12N 9/2428* (2013.01); *C12N 1/185* (2021.05); *C12P 2203/00* (2013.01); *C12R 2001/865* (2021.05); *C12Y 302/01003* (2013.01)

(58) Field of Classification Search

CPC ........ C12P 7/10; C12P 2203/00; C12N 9/248; C12N 1/185; C12R 2001/865; C12Y 302/01003; Y02E 50/10

See application file for complete search history.

(56) References Cited

U.S. PATENT DOCUMENTS

| | | | | |
|---|---|---|---|---|
| 8,592,194 | B2 | 11/2013 | Aehle | |
| 8,809,023 | B2 | 8/2014 | Degn | |
| 10,364,421 | B2 | 7/2019 | Miller | |
| 11,041,218 | B2 * | 6/2021 | Jauert | C12N 1/185 |
| 11,421,212 | B2 * | 8/2022 | Miller | C12N 9/2428 |
| 2011/0269185 | A1 | 11/2011 | David | |
| 2012/0045812 | A1 | 2/2012 | Bergsma | |

FOREIGN PATENT DOCUMENTS

| | | | |
|---|---|---|---|
| CN | 107058116 | A | 8/2017 |
| EP | 0186066 | B1 | 3/1993 |
| WO | 2001042482 | A1 | 6/2001 |
| WO | 2012019159 | A1 | 2/2012 |
| WO | 2016127083 | A1 | 8/2016 |
| WO | 2016160584 | A1 | 10/2016 |
| WO | 2017106739 | A1 | 6/2017 |
| WO | 2018027131 | A1 | 2/2018 |
| WO | 2018053230 | A1 | 3/2018 |
| WO | 2018204798 | A1 | 11/2018 |
| WO | 2019191263 | A1 | 10/2019 |

OTHER PUBLICATIONS

Ashikari T et al: "Rhizopus Raw-Starch-Degrading Glucoamylase Its Cloning and Expression in Yeast", Agricultural and Biological Chemistry, Agricultural Chemical Society of Japan, JP, vol. 50, No. 4, Jan. 1, 1986 (Jan. 1, 1986), pp. 957-964, XP008120586, ISSN: 0002-1369.

Database Geneseq [Online] Mar. 29, 2012 (Mar. 29, 2012), "Rhizopus oryzae glucoamylase (RhGA), SEQ ID 8.", XP002805077, retrieved from EBI accession No. GSP:AZT47646 Database accession No. AZT47646.

Database Geneseq [Online] Dec. 27, 2018 (Dec. 27, 2018), Rhizopus microsporus glucoamylase, SEQ ID 108 XP002805075, retrieved from EBI accession No. GSP:BFU53535 Database accession No. BFU53535.

Database UniParc [Online] Dec. 15, 2014 (Dec. 15, 2014), "Rhizopus microsporus Glucoamylase", XP002805076, accession No. UniParc-UPI00053810D6 Database accession No. UPI00053810D6.

Putative Glucoamylase (Fragment) {Rhizopus Microsporus] Genbank: CEG69155.1; Publication [online]. Apr. 9, 2015. Retrieved from the Internet: <URL:https://www.ncbi.nlm.nih.gov/protein/CEG69155.1?report-genbank&log$=protalign&blast_rank=1&RID=CDXU8B3X015?; p. 1.

* cited by examiner

*Primary Examiner* — Ganapathirama Raghu

(57) ABSTRACT

The invention is directed to an engineered yeast including an exogenous nucleic acid encoding a glucoamylase comprising SEQ ID NO:1 and SEQ ID NO:4, or a variant thereof. The engineered yeast are able to provide glucoamylase into a fermentation media and cause degradation of starch material generating glucose for fermentation to a desired bioproduct, such as ethanol. High titers of bioproduct (e.g., 70 g/kg of ethanol) can be achieved, along with low residual glucose levels. Further the yeast exhibit good growth and bioproduct product at temperatures of 32° C. or greater.

18 Claims, 1 Drawing Sheet

Specification includes a Sequence Listing.

Global Protein alignment Mol 1 Rhizopus oryzae GA (1 to 604) Mol 2 Rhizopus microsporus GA (1 to 605)
Scoring matrix: BLOSUM 62

Sequence View: Similarity Format, Color areas of high matches at same base position

| | | |
|---|---|---|
| Rhizopus oryzae | 1 | [illegible] |
| Rhizopus microsp | 1 | [illegible] |
| Rhizopus oryzae | 160 | [illegible] |
| Rhizopus microsp | 161 | [illegible] |
| Rhizopus oryzae | 320 | [illegible] |
| Rhizopus microsp | 321 | [illegible] |
| Rhizopus oryzae | 480 | [illegible] |
| Rhizopus microsp | 481 | [illegible] |

SEQUENCE LISTING

```
<160> NUMBER OF SEQ ID NOS: 29

<210> SEQ ID NO 1
<211> LENGTH: 605
<212> TYPE: PRT
<213> ORGANISM: Rhizopus microsporus

<400> SEQUENCE: 1

Met Lys Leu Met Asn Pro Ser Met Lys Ala Tyr Val Phe Phe Ile Leu
1               5                   10                  15

Ser Tyr Phe Ser Leu Leu Val Ser Ser Ala Ala Val Pro Thr Ser Ala
            20                  25                  30

Ala Val Gln Val Glu Ser Tyr Asn Tyr Asp Gly Thr Thr Phe Ser Gly
        35                  40                  45

Arg Ile Phe Val Lys Asn Ile Ala Tyr Ser Lys Val Val Thr Val Ile
    50                  55                  60
```

-continued

```
Tyr Ser Asp Gly Ser Asp Asn Trp Asn Asn Asn Asn Asn Lys Val Ser
65                  70                  75                  80

Ala Ala Tyr Ser Glu Ala Ile Ser Gly Ser Asn Tyr Glu Tyr Trp Thr
                85                  90                  95

Phe Ser Ala Lys Leu Ser Gly Ile Lys Gln Phe Tyr Val Lys Tyr Glu
            100                 105                 110

Val Ser Gly Ser Thr Tyr Tyr Asp Asn Asn Gly Thr Lys Asn Tyr Gln
        115                 120                 125

Val Gln Ala Thr Ser Ala Thr Ser Thr Thr Ala Thr Ala Thr Thr Thr
    130                 135                 140

Thr Ala Thr Gly Thr Thr Thr Thr Ser Thr Gly Pro Thr Ser Thr Ala
145                 150                 155                 160

Ser Val Ser Phe Pro Thr Gly Asn Ser Thr Ile Ser Ser Trp Ile Lys
                165                 170                 175

Asn Gln Glu Glu Ile Ser Arg Phe Ala Met Leu Arg Asn Ile Asn Pro
            180                 185                 190

Pro Gly Ser Ala Thr Gly Phe Ile Ala Ala Ser Leu Ser Thr Ala Gly
        195                 200                 205

Pro Asp Tyr Tyr Tyr Ser Trp Thr Arg Asp Ser Ala Leu Thr Ala Asn
    210                 215                 220

Val Ile Ala Tyr Glu Tyr Asn Thr Thr Phe Thr Gly Asn Thr Thr Leu
225                 230                 235                 240

Leu Lys Tyr Leu Lys Asp Tyr Val Thr Phe Ser Val Lys Ser Gln Ser
                245                 250                 255

Val Ser Thr Val Cys Asn Cys Leu Gly Glu Pro Lys Phe Asn Ala Asp
            260                 265                 270

Gly Ser Ser Phe Thr Gly Pro Trp Gly Arg Pro Gln Asn Asp Gly Pro
        275                 280                 285

Ala Glu Arg Ala Val Thr Phe Met Leu Ile Ala Asp Ser Tyr Leu Thr
    290                 295                 300

Gln Thr Lys Asp Ala Ser Tyr Val Thr Gly Thr Leu Lys Pro Ala Ile
305                 310                 315                 320

Phe Lys Asp Leu Asp Tyr Val Val Ser Val Trp Ser Asn Gly Cys Tyr
                325                 330                 335

Asp Leu Trp Glu Glu Val Asn Gly Val His Phe Tyr Thr Leu Met Val
            340                 345                 350

Met Arg Lys Gly Leu Ile Leu Gly Ala Asp Phe Ala Ala Arg Asn Gly
        355                 360                 365

Asp Ser Ser Arg Ala Ser Thr Tyr Lys Gln Thr Ala Ser Thr Met Glu
    370                 375                 380

Ser Lys Ile Ser Ser Phe Trp Ser Asp Ser Asn Asn Tyr Val Gln Val
385                 390                 395                 400

Ser Gln Ser Val Thr Ala Gly Val Ser Lys Lys Gly Leu Asp Val Ser
                405                 410                 415

Thr Leu Leu Ala Ala Asn Ile Gly Ser Leu Pro Asp Gly Phe Phe Thr
            420                 425                 430

Pro Gly Ser Glu Lys Ile Leu Ala Thr Ala Val Ala Leu Glu Asn Ala
        435                 440                 445

Phe Ala Ser Leu Tyr Pro Ile Asn Ser Asn Leu Pro Ser Tyr Leu Gly
    450                 455                 460

Asn Ser Ile Gly Arg Tyr Pro Glu Asp Thr Tyr Asn Gly Asn Gly Asn
465                 470                 475                 480
```

-continued

```
Ser Gln Gly Asn Pro Trp Phe Leu Ala Val Asn Ala Tyr Ala Glu Leu
                485                 490                 495

Tyr Tyr Arg Ala Ile Lys Glu Trp Ile Ser Asn Gly Lys Val Thr Val
            500                 505                 510

Ser Asn Ile Ser Leu Pro Phe Phe Lys Lys Phe Asp Ser Ser Ala Thr
        515                 520                 525

Ser Gly Lys Thr Tyr Thr Ala Gly Thr Ser Asp Phe Asn Asn Leu Ala
    530                 535                 540

Gln Asn Ile Ala Leu Gly Ala Asp Arg Phe Leu Ser Thr Val Lys Phe
545                 550                 555                 560

His Ala Tyr Thr Asn Gly Ser Leu Ser Glu Glu Tyr Asp Arg Ser Thr
                565                 570                 575

Gly Met Ser Thr Gly Ala Arg Asp Leu Thr Trp Ser His Ala Ser Leu
            580                 585                 590

Ile Thr Val Ala Tyr Ala Lys Ala Gly Ser Pro Ala Ala
        595                 600                 605


<210> SEQ ID NO 2
<211> LENGTH: 1818
<212> TYPE: DNA
<213> ORGANISM: Rhizopus microsporus

<400> SEQUENCE: 2

atgaagctaa tgaacccatc tatgaaagct tatgtctttt tcatcttatc atacttctct      60

ctcctagttt catctgccgc agtgcctaca tctgctgccg tccaagtgga aagttacaat     120

tacgatggca ctaccttctc cggccgtatc ttcgtgaaaa acattgctta ctcaaaagtt     180

gttacagtga tttactccga tggttctgat aattggaaca acaataacaa caaagtttca     240

gcagcgtact ccgaagccat tagtggatct aactacgaat actggacttt ctccgcaaag     300

ttgtctggta ttaagcaatt ctacgtaaag tacgaagttt caggttcaac atactacgat     360

aacaatggta ctaaaaacta ccaggtacaa gccacaagcg ctacaagtac aactgccaca     420

gctacaacta caactgctac agggacaaca actacatcaa ccggtccaac atcaaccgca     480

tctgtctcct ttccaaccgg taacagtaca atatcatcat ggatcaaaaa ccaagaggaa     540

atctcaagat ttgcaatgtt gagaaacatc aatccaccag ggtcagcgac tggtttcatc     600

gccgcttcat tgtccaccgc tgggccagac tactattact cttggactag agactctgca     660

ttgacagcaa acgttatagc ttacgaatac aacacaacct tcactggtaa cactaccttg     720

ttgaagtatc ttaaagacta cgtcactttt agtgttaagt ctcaatctgt ttctaccgtc     780

tgtaactgtt taggtgaacc aaagtttaat gcagatggct catcatttac tggtccatgg     840

ggcagacctc aaaacgatgg accagcagaa agagcagtca cattcatgtt gatcgctgac     900

tcatacttga cacaaactaa ggatgcttca tacgtgactg gaacactcaa gccagccata     960

ttcaaagacc tggattatgt tgtttctgtg tggtctaatg gttgctacga tttgtgggag    1020

gaagttaatg gcgtacattt ctacacacta atggttatga gaaagggact aattcttggg    1080

gcagatttcg cagctagaaa tggtgattcc tcaagagcat ctacctacaa gcaaacagca    1140

tctacaatgg aatcaaagat cagctctttc tggtctgact ctaacaacta cgttcaagtt    1200

tcacaatctg tgactgctgg tgtaagtaaa aagggtttag atgtttctac tctgttagct    1260

gcaaacattg gttctttacc agatggcttc tttacaccag gatcagaaaa gattttggca    1320

actgccgttg ccttagagaa tgcattcgct tccctttacc ctattaactc taacttacct    1380

tcatatttgg gtaattcaat tggtagatat ccagaggaca catacaacgg aaacgggaat    1440
```

-continued

```
tcacagggca acccttggtt cttagccgta aacgcgtacg ccgagttata ctacagagcc   1500

attaaggaat ggatctcaaa tggtaaggta acagtctcta atatctctct tcctttcttt   1560

aaaaagttcg attctagcgc cactagcggc aagacctata cagccggaac aagtgatttc   1620

aataacctcg ctcagaacat agctcttgga gcagacagat ttctgtcaac tgttaaattt   1680

cacgcgtaca caaatggcag cttgtctgaa gagtacgatc gttccaccgg gatgagtact   1740

ggtgctagag atctaacctg gtcccatgca tctcttatca cagttgcata cgcaaaagct   1800

ggatctcctg ctgcgtaa                                                 1818
```

```
<210> SEQ ID NO 3
<211> LENGTH: 1818
<212> TYPE: DNA
<213> ORGANISM: Rhizopus microsporus

<400> SEQUENCE: 3
```

```
atgaaactta tgaatccatc tatgaaggca tacgttttct ttatcttaag ctacttctct     60

ttactcgtta gctcagctgc ggtgccaacc tctgccgccg tacaagttga gtcatacaat    120

tatgacggta ccactttttc aggtagaata ttcgtcaaaa acattgccta ctcaaaggtc    180

gtaacagtta tctactccga tggatcagat aactggaaca ataacaacaa caaagtttct    240

gcagcttact cagaagcaat ttctgggtct aactacgaat actggacatt ctccgcaaag    300

ttatccggaa ttaaacagtt ttatgtcaaa tacgaagttt ctggttcaac atattacgac    360

aacaacggta ccaaaaacta ccaagtccaa gcaacctcag cgacatctac aacagctact    420

gcaaccacaa ctacagctac tggcacaaca actacttcta caggtccaac tagtactgca    480

tccgtatcat tccctaccgg taactcaaca atttcttcct ggataaaaaa tcaagaggaa    540

atcagccgtt ttgctatgtt gagaaatatc aatccacctg ggtctgccac agggttcata    600

gccgcatctc tgtccacagc cggcccagat tactattact cttggactag agattcagca    660

ctaacagcta atgtgatcgc ttacgaatac aacacaacat tcactggaaa caccaccctt    720

cttaagtact tgaaagatta cgttacattt tctgtcaaaa gccaatctgt atctaccgtt    780

tgtaactgtc tgggagaacc aaagttcaac gctgatggta gttcttttac aggtccatgg    840

ggcagaccac aaaacgacgg accagcagag agagctgtta cttttatgtt gattgctgac    900

agctacttga ctcaaactaa ggacgcatcc tacgttaccg gtacattaaa gccagcaatc    960

ttcaaagatc ttgattacgt agtttctgtt tggtctaacg gttgctacga tttatgggaa   1020

gaggttaatg gtgttcattt ctatactctc atggtcatga gaaagggttt gatcttaggt   1080

gccgacttcg ctgctagaaa tggtgactct agtagagctt caacctacaa gcaaactgca   1140

tcaacaatgg aatcaaagat cagttctttt tggtcagatt ctaacaacta cgtccaagtt   1200

tctcaatcag ttaccgccgg agtgtcaaaa aagggactag atgttagtac actattggcg   1260

gccaacattg gtagtctgcc tgatggcttt ttcactccag gctccgaaaa gatattggct   1320

acagcagtgg cgttagaaaa tgcattcgca tccttgtacc caattaactc taacctacct   1380

tcttacttgg gtaactcaat tggaagatat cctgaggata catacaacgg taatggcaac   1440

tctcagggga atccatggtt ccttgccgtc aacgcatacg cagaacttta ctacagagct   1500

attaaggaat ggattagtaa tggcaaggtg acagtatcca atatctcact acctttcttc   1560

aaaaagtttg attcttccgc cacttctgga aagacataca ctgctggtac atcagatttc   1620

aataacttgg ctcagaacat tgctttaggc gccgatagat tcctgtctac tgttaagttc   1680
```

-continued

```
cacgcataca ctaacgggag tctatcagaa gagtacgata gatctaccgg tatgagtact   1740

ggggctcgtg atttaacatg gtcccatgct tcattgatca cagtggcgta cgcaaaggcc   1800

ggtagtcctg cagcttag                                                 1818


<210> SEQ ID NO 4
<211> LENGTH: 604
<212> TYPE: PRT
<213> ORGANISM: Rhizopus delemar

<400> SEQUENCE: 4

Met Gln Leu Phe Asn Leu Pro Leu Lys Val Ser Phe Phe Leu Val Leu
1               5                   10                  15

Ser Tyr Phe Ser Leu Leu Val Ser Ala Ala Ser Ile Pro Ser Ser Ala
            20                  25                  30

Ser Val Gln Leu Asp Ser Tyr Asn Tyr Asp Gly Ser Thr Phe Ser Gly
        35                  40                  45

Lys Ile Tyr Val Lys Asn Ile Ala Tyr Ser Lys Lys Val Thr Val Ile
    50                  55                  60

Tyr Ala Asp Gly Ser Asp Asn Trp Asn Asn Asn Gly Asn Thr Ile Ala
65                  70                  75                  80

Ala Ser Tyr Ser Ala Pro Ile Ser Gly Ser Asn Tyr Glu Tyr Trp Thr
                85                  90                  95

Phe Ser Ala Ser Ile Asn Gly Ile Lys Glu Phe Tyr Ile Lys Tyr Glu
            100                 105                 110

Val Ser Gly Lys Thr Tyr Tyr Asp Asn Asn Asn Ser Ala Asn Tyr Gln
        115                 120                 125

Val Ser Thr Ser Lys Pro Thr Thr Thr Thr Ala Thr Ala Thr Thr Thr
    130                 135                 140

Thr Ala Pro Ser Thr Ser Thr Thr Thr Pro Pro Ser Ser Ser Glu Pro
145                 150                 155                 160

Ala Thr Phe Pro Thr Gly Asn Ser Thr Ile Ser Ser Trp Ile Lys Lys
                165                 170                 175

Gln Glu Gly Ile Ser Arg Phe Ala Met Leu Arg Asn Ile Asn Pro Pro
            180                 185                 190

Gly Ser Ala Thr Gly Phe Ile Ala Ala Ser Leu Ser Thr Ala Gly Pro
        195                 200                 205

Asp Tyr Tyr Tyr Ala Trp Thr Arg Asp Ala Ala Leu Thr Ser Asn Val
    210                 215                 220

Ile Val Tyr Glu Tyr Asn Thr Thr Leu Ser Gly Asn Lys Thr Ile Leu
225                 230                 235                 240

Asn Val Leu Lys Asp Tyr Val Thr Phe Ser Val Lys Thr Gln Ser Thr
                245                 250                 255

Ser Thr Val Cys Asn Cys Leu Gly Glu Pro Lys Phe Asn Pro Asp Gly
            260                 265                 270

Ser Gly Tyr Thr Gly Ala Trp Gly Arg Pro Gln Asn Asp Gly Pro Ala
        275                 280                 285

Glu Arg Ala Thr Thr Phe Ile Leu Phe Ala Asp Ser Tyr Leu Thr Gln
    290                 295                 300

Thr Lys Asp Ala Ser Tyr Val Thr Gly Thr Leu Lys Pro Ala Ile Phe
305                 310                 315                 320

Lys Asp Leu Asp Tyr Val Val Asn Val Trp Ser Asn Gly Cys Phe Asp
                325                 330                 335

Leu Trp Glu Glu Val Asn Gly Val His Phe Tyr Thr Leu Met Val Met
            340                 345                 350
```

```
Arg Lys Gly Leu Leu Leu Gly Ala Asp Phe Ala Lys Arg Asn Gly Asp
        355                 360                 365

Ser Thr Arg Ala Ser Thr Tyr Ser Ser Thr Ala Ser Thr Ile Ala Asn
    370                 375                 380

Lys Ile Ser Ser Phe Trp Val Ser Ser Asn Asn Trp Ile Gln Val Ser
385                 390                 395                 400

Gln Ser Val Thr Gly Gly Val Ser Lys Lys Gly Leu Asp Val Ser Thr
                405                 410                 415

Leu Leu Ala Ala Asn Leu Gly Ser Val Asp Asp Gly Phe Phe Thr Pro
            420                 425                 430

Gly Ser Glu Lys Ile Leu Ala Thr Ala Val Ala Val Glu Asp Ser Phe
        435                 440                 445

Ala Ser Leu Tyr Pro Ile Asn Lys Asn Leu Pro Ser Tyr Leu Gly Asn
    450                 455                 460

Ser Ile Gly Arg Tyr Pro Glu Asp Thr Tyr Asn Gly Asn Gly Asn Ser
465                 470                 475                 480

Gln Gly Asn Pro Trp Phe Leu Ala Val Thr Gly Tyr Ala Glu Leu Tyr
                485                 490                 495

Tyr Arg Ala Ile Lys Glu Trp Ile Gly Asn Gly Gly Val Thr Val Ser
            500                 505                 510

Ser Ile Ser Leu Pro Phe Phe Lys Lys Phe Asp Ser Ser Ala Thr Ser
        515                 520                 525

Gly Lys Lys Tyr Thr Val Gly Thr Ser Asp Phe Asn Asn Leu Ala Gln
    530                 535                 540

Asn Ile Ala Leu Ala Ala Asp Arg Phe Leu Ser Thr Val Gln Leu His
545                 550                 555                 560

Ala His Asn Asn Gly Ser Leu Ala Glu Glu Phe Asp Arg Thr Thr Gly
                565                 570                 575

Leu Ser Thr Gly Ala Arg Asp Leu Thr Trp Ser His Ala Ser Leu Ile
            580                 585                 590

Thr Ala Ser Tyr Ala Lys Ala Gly Ala Pro Ala Ala
        595                 600
```

<210> SEQ ID NO 5
<211> LENGTH: 1815
<212> TYPE: DNA
<213> ORGANISM: Rhizopus delemar

<400> SEQUENCE: 5

```
atgcagctgt tcaacttgcc attaaaggtt tcattctttt tggtcctatc atactttagt      60

ttgttggtgt cagccgcatc tattccatct tcagcatctg tacaattaga ctcctacaat     120

tacgacggct ctacattcag cggaaagatt tacgtgaaaa atattgcgta cagcaaaaaa     180

gtaactgtta tctatgccga cggatcagat aactggaaca acaatggaaa cactatcgct     240

gccagttact ctgcaccaat ttcaggttct aactacgaat attggacatt ctcagcctcc     300

atcaatggca ttaaggaatt ctacataaag tacgaagttt ccggtaagac ttactacgat     360

aacaacaatt ctgcaaacta tcaagtatca acatcaaaac ctactaccac caccgccaca     420

gctacaacta caactgcacc ttcaacatct accacaaccc caccatcttc tagcgaacca     480

gctacattcc caactggcaa ttctactatt tctagttgga tcaaaaaaca agagggtatt     540

tccagattcg caatgttgag aaacataaat ccaccaggat cagcaactgg attcatcgca     600

gcttctttgt ccacagcggg gccagattac tactacgcat ggaccagaga tgctgctttg     660
```

-continued

```
acaagtaacg ttattgttta cgaatacaat accactttgt ccggtaacaa gactattctt    720

aacgtcctaa aggattacgt tacattctct gttaagactc agtctacatc cacagtctgc    780

aattgtttgg gtgaaccaaa gttcaaccca gatggctctg gatacacagg tgcctggggt    840

cgtccacaaa acgatgggcc tgccgagaga gccactacat ttatcctatt tgctgactca    900

taccttacac aaacaaaaga tgcatcctac gtgactggaa cattaaagcc tgcaatcttc    960

aaagacctgg attacgttgt caacgtgtgg tctaacggct gtttcgatct atgggaagag   1020

gttaacggcg tgcacttcta cactctaatg gtcatgagaa agggtctgtt gttaggtgca   1080

gattttgcta agagaaacgg tgattctaca cgtgcttcta cctactcctc aacagcatca   1140

actattgcga acaagatttc ttcattttgg gtttcaagta ataactggat acaagtatct   1200

caaagcgtta caggggggtgt ctcaaaaaag ggtcttgatg tttctacatt actggctgct   1260

aatcttgggt ctgttgatga cggtttcttc accccctggtt ctgaaaagat cctcgctacc   1320

gccgtcgcgg ttgaggatag ttttgcttca ctctatccta taaacaaaaa ccttccttca   1380

tacttaggaa acagtatcgg tagataccca gaggatacat acaatggtaa tggcaattca   1440

cagggaaatc catggttcct tgctgttaca gggtacgcag aactttacta tagagctatt   1500

aaggaatgga tcggcaacgg cggtgtgaca gtttcctcaa tctcattgcc atttttcaaa   1560

aagtttgact ccagcgcgac atctggtaaa aagtatactg tggggacttc tgatttcaac   1620

aatttggctc aaaacattgc cttagctgcc gacagattct tatctaccgt acaactccat   1680

gcacataaca atggtagttt ggcagaggaa tttgatagaa ctacaggact ctctacaggt   1740

gcgagagatt taacttggtc acatgcaagt ttaattacag cctcttacgc aaaggctggt   1800

gctcctgctg cataa                                                     1815
```

<210> SEQ ID NO 6
<211> LENGTH: 1815
<212> TYPE: DNA
<213> ORGANISM: Rhizopus delemar

<400> SEQUENCE: 6

```
atgcagttat tcaacttacc acttaaggta tctttctttc tagtcttatc ttacttttca     60

ttgttagtat cagctgcctc tataccaagt tcagcatccg tacaactaga ttcatacaat    120

tacgacggtt caacattctc aggaaagata tacgtgaaaa atattgctta cagcaaaaag    180

gttactgtga tttacgcaga tgggtcagac aactggaata acaatggaaa cacaattgct    240

gcttcctatt ctgcccctat ttctggatct aactacgaat actggacttt ttcagcgagt    300

ataaacggaa ttaaggaatt ctatatcaaa tatgaagtct ctggtaagac ctactacgat    360

aacaacaact ccgcaaacta ccaagttagc acatcaaagc caaccacaac aactgctact    420

gcgacaacta caaccgcacc aagcacttct actacaacac ctcctagttc atctgagcca    480

gcaactttcc caactggtaa ttccactatt tcttcttgga tcaaaaaaca agagggtatc    540

tcaagattcg ccatgcttag aaatatcaat cctccaggct ctgcaacagg attcattgca    600

gcatctttat caactgcggg gccagactac tactacgcct ggactagaga tgcagctttg    660

acatcaaatg tgattgttta tgaatacaac acaactttgt ccggtaacaa gacaatcttg    720

aacgtcttga aggattatgt gacattctct gtcaagactc aatctacatc aacagtttgt    780

aactgtctcg gcgaaccaaa gttcaaccct gatggtagtg gttacactgg tgcttggggt    840

agaccacaaa acgatggtcc agcagagaga gctacaactt tcatcttgtt tgctgactct    900

tacctaacac aaaccaagga tgcaagctac gttactggaa cactaaagcc tgcaatcttt    960
```

aaagacctgg actatgttgt aaacgtttgg tcaaatggct gcttcgatct atgggaggaa 1020
gtgaacggtg ttcacttcta cacattaatg gtcatgagaa agggactctt gcttggtgca 1080
gactttgcta agagaaacgg tgattctaca cgtgcctcca cttactcctc cacagcttca 1140
accattgcca acaaaatctc ttctttctgg gtcagctcaa ataactggat tcaagtttct 1200
caatcagtta ctggtggtgt ttctaaaaag ggcctggatg tgtcaacctt gcttgctgcc 1260
aatttgggca gtgttgatga cgggttcttc accccaggtt ctgaaaagat cctcgccacc 1320
gcagttgccg ttgaagattc atttgctagt ttatacccaa tcaacaaaaa tctaccatca 1380
taccttggaa attcaatcgg tagatatcca gaggatacat acaacggtaa tggaaactct 1440
cagggtaacc cttggtttct tgcagttaca gggtacgctg aactgtacta cagagcgatt 1500
aaggaatgga ttggtaatgg cggcgtaact gttagttcta tttctctacc tttcttcaaa 1560
aagttcgata gttctgcaac atctggtaaa aagtacacag tcggcacttc cgattttaac 1620
aatttagctc agaacatagc actggcagct gatcgtttct tgagtacagt ccaattgcat 1680
gcccataaca acggtagttt ggctgaagag tttgatagaa ccaccggttt atcaaccggc 1740
gccagagatt taacatggtc ccatgcgtct ttgataactg cttcttacgc caaggctggg 1800
gcaccagctg cctga 1815

<210> SEQ ID NO 7
<211> LENGTH: 1815
<212> TYPE: DNA
<213> ORGANISM: Rhizopus delemar

<400> SEQUENCE: 7
atgcagttat tcaacttacc acttaaggta tctttctttc tagtcttatc ttacttttca 60
ttgttagtat cagctgcctc tataccaagt tcagcatccg tacaactaga ttcatacaat 120
tacgacggtt caacattctc aggaaagata tacgtgaaaa atattgctta cagcaaaaag 180
gttactgtga tttacgcaga tgggtcagac aactggaata acaatggaaa cacaattgct 240
gcttcctatt ctgcccctat ttctggatct aactacgaat actggacttt ttcagcgagt 300
ataaacggaa ttaaggaatt ctatatcaaa tatgaagtct ctggtaagac ctactacgat 360
aacaacaact ccgcaaacta ccaagttagc acatcaaagc caaccacaac aactgctact 420
gcgacaacta caaccgcacc aagcacttct actacaacac ctcctagttc atctgagcca 480
gcaactttcc caactggtaa ttccactatt tcttcttgga tcaaaaaaca agagggtatc 540
tcaagattcg ccatgcttag aaatatcaat cctccaggct ctgcaacagg attcattgca 600
gcatctttat caactgcggg gccagactac tactacgcct ggactagaga tgcagctttg 660
acatcaaatg tgattgttta tgaatacaac acaactttgt ccggtaacaa gacaatcttg 720
aacgtcttga aggattatgt gacattctct gtcaagactc aatctacatc aacagtttgt 780
aactgtctcg gcgaaccaaa gttcaaccct gatggtagtg gttacactgg tgcttggggt 840
agaccacaaa acgatggtcc agcagagaga gctacaactt tcatcttgtt tgctgactct 900
tacctaacac aaaccaagga tgcaagctac gttactggaa cactaaagcc tgcaatcttt 960
aaagacctgg actatgttgt aaacgtttgg tcaaatggct gcttcgatct atgggaggaa 1020
gtgaacggtg ttcacttcta cacattaatg gtcatgagaa agggactctt gcttggtgca 1080
gactttgcta agagaaacgg tgattctaca cgtgcctcca cttactcctc cacagcttca 1140
accattgcca acaaaatctc ttctttctgg gtcagctcaa ataactggat tcaagtttct 1200

```
caatcagtta ctggtggtgt ttctaaaaag ggcctggatg tgtcaacctt gcttgctgcc   1260

aatttgggca gtgttgatga cgggttcttc accccaggtt ctgaaaagat cctcgccacc   1320

gcagttgccg ttgaagattc atttgctagt ttatacccaa tcaacaaaaa tctaccatca   1380

taccttggaa attcaatcgg tagatatcca gaggatacat acaacggtaa tggaaactct   1440

cagggtaacc cttggtttct tgcagttaca gggtacgctg aactgtacta cagagcgatt   1500

aaggaatgga ttggtaatgg cggcgtaact gttagttcta tttctctacc tttcttcaaa   1560

aagttcgata gttctgcaac atctggtaaa aagtacacag tcggcacttc cgattttaac   1620

aatttagctc agaacatagc actggcagct gatcgtttct tgagtacagt ccaattgcat   1680

gcccataaca acggtagttt ggctgaagag tttgatagaa ccaccggttt atcaaccggc   1740

gccagagatt taacatggtc ccatgcgtct ttgataactg cttcttacgc caaggctggg   1800

gcaccagctg cctga                                                    1815
```

<210> SEQ ID NO 8
<211> LENGTH: 1818
<212> TYPE: DNA
<213> ORGANISM: Rhizopus microsporus

<400> SEQUENCE: 8

```
atgaagctga tgaatcctag catgaaagca tatgtgtttt tcatcctctc atacttcagc     60

ttgctagtta gttcggccgc agtacccacg tcggccgcgg tccaagtgga gtcgtataat    120

tatgacggaa ctaccttctc agggcgtata ttcgtcaaga atattgcgta ttccaaagtc    180

gtcacagtaa tctattcaga tggctccgat aattggaata ataataacaa caaggttagc    240

gccgcctatt ccgaggctat ttctggatca aactacgaat actggacctt ctcggcgaag    300

ctgtcaggga tcaaacagtt ttacgtcaag tacgaggtca gtggttcaac ttactacgat    360

aataacggaa ccaaaaatta tcaggtccag gcgacgagcg caacgtccac aactgcgaca    420

gccactacca ctactgctac cgggactacg acaacctcga caggaccgac gtccaccgcc    480

tctgtatcct ttcccaccgg aaacagcaca atttcgagct ggataaaaaa ccaagaggaa    540

atctctcgct tcgctatgtt acgtaacatc aatccccccg gttcggcaac tgggtttatt    600

gccgcatcat tatctacagc cgggcccgat tactattata gctggactcg cgacagtgca    660

ctcacggcta atgtcatcgc atatgaatac aacacgactt tcaccggcaa tacgaccctt    720

cttaagtatt tgaaagatta tgtaactttc tcagttaaaa gtcaatcggt tagtacggtc    780

tgtaattgtc tcggtgaacc gaagtttaac gctgacgggt cctcgttcac tggcccttgg    840

gggcgacctc agaacgacgg gcccgcggaa cgcgccgtta cgttcatgct cattgcagac    900

tcatatctca cccagactaa agacgcgtct tatgtcactg ggactttaaa accagctata    960

tttaaagatc tggattacgt tgtttctgtt tggtcaaatg ggtgttatga cttatgggaa   1020

gaagtgaacg gcgttcattt ctacacttta atggtcatgc ggaagggcct cattttaggg   1080

gcggacttcg ccgcacgtaa tggagattca tcgcgcgcgt caacatataa acaaacggca   1140

tcaactatgg aaagtaaaat ttctagcttc tggtcggaca gtaacaacta cgttcaagtg   1200

tctcaatcgg taactgcggg ggtaagcaag aagggacttg acgtgagtac actgcttgcc   1260

gccaatattg ggagcctacc agacgggttt tttacacccg gctcggaaaa gatttagca    1320

acggctgttg ctcttgaaaa cgcttttgcc tcgctgtatc caatcaattc aaatttacca   1380

tcttatctgg gaaatagtat tggaaggtac cccgaggaca cctataatgg gaacggtaat   1440

tcccaaggta acccttggtt cttggctgtg aatgcctatg ccgagttgta ctatcgcgca   1500
```

-continued attaaggaat ggataagtaa tggcaaagtg acggtttcaa acatctccct acctttttc 1560 aaaaaattcg actccagtgc gacttctgga aaaacctata cagcgggcac ctccgacttc 1620
aataatctcg cgcagaatat tgcactcgga gcagaccgat ttctttctac agtgaaattc 1680
catgcgtaca cgaacggtag cttgtcagaa gagtacgacc ggtctaccgg catgtcaacg 1740
ggagcacgag atcttacttg gtcccatgca agtttaatta ctgtggcata cgctaaagca 1800
gggtcgccag cggcataa 1818

<210> SEQ ID NO 9
<211> LENGTH: 1800
<212> TYPE: DNA
<213> ORGANISM: Artificial Sequence
<220> FEATURE:
<223> OTHER INFORMATION: Mfa2-Rhizopus oryzae

<400> SEQUENCE: 9
atgaaattca tttctacctt tctcactttt attttagcgg ccgtttctgt cactgctggt 60
gcctcgatcc ccagctcggc cagcgtccaa ctggactcgt ataattatga cggatctacc 120
ttctcaggga aaatatacgt caagaatatt gcgtattcca aaaaagtcac agtagtctat 180
gccgatggct ccgataattg gaataataat ggaaacacaa ttgcggcctc atttccggg 240 cctatttctg gatcaaacta cgaatactgg accttctcgg cgtcggtgaa agggatcaaa 300
gagttttaca ttaagtacga ggtcagtggt aaaacttact acgataataa caactcagct 360
aattatcagg tcagcacgag caagccgact acaactacgg cagccactac cactactact 420
gccccgtcta cgagtaccac aacacggccg agttcctcag aacctgcaac ttttcccacc 480
ggaaacagca caatttcgag ctggataaaa aagcaagagg atatctctcg cttcgctatg 540
ttacgtaaca tcaatccccc cggttcggca actgggttta ttgccgcatc attatctaca 600
gccgggcccg attactatta tgcgtggact cgcgacgcgg cactcacgtc taatgtcatc 660
gtatatgaat acaacacgac tctatcaggc aataagacca tccttaacgt tttgaaagat 720
tatgtaactt tctcagttaa aacgcaatcg acttcgaccg tctgtaattg cttgggcgag 780
ccaaaattca atccggacgg ttcgggatat accggtgctt ggggccgtcc gcagaacgac 840
ggcccggccg aacgagctac gacgttcgta ttattcgcgg attcatactt gacgcaaact 900
aaggacgctt cctatgttac gggtacttta aagcctgcaa tttttaaaga ccttgactat 960
gttgttaatg tctggtcaaa cggttgtttc gatttgtggg aagaggtgaa tggtgttcac 1020
ttctatactc tgatggttat gcggaaagga ttattactag ggcagactt tgcaaaacga 1080 aacggtgatt cgaccagagc ctcgacttat tctagcacag cctccacgat cgcaaataaa 1140
attagcagtt tctgggtaag tagtaacaac tgggtccagg tttctcagtc ggttacgggc 1200
ggcgtaagta agaaggggct tgatgtctca accctactgg cggcaaacct gggttccgta 1260
gatgatggat ttttcactcc tggaagcgaa aaaattcttg ccacagctgt tgccgtagag 1320
gattcgtttg cttcattata tccaattaat aagaacttac cgtcttacct gggaaatgca 1380
ataggccgat atccggagga tacctataat ggtaacggta atagccaagg taacccttgg 1440
tttcttgcgg tcacaggtta tgcagaactg tattacagag cgatcaaaga atggatatct 1500
aatggaggag ttacagtttc atcgatttct ctccctttct tcaaaaagtt tgactcctca 1560
gctacaagtg gcaaaaaata cacggtcggt acaagcgact ttaataacct cgcacagaac 1620
atcgcccttg ctgccgatag gttcctgagc actgtgcaac ttcatgcacc gaacaacggt 1680

-continued

```
tcattggcag aagagttcga ccgaactacc ggtttctcca ctggagcgcg tgatttaacg   1740

tggagtcatg cttcgctgat cacagcgtcg tatgctaagg caggcgcccc ggctgcctaa   1800


<210> SEQ ID NO 10
<211> LENGTH: 1548
<212> TYPE: DNA
<213> ORGANISM: Saccharomycopsis fibuligera

<400> SEQUENCE: 10

atgataaggc tcactgtttt cctcaccgca gtcttcgctg cggtcgcatc atgcgtgccg     60

gtcgagttgg acaagcgaaa cacaggccac ttccaagcgt attctgggta cacagttgcc    120

cgttcgaact ttacccagtg gatacatgag cagcccgcag tttcttggta ttatttactt    180

caaaacatcg attatcccga aggccaattt aaatctgcta aacctggagt agtagttgcg    240

tcaccctcaa ccagtgaacc cgattacttt taccagtgga cgagagatac agcaataaca    300

ttccttagtc ttattgcaga agtggaagac cacagttttt cgaacactac cttagcgaag    360

gttgttgagt actatatttc caatacatat acactacaga gggtaagcaa tccatctggg    420

aactttgatt cacctaatca tgatgggtta ggggagccca agttcaacgt ggacgatacc    480

gcctatacag cttcatgggg ccggccacag aacgatggac cggcactacg tgcgtatgcg    540

atttcgcgtt atctcaatgc cgttgctaag cataataatg gcaaactcct attagcgggc    600

caaaatggaa tcccttatag ttcagcgtca gatatatatt ggaagatcat taaaccggac    660

ctacagcacg tttctaccca ctggtccact tcggggttcg atctatggga agaaaaccaa    720

ggcacccact tttttactgc cttagtacaa ctaaaagctc ttagttatgg aatccctctc    780

tccaaaacgt acaatgaccc tgggttcact tcgtggttgg aaaaacaaaa ggatgctcta    840

aacagctaca ttaactcatc cggctttgtg aactcgggaa aaaagcacat cgtcgagtcc    900

ccgcaattaa gtagccgtgg tggcttagac tctgctactt acattgcagc tttgattacg    960

catgacattg gtgatgatga tacctatacg ccttttaacg ttgataattc atacgtgctt   1020

aattctctat actatttact ggtcgataac aagaatcggt ataaaataaa cggaaactat   1080

aaggctggcg cagctgtcgg acgctacccc gaggatgtct ataacggagt cggtacgtca   1140

gagggcaatc cttggcagct agcaacagcg tacgcaggac aaaccttcta tactctcgca   1200

tataacagtc taaagaacaa gaagaatctc gtgatagaga agcttaatta tgatttgtac   1260

aacagtttca tagcggattt gtcgaaaatc gactcctcgt atgcttcgaa ggattcttta   1320

acccttacat atggttcaga caactataag aatgttatca aatctctatt acaattcgga   1380

gatagttttc tcaaggtatt gctagaccat atcgatgaca acggtcaatt gaccgaagag   1440

attaataggt atactgggtt tcaagctggc gcggtcagtt tgacgtggag tagtgggtca   1500

ttgttaagtg cgaatcgagc acggaataag ttaatcgagt tattataa                1548


<210> SEQ ID NO 11
<211> LENGTH: 1920
<212> TYPE: DNA
<213> ORGANISM: Aspergillus kawachii

<400> SEQUENCE: 11

atgagcttcc ggtccttgct ggcattgagt ggcctagttt gctcaggact tgcgagtgtg     60

attagtaaaa gagcaacccct cgactcctgg ctctccaacg aagctacggt agcacgtacc    120

gctatcctaa ataatatcgg cgcggatgga gcgtgggtat ctggtgcgga ttccggtatc    180

gtcgtagcat caccttcaac tgataatccc gattattttt atacttggac acgggatagc    240
```

```
ggccttgtca ttaagacttt ggttgacctt ttcagaaatg gggacaccga cctcctgtcg    300

acgatcgagc attatatatc aagccaagcg ataatacaag gagtatctaa tcctagcggg    360

gatttgtcga gtggcggttt gggcgagccc aagttcaacg tggacgagac tgcatatacg    420

ggatcatggg gccgtcctca acgagatgga ccagcgctac gcgccaccgc tatgattggc    480

tttggccagt ggctgctaga taacgggtac acatctgcgg ctacggaaat cgtttggcca    540

ttggtccgta atgacctttc atatgtcgct cagtactgga accaaactgg ctacgattta    600

tgggaggaag tgaatggtag ctcatttttc accattgccg tgcagcaccg ggcgttagtt    660

gaaggatcgg cctttgcaac ggcggttgga tcatcctgta gctggtgtga tagccaagcc    720

cctcaaattc tatgttacct tcaatcattc tggacaggta gttacatcct tgctaatttc    780

gattccagtc ggtccgggaa agacacgaat acactcttgg gctccattca cacctttgac    840

ccggaggcgg gctgcgatga ttcaactttc cagccatgct ctccaagagc ccttgcaaat    900

cacaaagaag tggtggattc ctttcgtagc atttatactc tcaatgacgg tttgtccgac    960

tcagaggctg ttgctgttgg ccgatatccg gaagatagct attataatgg caacccgtgg   1020

tttttatgca cattagctgc ggccgaacag ctctatgacg ctttatacca gtgggacaaa   1080

cagggttcac tagaaatcac agatgtgtca ctcgattttt tcaaggcctt gtactcagga   1140

gccgctactg ggacatactc gtcgagtagt tcgacatatt caagcattgt ttcggcagtt   1200

aagacgttcg cggacgggtt cgtcagcata gtagagacac atgccgccag taacgggtcg   1260

ctaagcgaac aattcgataa atcggatgga gatgaactca gcgctcgtga tcttacctgg   1320

tcttatgccg cactgttaac agccaataat cgtcgtaact ctgttgtgcc acctagttgg   1380

ggagagacat ccgcaagctc agtccccggg acgtgtgccg ccacctccgc atccggtacg   1440

tattccagtg ttaccgttac cagctggcca tctattgtag ctacgggtgg aacaacgacc   1500

accgctacga cgactggcag tggaggtgta acttcaacat ctaaaacaac gaccacagcg   1560

tctaagactt ctaccactac aagttcaacc tcctgcacga cccctacagc ggtggccgtt   1620

acattcgacc tcacggccac caccacttac ggggaaaaca tttacctagt ggggtctata   1680

tcccaattag gagactggga gacttcagat ggaatcgcgc tatcggccga taaatatacg   1740

tcctctaacc cgttatggta tgtgacagta actttaccag cgggagagag cttcgaatat   1800

aagttcatcc gagtggaatc agatgatagc gtggagtggg agtcggaccc aaatcgggag   1860

tatactgtcc ctcaggcttg cggtgagtcc actgctaccg taacggatac atggcgctaa   1920
```

<210> SEQ ID NO 12
<211> LENGTH: 1911
<212> TYPE: DNA
<213> ORGANISM: Aspergillus terreus

<400> SEQUENCE: 12

```
atgacgagga tcttgactct ggcattgcac ggcctagctc tggtccagtc agtggtgggg     60

gccccgcaac tagcaccccg ggcaaccacg tcgttggacg cctggctggc atcggaaacc    120

actgtagcat tagatggaat cctggataac gtgggctcgt ctggtgcgta tgctaaatca    180

gccaagtcgg gcattgtcat tgcctccccc tccacttccg atcctgacta ctactatacg    240

tggacccgag atgcggcttt gactgtaaaa gcactaatcg acctatttcg gaacggggag    300

acatcattgc agaccgtgat tatggagtac atctcgtcgc aagcctatct gcaaactgta    360

agtaatcctt ccggctcgct ttcgacgggc ggtctggcag aacctaaata ttatgttgat    420
```

-continued

```
gagactgcgt acaccggaag ttgggggcgg cctcaacgag atggaccagc gctacgcgca    480
acggcaatga ttgactttgg gaattggtta attgacaatg gctattctac atatgcctca    540
tccattgtat ggcctatagt ccgtaatgac ctttcttatg tagcccagta ttggaaccaa    600
actgggtatg atttgtggga ggaggtaaac ggttcttcat tcttcaccat tgcagtgcag    660
catagagcct tggtcgaggg ctcaaccttc gcttccaaag tcggtgcatc ttgctcatgg    720
tgtgactctc aggctccaca ggtcctttgt tttctccaac gcttctggac tgggtcttac    780
ataatggcaa actttggcgg tggtaggtca ggtaaggacg cgaacaccgt gcttggttca    840
attcacacgt tcgaccctaa cgcgggctgt gacgatacga cttttcagcc gtgttccccc    900
cgtgcgttag ctaatcacaa agtatatacc gatagctttc ggtccattta ttccattaat    960
tcagggattt ccagcggtaa agctgtcgcg gtgggccgct atccggagga ttcttactat   1020
aatggaaacc cctggttttt aacgacgctc gcggctgccg agcaactata tgacgctatc   1080
tatcagtggc aaaaaatagg cagtattact attacggacg tgtcgctcgc gttcttcaag   1140
gatctttact cttctgcggc ggtagggaca tatgcaagta gtagtagcgc ctttacctca   1200
attgtgagcg cggtaaagac gtatgctgac ggctatatgt ccatcgttca aacacacgct   1260
atgactaatg gctcgttatc cgaacagttc ggtaagtcag atggcttttc tctatctgct   1320
agggacttaa cgtggtcgta cgcagcccta ctgaccgcca atctgaggcg taattccgtc   1380
gttccacctt cctggggtga aacgactgcc acttcagtgc cctcggtttg ttcggctacg   1440
tctgcaacag ggacctattc tacggcgact aatacagcat ggccatctac cctcacttct   1500
ggaacgggcg caacgactac gacttctaaa gctacaagtt catcaactac gacgacctct   1560
tcggcgagct caactacagt agagtgcgtg gtccccaccg ctgtagcggt cacatttgac   1620
gaggtggcga ctacgactta tggtgagaac gtatacgttg tcggcagtat cagtcagctc   1680
ggctcttggg atacgtccaa agcagtggct ttatctgcgt cgaagtatac ttcgagcaac   1740
aacctgtggt atgttacggt aacccttccg gctggcacca ctttccagta caagttcatc   1800
cgggtatcat cgtcgggttc cgtcacttgg gaaagcgatc cgaatcgctc ttatacagtg   1860
ccctcggcct gtggtacgtc aacagctgtc gtcaatacca cttggcgcta a            1911
```

<210> SEQ ID NO 13
<211> LENGTH: 1854
<212> TYPE: DNA
<213> ORGANISM: Thermomyces lanuginosus

<400> SEQUENCE: 13

```
atgctgttcc agcctactct gtgcgccgca cttgggttag cggccctcat cgtgcagggc     60
ggcgaggcac gcccggagac tactgtgcca cacgctaccg gttcgctaga tgatttcctt    120
gcggctcaga gccccatcgc ttttcagggc attttaaata atataggacc ctccggcgct    180
tattccgaag gtgttaatcc cggtgtagta atcgctagcc cctcaaaaca agaccctgat    240
tatttctata catgggtcag ggacgccgca ctcacggtac agtatctagt cgaagagttg    300
gtggcgggaa atgcatcgtt acaatttctg attcaagact acatctcttc ccaagcacga    360
ctccagacgg tggagaaccc ttcgggtagc ctatcatccg gcggtttagg tgaaccgaaa    420
ttccacgtcg acgagacagc gttcactgat tcctggggac gcccccaacg agatgggcca    480
ccattaaggg ctatagctat gatttccttc gctaattatt taatagataa tggccatcaa    540
tcgacagttg aggatattat ctggcccatt gttagaaatg acctttctta cgtcagccaa    600
cattggaacg agacaacatt cgatatttgg gaggaggtcc attcgagtag ctttttcacc    660
```

accgccgtgc aatatcgagc tttggttcaa ggtagtgctc tagcctctaa actaggtcac 720
acttgcgaca attgtggttc tcaggctccc cagatcttgt gctttctaca gtcctactgg 780
actggctccc atatacttgc taacacgggt ggcggtagga gcggaaagga tgtaagtacc 840
atcctcggcg tgattggtag tttcgatcct aatgctgact gtgatgatgt aactttccaa 900
ccctgtagcg cccgggcttt agctaatcat aaacaagtgg ttgatagctt tcgctctatc 960
tacgcgatca atgctgggat cccttctggg tcagctgtag cagtcggacg ttatccggag 1020
gacgtgtatc agggtggcca cccttggtac ttgacgaccg cagctgccgc tgagcagctt 1080
tatgacgcca tatatcaatg gaaccacgtg ggacacatag acatcaacgc tgtcaactta 1140
gatttcttca aaagcatata cccgagtgcg gcagaaggaa cgtacacaag cgattcatca 1200
acctttcagg acataatcag tgcggttcgc acatatgccg acggtttctt gtctgtaata 1260
gaaaaatata ccccaccgga taacctttta gccgaacaat tccatcgtga gacaggtata 1320
cctctcagcg cagccagtct gacctggtca tacgcggctt tgaataccgc tgcacaacgc 1380
agggcttcca tagttccctc cccctggaat agtaatagca ctgacctacc ggataaatgt 1440
agtgcgactt cagcaacagg tccatatgcc acacctacta acacggcctg gccgactacg 1500
actcagcctc ccgaacggcc ggcctgtact ccgccgtcag aagtaacgct gacctttaac 1560
gcactcgtag acaccgcctt tggtcagaac atctacttgg tgggaagcat acctgagttg 1620
ggctcttggg acccagcaaa tgccttgcta atgagtgcaa agtcatggac ctctgggaat 1680
cctgtatgga ctttatctat atcgctacct gctggaacgt cgttcgagta caaatttata 1740
cgcaaagacg atggctcatc tgacgtggta tgggagtcgg acccaaatcg gtcgtataat 1800
gtccctaagg attgcggtgc gaatactgct accgtaaact cctggtggcg ctaa 1854

<210> SEQ ID NO 14
<211> LENGTH: 2045
<212> TYPE: DNA
<213> ORGANISM: Artificial Sequence
<220> FEATURE:
<223> OTHER INFORMATION: Mfa2-Neurospora crassa

<400> SEQUENCE: 14
atgaaattca tttctacctt tctcactttt attttagcgg ccgtttctgt cactgctgac 60
gcgatctata atctgaagca agtacttcta tctaaccatg actttacgac gagcttggtg 120
tccaacgcaa ccgacttctc cacgtcgccc ctgacctatt tcgcaatgca tttggtttcg 180
agtttacttg tagtcggggc tgcattccaa gcagttttag ggttgcctga tccccttcac 240
gagaaacgcc attctgatat tatcaaacgt tccgtcgatt cgtacatcca aacggaaacc 300
cccattgcgc aaaagaacct actttgcaac atcggagcaa gcggatgccg agcctccgga 360
gccgcgtccg ggtggtagt cgcatcgcct tcaaaaagca gtcctgatta ctggtatact 420
tggacccggg atgcagcgct agtgacaaag ttgatcgttg acgagtttac taatgattat 480
aataccacgt tacagaacac catccaggca tacgcggctg cccaagctaa gttgcaaggc 540
gtcagtaacc catccggaag cctcagtaat ggggctgggt taggagaacc caagtttatg 600
gttgatctac aacaatttac cggtgcatgg ggtaggcccc aacgagatgg gccccctctg 660
cgtgcgatcg ctttgatagg gtacggaaag tggttagtct cgaacggcta tgcagacacg 720
gctaagtcaa ttatttggcc catcgtcaag aatgatttag cctatacagc tcagtattgg 780
aataacactg gatttgacct atgggaagaa gttaactcct ccagtttctt tacgattgcg 840
gcgtcccacc gggctttggt tgaagggtca gctttcgcga agtccgtggg ctcctcatgt 900
agcgcgtgcg acgctatagc gccccaaatc ttgtgctttc aacagagctt ttggtcaaat 960
agcggttata ttatctccaa ctttgtcaat taccgatcgg gtaaagatat taattcagtc 1020
ctaacttcca tacataattt tgatccggcg gccggttgtg acgtaaatac tttccaacct 1080
tgctcggatc gggctttagc gaaccacaag gtcgtagttg atagtatgcg attctggggt 1140
gtgaactcag gtaggaccgc aggcaaagct gcggcagtgg gacggtacgc ggaggacgtt 1200
tattacaatg gtaacccatg gtacctagca acgctagcgg cagccgagca gctatacgac 1260
gccgtctatg tctggaagaa gcagggaagt ataactgtta catccacctc gttggcattt 1320
tttaaggact tagttccttc agtctcgact ggtacctaca gctctagttc ttctacatat 1380
actgcgatca ttaacgctgt aacgacatat gcagacggct ttgtcgacat agttgcccaa 1440
tatactccat ccgatgggtc cttggcggaa caatttgata aggattcggg tgccccattg 1500
agcgctacac acctaacctg gtcttacgcg tctttttctat cggctgctgc aaggcgcgca 1560
gggattgtgc ctccatcctg ggtgcagcg tcagccaata gtctgcccgg ttcgtgcagc 1620
gcctctacag tagcaggaag ttatgccacc gctacagcga cctcgtttcc ggcaaacctg 1680
actccggctt caactacagt gacaccacct acccaaacag gctgcgcagc agatcatgaa 1740
gttctggtta ctttcaacga aaaagttacg acaagttatg gtcagacggt aaaggtggta 1800
ggttctatag cagcccttgg gaattgggcc cctgcgagcg gagtgacgct ctcggcaaaa 1860
cagtactcct cctcaaatcc attatggtct acgaccattg ctttgcctca agggacctcg 1920
tttaaatata aatatgttgt cgttaatagt gatggatctg taaaatggga gaatgatccc 1980
gatcgcagct atgccgtagg aacagattgt gcttccacag ccactcttga tgatacttgg 2040
aggta 2045

<210> SEQ ID NO 15
<211> LENGTH: 4863
<212> TYPE: DNA
<213> ORGANISM: Artificial Sequence
<220> FEATURE:
<223> OTHER INFORMATION: Mfa2-Rhizopus oryzae GA integration construct

<400> SEQUENCE: 15
ctaaattcgg ccttgctcag agactcctgg attttggcta acaacgcagt cccttcgatg 60
catatagcta ggccacaaat tatgccaata acggtccatg ggttgatgtt ttcttgaatt 120
ctttcgtttt tcatgctatt tgcgtcttcc caagtcccag cgttccagta ttcatactgc 180
gcgttagagt ggtagccata agagccggca tattggtaat tttcagtatt aacgttagaa 240
cgtggtgaat acgatgtggt ccagccttgc ctcgttgtgt catatacgat ctttttcttt 300
gggtcacaaa gaatatcata tgcttgagag atgactttaa atctatgtag tttttcgctt 360
gatgttagca gcagcggtga tttactatca ctgttggtaa ccttttctga gctaaatatt 420
tgaatgttat cggaatggtc agggtggtac aattttacat aacgatgata ttttttttt 480 aacgacttct tgtccagttt aggatttcca gatccggcct ttggaatgcc aaaaatatca 540
tagggagttg gatctgccaa ctcaggccat tgttcatccc ttatcgtaag ttttctattg 600
ccatttttat cgttcgctgt agcatactta gctataaaag tgatttgtgg gggacacttt 660
tctacacatg ataagtgcca cttgaataaa aatgggtata cgaacttatg gtgtagcata 720
acaaatatat tgcaagtagt gacctatggt gtgtagatat acgtacagtt agttacgagc 780
ctaaagacac aacgtgtttg ttaattatac tgtcgctgta atatcttctc ttccattatc 840

```
accggtcatt ccttgcaggg gcggtagtac ccggagaccc tgaacttttc tttttttttt    900
tgcgaaatta aaaagttcat tttcaattcg acaatgagat ctacaagcca ttgttttatg    960
ttgatgagag ccagcttaaa gagttctcga gatctcccga gtttatcatt atcaatactg   1020
ccatttcaaa gaatacgtaa ataattaata gtagtgattt tcctaacttt atttagtcaa   1080
aaaattggcc ttttaattct gctgtaaccc gtacatgccc aaaatagggg gcgggttaca   1140
cagaatatat aacatcatag gtgtctgggt gaacagttta ttcctggcat ccactaaata   1200
taatggagcc cgcttttttt aagctggcat ccagaaaaaa aaagaatccc agcaccaaaa   1260
tattgttttc ttcaccaacc atcagttcat aggtccattc tcttagcgca actacacaga   1320
acaggggcac aaacaggcaa aaaacgggca caacctcaat ggagtgatgc aacctgcttg   1380
gagtaaatga tgacacaagg caattgacct acgcatgtat ctatctcatt ttcttacacc   1440
ttctattacc ttctgctctc tctgatttgg aaaaagctga aaaaaaaggt tgaaaccagt   1500
tccctgaaat tattccccta tttgactaat aagtatataa agacggtagg tattgattgt   1560
aattctgtaa atctatttct taaacttctt aaattctact tttatagtta gtcttttttt   1620
tagtttaaaa caccaagaac ttagtttcga ataaacacac ataaacaaac aaatctagaa   1680
tgaagttcat ttccactttc ttgaccttca ttttggctgc tgtctctgtc accgctgcat   1740
ctattccatc tagtgcatct gtacaattgg actcctacaa ttacgatggt tccacatttt   1800
ccggcaagat ttatgtcaaa aacatcgctt actctaaaaa ggttactgtt gtgtacgcag   1860
acggttctga caactggaac aataacggca acactattgc tgcatcattt tcaggcccaa   1920
tctctggatc aaattacgaa tactggacat tctcagcatc agtgaagggc ataaaggagt   1980
tctacatcaa atacgaagtt tcaggtaaga catattacga caataacaac tctgcaaact   2040
accaagtctc aacttctaaa cctactacaa ctactgcagc tacaaccaca actacagctc   2100
catcaacttc tacaacaacc cgtccatcta gttcagagcc tgccaccttc cctactggta   2160
attctaccat cagctcttgg atcaaaaagc aggaagatat ttccagattc gctatgctta   2220
gaaacatcaa cccacctggt tctgccacag ggtttatcgc cgcatcactc tctaccgctg   2280
gtccagatta ctactacgcg tggacaagag atgccgcttt gacatctaac gttatcgttt   2340
acgaatacaa caccacattg tctgggaata agacaattct aaacgtactt aaggattacg   2400
tcacattcag tgttaagaca cagtctactt caacagtttg taattgcctt ggtgaaccaa   2460
agttcaatcc agacggcagt ggttacacag gtgcttgggg tagacctcaa aatgatggtc   2520
ctgcagaaag agcgactaca tttgttctgt ttgccgacag ctacttgact caaactaagg   2580
atgcctcata cgtcactggt acattaaagc cagcaatttt caaagatctc gattacgttg   2640
ttaacgtctg gagtaacgga tgtttcgatt tatgggagga ggtgaacgga gttcatttct   2700
acacccttat ggttatgaga aaagggctat tgttgggggc tgatttcgcg aagagaaacg   2760
gtgactcaac tagagcctca acttactctt ctactgcttc cacaattgct aacaagatat   2820
caagtttctg ggttagctca aacaactggg tgcaagtatc ccaatctgtc acaggaggtg   2880
taagtaaaaa ggggttagac gttagcaccc tgttagctgc gaatctagga tcagtcgatg   2940
atggattttt cactccaggt tctgaaaaga tattagctac agctgtggca gtcgaagatt   3000
cctttgccag tctataccca atcaacaaaa accttccatc atacttgggg aacgctattg   3060
gaagataccc tgaagataca tacaacggta atggtaactc acaaggcaat ccttggtttc   3120
tggcggttac cggctacgca gagttgtact atagagcaat taaggaatgg atttctaatg   3180
```

```
gaggcgttac agtgtcctct atctcattgc catttttcaa aaagttcgat agctctgcaa   3240

catccggtaa aaagtacacc gtaggtactt ctgacttcaa caatttagca caaaacattg   3300

ctcttgctgc agatcgtttc ctatctactg tacaactcca tgcaccaaac aatggttcat   3360

tagcagagga atttgataga acaacaggtt tttctaccgg cgctagagat ttaacatggt   3420

cccacgcctc attgataaca gcatcctatg ccaaagccgg tgctccagct gcataattaa   3480

ttaaacaggc cccttttcct ttgtcgatat catgtaatta gttatgtcac gcttacattc   3540

acgccctcct cccacatccg ctctaaccga aaaggaagga gttagacaac ctgaagtcta   3600

ggtccctatt tatttttta tagttatgtt agtattaaga acgttattta tatttcaaat    3660

ttttctttt tttctgtaca aacgcgtgta cgcatgtaac gggcagacgg ccggccataa    3720

cttcgtataa tgtatgctat acgaagttat ggcaacggtt catcatctca tggatctgca   3780

catgaacaaa caccagagtc aaacgacgtt gaaattgagg ctactgcgcc aattgatgac   3840

aatacagacg atgataacaa accgaagtta tctgatgtag aaaaggatta gagatgctaa   3900

gagatagtga tgatatttca taaataatgt aattctatat atgttaatta cctttttgc    3960

gaggcatatt tatggtgaag gataagtttt gaccatcaaa gaaggttaat gtggctgtgg   4020

tttcagggtc cataaagctt ttcaattcat ctttttttt tttgttcttt tttttgattc    4080

cggtttcttt gaaattttt tgattcggta atctccgagc agaaggaaga acgaaggaag    4140

gagcacagac ttagattggt atatatacgc atatgtggtg ttgaagaaac atgaaattgc   4200

ccagtattct taacccaact gcacagaaca aaaacctgca ggaaacgaag ataaatcatg   4260

tcgaaagcta catataagga acgtgctgct actcatccta gtcctgttgc tgccaagcta   4320

tttaatatca tgcacgaaaa gcaaacaaac ttgtgtgctt cattggatgt tcgtaccacc   4380

aaggaattac tggagttagt tgaagcatta ggtcccaaaa tttgtttact aaaaacacat   4440

gtggatatct tgactgattt ttccatggag ggcacagtta agccgctaaa ggcattatcc   4500

gccaagtaca attttttact cttcgaagac agaaaatttg ctgacattgg taatacagtc   4560

aaattgcagt actctgcggg tgtatacaga atagcagaat gggcagacat tacgaatgca   4620

cacggtgtgg tgggcccagg tattgttagc ggtttgaagc aggcggcgga agaagtaaca   4680

aaggaaccta gaggcctttt gatgttagca gaattgtcat gcaagggctc cctagctact   4740

ggagaatata ctaagggtac tgttgacatt gcgaagagcg acaaagattt tgttatcggc   4800

tttattgctc aaagagacat gggtggaaga gatgaaggtt acgattggtt gattatgaca   4860

cgc                                                                4863
```

```
<210> SEQ ID NO 16
<211> LENGTH: 4748
<212> TYPE: DNA
<213> ORGANISM: Artificial Sequence
<220> FEATURE:
<223> OTHER INFORMATION: Mfa2-Rhizopus oryzae GA integration construct

<400> SEQUENCE: 16

ggccgctcca tggagggcac agttaagccg ctaaaggcat tatccgccaa gtacaatttt     60

ttactcttcg aagacagaaa atttgctgac attggtaata cagtcaaatt gcagtactct    120

gcgggtgtat acagaatagc agaatgggca gacattacga atgcacacgg tgtggtgggc    180

ccaggtattg ttagcggttt gaagcaggcg gcggaagaag taacaaagga acctagaggc    240

cttttgatgt tagcagaatt gtcatgcaag ggctccctag ctactggaga atatactaag    300

ggtactgttg acattgcgaa gagcgacaaa gattttgtta tcggctttat tgctcaaaga    360
```

-continued

```
gacatgggtg gaagagatga aggttacgat tggttgatta tgacacccgg tgtgggttta    420
gatgacaagg gagacgcatt gggtcaacag tatagaaccg tggatgatgt ggtctctaca    480
ggatctgaca ttattattgt tggaagagga ctatttgcaa agggaaggga tgctaaggta    540
gagggtgaac gttacagaaa agcaggctgg gaagcatatt tgagaagatg cggccagcaa    600
aactaaaaaa ctgtattata agtaaatgca tgtatactaa actcacaaat tagagcttca    660
atttaattat atcagttatt acccgggaat ctcggtcgta atgattttta taatgacgaa    720
aaaaaaaaaa ttggaaagaa aaagcttcat ggcctttata aaaaggaacc atccaatacc    780
tcgccagaac caagtaacag tattttacgg ggcacaaatc aagaacaata agacaggact    840
gtaaagatgg acgcattgaa ctccaaagaa caacaagagt tccaaaaagt agtggaacaa    900
aagcaaatga aggatttcat gcgtttgata acttcgtata atgtatgcta tacgaagtta    960
tctcgagggc cagaaaaagg aagtgtttcc ctccttcttg aattgatgtt accctcataa   1020
agcacgtggc ctcttatcga gaaagaaatt accgtcgctc gtgatttgtt tgcaaaaaga   1080
acaaaactga aaaaacccag acacgctcga cttcctgtct tcctgttgat tgcagcttcc   1140
aatttcgtca cacaacaagg tcctagcgac ggctcacagg ttttgtaaca agcaatcgaa   1200
ggttctggaa tggcgggaaa gggtttagta ccacatgcta tgatgcccac tgtgatctcc   1260
agagcaaagt tcgttcgatc gtactgttac tctctctctt tcaaacagaa ttgtccgaat   1320
cgtgtgacaa caacagcctg ttctcacaca ctcttttctt ctaaccaagg gggtggttta   1380
gtttagtaga acctcgtgaa acttacattt acatatatat aaacttgcat aaattggtca   1440
atgcaagaaa tacatatttg gtcttttcta attcgtagtt tttcaagttc ttagatgctt   1500
tctttttctc ttttttacag atcatcaagg aagtaattat ctacttttta caagtctaga   1560
atgaagttta tctccacgtt tttaaccttt atcctagcag ctgtcagcgt caccgccgca   1620
tcaattccga gttcagcatc tgtacaactt gactcttaca attacgatgg cagcactttc   1680
tcagggaaaa tttatgtgaa aaacatagca tatagtaaga aggttaccgt ggtatatgca   1740
gacggttctg ataattggaa taataatgga aacactattg ccgccagttt ttccggccca   1800
atttctggtt ccaattacga gtattggacc ttttctgcat cagtaaaagg catcaaggaa   1860
ttctatatta agtacgaagt ttcaggtaag acatattacg ataacaataa ctcagcaaat   1920
tatcaagtct ctacatctaa gcccacaaca acaactgctg ctaccaccac tacaaccgct   1980
ccttctacca gcaccactac cagaccaagc tctagtgaac cggctacctt tcctaccgga   2040
aacagtacca tctcaagctg gatcaaaaag caagaggaca taagtcgttt tgctatgttg   2100
aggaacatta atcctccagg atccgcgacc ggtttcattg cagcatcact aagtactgcc   2160
gggcctgatt attattatgc ttggactaga gacgctgcat taacatcaaa cgtgattgtt   2220
tatgaatata atacgaccct ttccggtaat aaaacgatct tgaacgtatt aaaagactat   2280
gtgaccttta gtgtgaagac ccaatctaca tctacagtgt gtaattgttt gggagaacct   2340
aaattcaatc cagacggttc tgggtacact ggtgcctggg gtagacctca aaacgacggt   2400
ccagcagaaa gagcaacaac ctttgttcta tttgctgact cttatttaac gcaaacaaag   2460
gacgcctcat atgttacagg gaccctaaaa ccagcaattt tcaaagactt ggattatgtt   2520
gttaatgttt ggagcaacgg atgttttgac ttgtgggagg aggttaacgg tgtacacttt   2580
tatacattga tggtgatgag aaaagggttg ctattgggag cagatttcgc taaaagaaat   2640
ggtgattcta caagagcgag cacatatagt agcaccgctt caacaatcgc caataaaatc   2700
```

-continued

```
tcatctttct gggtatctag caacaactgg gtacaagttt cccaaagtgt taccggcggt   2760

gtgtccaaaa agggtttaga cgttagcaca cttctagctg ctaatttggg tagcgttgat   2820

gacgggtttt ttactccagg tagtgagaag atactggcaa ccgcggtggc ggttgaagac   2880

agctttgctt cattgtatcc tataaataaa aatctgccct cttatctggg taatgcaatt   2940

ggcagatacc cagaagatac ctacaatggt aatggtaatt cccaggggaa cccatggttt   3000

ttggctgtta caggctacgc agaactttat taccgtgcaa tcaaggaatg gatttcaaat   3060

ggcggcgtca ctgtcagtag tataagtttg ccctttttta agaaatttga ttcctcagca   3120

acgtctggta aaaaatacac cgtaggtact agtgatttca ataatttggc ccaaaatatt   3180

gcgcttgctg ctgacaggtt tcttagtacc gttcagttgc acgctccaaa taatggctca   3240

ttggctgaag aatttgatcg tacgacaggt ttctccactg gtgctaggga tttgacttgg   3300

agtcatgcct ccttaatcac agcaagctat gctaaagctg gtgcacctgc tgcttagtta   3360

attaatttac cagcttacta tccttcttga aaatatgcac tctatatctt ttagttctta   3420

attgcaacac atagatttgc tgtataacga attttatgct attttttaa tttggagttc   3480

ggtgatgaaa gtgtcacagc gaatttcctc acatgtaggg accgaattgt ttacaagttc   3540

tctgtaccac catggagaca tcaaagattg aaaatctatg gaaagatatg gacggtagca   3600

acaagaatat agcacgagcc gcggagttca tttcgttact tttgatatcg ctcacaacta   3660

ttgcgaagcg cttcagtgaa aaaatcataa ggaaaagttg taaatattat tggtagtatt   3720

cgtttggtaa agtagagggg gtaatttttc ccctttattt tgttcataca ttcttaaatt   3780

gctttgcctc tccttttgga aagctatact tcggagcact gttgagcgaa ggctcaggcc   3840

ggcagcacgc agcacgctgt atttacgtat ttaattttat atatttgtgc atacactact   3900

agggaagact tgaaaaaaac ctaggaaatg aaaaaacgac acaggaagtc ccgtatttac   3960

tattttttcc ttccttttga tggggcaggg cggaaataga ggataggata agcctactgc   4020

ttagctgttt ccgtctctac ttcggtagtt gtctcaattg tcgtttcagt attaccttta   4080

gagccgctag acgatggttg agctatttgt tgagggaaaa ctaagttcat gtaacacacg   4140

cataacccga ttaaactcat gaatagcttg attgcaggag gctggtccat tggagatggt   4200

gccttatttt ccttataggc aacgatgatg tcttcgtcgg tgttcaggta gtagtgtaca   4260

ctctgaatca gggagaacca ggcaatgaac ttgttcctca agaaaatagc ggccataggc   4320

atggattggt taaccacacc agatatgctt ggtgtggcag aatatagtcc ttttggtggc   4380

gcaattttct tgtacctgtg gtagaaaggg agcggttgaa ctgttagtat atattggcaa   4440

tatcagcaaa tttgaaagaa aattgtcggt gaaaaacata cgaaacacaa aggtcgggcc   4500

ttgcaacgtt attcaaagtc attgtttagt tgaggaggta gcagcggagt atatgtattc   4560

cttttttttg cctatggatg ttgtaccatg cccattctgc tcaagctttt gttaaaatta   4620

tttttcagta ttttttcttc catgttgcgc gttacgagaa cagaagcgac agataaccgc   4680

aatcatacaa ctagcgctac tgcggggtgt aaaaagcaca agaactaagc caagatcaca   4740

acagttat                                                            4748
```

<210> SEQ ID NO 17
<211> LENGTH: 1674
<212> TYPE: DNA
<213> ORGANISM: Artificial Sequence
<220> FEATURE:
<223> OTHER INFORMATION: Integration construct

<400> SEQUENCE: 17
ctaaattcgg ccttgctcag agactcctgg attttggcta acaacgcagt cccttcgatg 60
catatagcta ggccacaaat tatgccaata acggtccatg ggttgatgtt ttcttgaatt 120
ctttcgtttt tcatgctatt tgcgtcttcc caagtcccag cgttccagta ttcatactgc 180
gcgttagagt ggtagccata agagccggca tattggtaat tttcagtatt aacgttagaa 240
cgtggtgaat acgatgtggt ccagccttgc ctcgttgtgt catatacgat ctttttcttt 300
gggtcacaaa gaatatcata tgcttgagag atgactttaa atctatgtag tttttcgctt 360
gatgttagca gcagcggtga tttactatca ctgttggtaa ccttttctga gctaaatatt 420
tgaatgttat cggaatggtc agggtggtac aattttacat aacgatgata tttttttttt 480
aacgacttct tgtccagttt aggatttcca gatccggcct ttggaatgcc aaaaatatca 540
tagggagttg gatctgccaa ctcaggccat tgttcatccc ttatcgtaag ttttctattg 600
ccatttttat cgttcgctgt agcatactta gctataaaag tgatttgtgg gggacacttt 660
tctacacatg ataagtgcca cttgaataaa aatgggtata cgaacttatg gtgtagcata 720
acaaatatat tgcaagtagt gacctatggt gtgtagatat acgtacagtt agttacgagc 780
ctaaagacac aacgtgtttg ttaattatac tgtcgctgta atatcttctc ttccattatc 840
accggtcatt ccttgcaggg gcggtagtac ccggagaccc tgaacttttc tttttttttt 900
tgcgaaatta aaaagttcat tttcaattcg acaatgagat ctacaagcca ttgttttatg 960
ttgatgagag ccagcttaaa gagttctcga gatctcccga gtttatcatt atcaatactg 1020
ccatttcaaa gaatacgtaa ataattaata gtagtgattt tcctaacttt atttagtcaa 1080
aaaattggcc ttttaattct gctgtaaccc gtacatgccc aaaatagggg gcgggttaca 1140
cagaatatat aacatcatag gtgtctgggt gaacagttta ttcctggcat ccactaaata 1200
taatggagcc cgcttttttt aagctggcat ccagaaaaaa aaagaatccc agcaccaaaa 1260
tattgttttc ttcaccaacc atcagttcat aggtccattc tcttagcgca actacacaga 1320
acaggggcac aaacaggcaa aaaacgggca caacctcaat ggagtgatgc aacctgcttg 1380
gagtaaatga tgacacaagg caattgacct acgcatgtat ctatctcatt ttcttacacc 1440
ttctattacc ttctgctctc tctgatttgg aaaaagctga aaaaaaaggt tgaaaccagt 1500
tccctgaaat tattccccta tttgactaat aagtatataa agacggtagg tattgattgt 1560
aattctgtaa atctatttct taaacttctt aaattctact tttatagtta gtcttttttt 1620
tagtttaaaa caccaagaac ttagtttcga ataaacacac ataaacaaac aaat 1674

<210> SEQ ID NO 18
<211> LENGTH: 4260
<212> TYPE: DNA
<213> ORGANISM: Artificial Sequence
<220> FEATURE:
<223> OTHER INFORMATION: Mfa2-Rhizopus oryzae integration construct

<400> SEQUENCE: 18
tcgagatctc ccgagtttat cattatcaat actgccattt caaagaatac gtaaataatt 60
aatagtagtg attttcctaa ctttatttag tcaaaaaatt ggccttttaa ttctgctgta 120
acccgtacat gcccaaaata gggggcgggt tacacagaat atataacatc ataggtgtct 180
gggtgaacag tttattcctg gcatccacta aatataatgg agcccgcttt ttttaagctg 240
gcatccagaa aaaaaaagaa tcccagcacc aaaatattgt tttcttcacc aaccatcagt 300
tcataggtcc attctcttag cgcaactaca cagaacaggg gcacaaacag gcaaaaaacg 360

-continued

```
ggcacaacct caatggagtg atgcaacctg cttggagtaa atgatgacac aaggcaattg    420
acctacgcat gtatctatct cattttctta caccttctat taccttctgc tctctctgat    480
ttggaaaaag ctgaaaaaaa aggttgaaac cagttccctg aaattattcc cctatttgac    540
taataagtat ataaagacgg taggtattga ttgtaattct gtaaatctat ttcttaaact    600
tcttaaattc tacttttata gttagtcttt tttttagttt aaaacaccaa gaacttagtt    660
tcgaataaac acacataaac aaacaaatct agaatgaagt tcatttccac tttcttgacc    720
ttcattttgg ctgctgtctc tgtcaccgct gcatctattc catctagtgc atctgtacaa    780
ttggactcct acaattacga tggttccaca ttttccggca agatttatgt caaaaacatc    840
gcttactcta aaaaggttac tgttgtgtac gcagacggtt ctgacaactg gaacaataac    900
ggcaacacta ttgctgcatc attttcaggc ccaatctctg gatcaaatta cgaatactgg    960
acattctcag catcagtgaa gggcataaag gagttctaca tcaaatacga agtttcaggt   1020
aagacatatt acgacaataa caactctgca aactaccaag tctcaacttc taaacctact   1080
acaactactg cagctacaac cacaactaca gctccatcaa cttctacaac aacccgtcca   1140
tctagttcag agcctgccac cttccctact ggtaattcta ccatcagctc ttggatcaaa   1200
aagcaggaag atatttccag attcgctatg cttagaaaca tcaacccacc tggttctgcc   1260
acagggttta tcgccgcatc actctctacc gctggtccag attactacta cgcgtggaca   1320
agagatgccg ctttgacatc taacgttatc gtttacgaat acaacaccac attgtctggg   1380
aataagacaa ttctaaacgt acttaaggat tacgtcacat tcagtgttaa gacacagtct   1440
acttcaacag tttgtaattg ccttggtgaa ccaaagttca atccagacgg cagtggttac   1500
acaggtgctt ggggtagacc tcaaaatgat ggtcctgcag aaagagcgac tacatttgtt   1560
ctgtttgccg acagctactt gactcaaact aaggatgcct catacgtcac tggtacatta   1620
aagccagcaa ttttcaaaga tctcgattac gttgttaacg tctggagtaa cggatgtttc   1680
gatttatggg aggaggtgaa cggagttcat ttctacaccc ttatggttat gagaaaaggg   1740
ctattgttgg gggctgattt cgcgaagaga aacggtgact caactagagc ctcaacttac   1800
tcttctactg cttccacaat tgctaacaag atatcaagtt tctgggttag ctcaaacaac   1860
tgggtgcaag tatcccaatc tgtcacagga ggtgtaagta aaaaggggtt agacgttagc   1920
accctgttag ctgcgaatct aggatcagtc gatgatggat tttcactcc  aggttctgaa   1980
aagatattag ctacagctgt ggcagtcgaa gattcctttg ccagtctata cccaatcaac   2040
aaaaaccttc catcatactt ggggaacgct attggaagat accctgaaga tacatacaac   2100
ggtaatggta actcacaagg caatccttgg tttctggcgg ttaccggcta cgcagagttg   2160
tactatagag caattaagga atggatttct aatggaggcg ttacagtgtc ctctatctca   2220
ttgccatttt tcaaaaagtt cgatagctct gcaacatccg gtaaaaagta caccgtaggt   2280
acttctgact tcaacaattt agcacaaaac attgctcttg ctgcagatcg tttcctatct   2340
actgtacaac tccatgcacc aaacaatggt tcattagcag aggaatttga tagaacaaca   2400
ggtttttcta ccggcgctag agatttaaca tggtcccacg cctcattgat aacagcatcc   2460
tatgccaaag ccggtgctcc agctgcataa ttaattaaac aggccccttt tcctttgtcg   2520
atatcatgta attagttatg tcacgcttac attcacgccc tcctcccaca tccgctctaa   2580
ccgaaaagga aggagttaga caacctgaag tctaggtccc tatttatttt tttatagtta   2640
tgttagtatt aagaacgtta tttatatttc aaatttttct tttttttctg tacaaacgcg   2700
tgtacgcatg taacgggcag acggccggcc ataacttcgt ataatgtatg ctatacgaag   2760
```

ttatccttac atcacaccca atcccccaca agtgatcccc cacacaccat agcttcaaaa 2820
tgtttctact cctttttttac tcttccagat tttctcggac tccgcgcatc gccgtaccac 2880
ttcaaaacac ccaagcacag catactaaat ttcccctctt tcttcctcta gggtggcgtt 2940
aattacccgt actaaaggtt tggaaaagaa aaaagagacc gcctcgtttc tttttcttcg 3000
tcgaaaaagg caataaaaat ttttatcacg tttctttttc ttgaaaaatt tttttttga 3060 ttttttctc tttcgatgac ctcccattga tatttaagtt aataaatggt cttcaatttc 3120
tcaagtttca gtttcgtttt tcttgttcta ttacaacttt ttttacttct tgctcattag 3180
aaagaaagca tagcaatcta atctaagttt taattacaaa atgccacaat cctgggaaga 3240
attggccgcc gacaaacgtg cccgtttggc taaaaccatt cctgacgaat ggaaggttca 3300
aactttgcct gccgaagatt ccgttattga tttcccaaag aagtccggta ttttgtctga 3360
ggctgaattg aagattaccg aagcctctgc tgctgatttg gtctccaagt tggccgctgg 3420
tgagttgact tctgttgaag tcactttggc tttttgtaag agagctgcta ttgctcaaca 3480
attaaccaac tgtgctcacg aattcttccc agatgctgct ttagctcaag ctagagaatt 3540
agatgaatac tacgctaagc ataagagacc agttggtcca ttacacggtt taccaatctc 3600
tttaaaggac caattgcgtg ttaagggtta cgaaacctcc atgggttaca tttcctggtt 3660
aaacaaatac gatgaaggtg attccgtctt aaccaccatg ttgagaaaag ctggtgctgt 3720
tttctacgtt aagacctctg tcccacaaac cttgatggtc tgtgaaaccg tcaacaacat 3780
cattggtaga actgtcaatc caagaaacaa aaattggtcc tgtggtggtt cttctggtgg 3840
tgaaggtgct attgttggta ttagaggtgg tgttattggt gtcggtactg acattggtgg 3900
ttccattaga gtcccagctg ctttcaactt tttatacggt ttgagaccat ctcacggtag 3960
attgccatat gctaaaatgg ctaactctat ggaaggtcaa gaaaccgttc actccgtcgt 4020
tggtcctatc actcactccg tcgaagactt gagattgttc accaaatctg tcttgggtca 4080
agaaccttgg aagtacgact ctaaggtcat ccccatgcca tggagacaat ctgaatctga 4140
catcattgcc tctaagatta agaatggtgg tttgaacatt ggttattaca atttcgacgg 4200
taacgtcttg ccacacccac caattttacg tggtgtcgaa actaccgttg ccgctttggc 4260

<210> SEQ ID NO 19
<211> LENGTH: 5008
<212> TYPE: DNA
<213> ORGANISM: Artificial Sequence
<220> FEATURE:
<223> OTHER INFORMATION: Mfa2-Rhizopus oryzae GA integration construct

<400> SEQUENCE: 19
ggccgcgaag gtgctattgt tggtattaga ggtggtgtta ttggtgtcgg tactgacatt 60
ggtggttcca ttagagtccc agctgctttc aactttttat acggtttgag accatctcac 120
ggtagattgc catatgctaa aatggctaac tctatggaag gtcaagaaac cgttcactcc 180
gtcgttggtc ctatcactca ctccgtcgaa gacttgagat tgttcaccaa atctgtcttg 240
ggtcaagaac cttggaagta cgactctaag gtcatcccaa tgccatggag acaatctgaa 300
tctgacatca ttgcctctaa gattaagaat ggtggtttga acattggtta ttacaatttc 360
gacggtaacg tcttgccaca cccaccaatt ttacgtggtg tcgaaactac cgttgccgct 420
ttggccaagg ctggtcacac cgttactcca tggactccat acaagcatga tttcggtcat 480
gacttgattt cccacatcta tgctgctgat ggttctgccg acgtcatgag agacatttct 540

-continued

```
gcctctggtg agccagccat ccctaacatt aaggacttgt tgaacccaaa tattaaggct    600
gttaacatga acgaattgtg ggacactcat ttacaaaagt ggaactatca aatggaatac    660
ttggaaaagt ggcgtgaagc tgaagaaaaa gctggtaagg aattggacgc tattatcgct    720
ccaattactc ctaccgccgc tgtcagacac gatcaattca gatactacgg ttacgcctcc    780
gttattaact tattggattt cacctctgtt gtcgtcccag tcactttcgc tgataagaat    840
attgataaga agaacgaatc ttttaaagct gtttccgaat tggatgcttt ggttcaagaa    900
gaatacgacc cagaggctta tcacggtgct cctgttgctg ttcaagttat tggtagaaga    960
ttgtccgaag agagaacttt ggctatcgcc gaagaagtcg gtaaattgtt gggtaacgtc   1020
gtcactccat aagcgaattt cttatgattt atgattttta ttattaaata agttataaaa   1080
aaaataagtg tatacaaatt ttaaagtgac tcttaggttt taaaacgaaa attcttattc   1140
ttgagtaact ctttcctgta ggtcaggttg ctttctcagg tatagcatga ggtcgctctt   1200
attgaccaca cctctaccgg catgccgagc aaatgcctgc aaatcgctcc ccatttcacc   1260
caattgtaga tatgctaact ccagcaatga gttgatgaat ctcggtgtgt attttatgtc   1320
ctcagaggac aacacataac ttcgtataat gtatgctata cgaagttatc tcgagggcca   1380
gaaaaaggaa gtgtttccct ccttcttgaa ttgatgttac cctcataaag cacgtggcct   1440
cttatcgaga aagaaattac cgtcgctcgt gatttgtttg caaaaagaac aaaactgaaa   1500
aaacccagac acgctcgact tcctgtcttc ctgttgattg cagcttccaa tttcgtcaca   1560
caacaaggtc ctagcgacgg ctcacaggtt ttgtaacaag caatcgaagg ttctggaatg   1620
gcgggaaagg gtttagtacc acatgctatg atgcccactg tgatctccag agcaaagttc   1680
gttcgatcgt actgttactc tctctctttc aaacagaatt gtccgaatcg tgtgacaaca   1740
acagcctgtt ctcacacact cttttcttct aaccaagggg gtggtttagt ttagtagaac   1800
ctcgtgaaac ttacatttac atatatataa acttgcataa attggtcaat gcaagaaata   1860
catatttggt cttttctaat tcgtagtttt tcaagttctt agatgctttc tttttctctt   1920
ttttacagat catcaaggaa gtaattatct actttttaca agtctagaat gaagtttatc   1980
tccacgtttt taacctttat cctagcagct gtcagcgtca ccgccgcatc aattccgagt   2040
tcagcatctg tacaacttga ctcttacaat tacgatggca gcactttctc agggaaaatt   2100
tatgtgaaaa acatagcata tagtaagaag gttaccgtgg tatatgcaga cggttctgat   2160
aattggaata ataatggaaa cactattgcc gccagttttt ccggcccaat ttctggttcc   2220
aattacgagt attggacctt ttctgcatca gtaaaaggca tcaaggaatt ctatattaag   2280
tacgaagttt caggtaagac atattacgat aacaataact cagcaaatta tcaagtctct   2340
acatctaagc ccacaacaac aactgctgct accaccacta caaccgctcc ttctaccagc   2400
accactacca gaccaagctc tagtgaaccg gctacctttc ctaccggaaa cagtaccatc   2460
tcaagctgga tcaaaaagca agaggacata agtcgttttg ctatgttgag gaacattaat   2520
cctccaggat ccgcgaccgg tttcattgca gcatcactaa gtactgccgg gcctgattat   2580
tattatgctt ggactagaga cgctgcatta acatcaaacg tgattgttta tgaatataat   2640
acgacccttt ccggtaataa aacgatcttg aacgtattaa aagactatgt gacctttagt   2700
gtgaagaccc aatctacatc tacagtgtgt aattgtttgg gagaacctaa attcaatcca   2760
gacggttctg ggtacactgg tgcctggggt agacctcaaa acgacggtcc agcagaaaga   2820
gcaacaacct ttgttctatt tgctgactct tatttaacgc aaacaaagga cgcctcatat   2880
gttacaggga ccctaaaacc agcaattttc aaagacttgg attatgttgt taatgtttgg   2940
```

-continued agcaacggat gttttgactt gtgggaggag gttaacggtg tacactttta tacattgatg 3000
gtgatgagaa aagggttgct attgggagca gatttcgcta aaagaaatgg tgattctaca 3060
agagcgagca catatagtag caccgcttca acaatcgcca ataaaatctc atctttctgg 3120
gtatctagca acaactgggt acaagtttcc caaagtgtta ccggcggtgt gtccaaaaag 3180
ggtttagacg ttagcacact tctagctgct aatttgggta gcgttgatga cgggtttttt 3240
actccaggta gtgagaagat actggcaacc gcggtggcgg ttgaagacag ctttgcttca 3300
ttgtatccta taaataaaaa tctgccctct tatctgggta atgcaattgg cagataccca 3360
gaagatacct acaatggtaa tggtaattcc caggggaacc catggttttt ggctgttaca 3420
ggctacgcag aactttatta ccgtgcaatc aaggaatgga tttcaaatgg cggcgtcact 3480
gtcagtagta taagtttgcc cttttttaag aaatttgatt cctcagcaac gtctggtaaa 3540
aaatacaccg taggtactag tgatttcaat aatttggccc aaaatattgc gcttgctgct 3600
gacaggtttc ttagtaccgt tcagttgcac gctccaaata atggctcatt ggctgaagaa 3660
tttgatcgta cgacaggttt ctccactggt gctagggatt tgacttggag tcatgcctcc 3720
ttaatcacag caagctatgc taaagctggt gcacctgctg cttagttaat taatttacca 3780
gcttactatc cttcttgaaa atatgcactc tatatctttt agttcttaat tgcaacacat 3840
agatttgctg tataacgaat tttatgctat ttttttaatt tggagttcgg tgatgaaagt 3900
gtcacagcga atttcctcac atgtagggac cgaattgttt acaagttctc tgtaccacca 3960
tggagacatc aaagattgaa aatctatgga aagatatgga cggtagcaac aagaatatag 4020
cacgagccgc ggagttcatt tcgttacttt tgatatcgct cacaactatt gcgaagcgct 4080
tcagtgaaaa aatcataagg aaaagttgta aatattattg gtagtattcg tttggtaaag 4140
tagagggggt aatttttccc ctttattttg ttcatacatt cttaaattgc tttgcctctc 4200
cttttggaaa gctatacttc ggagcactgt tgagcgaagg ctcaggccgg cagcacgcag 4260
cacgctgtat ttacgtattt aattttatat atttgtgcat acactactag ggaagacttg 4320
aaaaaaacct aggaaatgaa aaaacgacac aggaagtccc gtatttacta ttttttcctt 4380
ccttttgatg gggcagggcg gaaatagagg ataggataag cctactgctt agctgtttcc 4440
gtctctactt cggtagttgt ctcaattgtc gtttcagtat tacctttaga gccgctagac 4500
gatggttgag ctatttgttg agggaaaact aagttcatgt aacacacgca taacccgatt 4560
aaactcatga atagcttgat tgcaggaggc tggtccattg gagatggtgc cttattttcc 4620
ttataggcaa cgatgatgtc ttcgtcggtg ttcaggtagt agtgtacact ctgaatcagg 4680
gagaaccagg caatgaactt gttcctcaag aaaatagcgg ccataggcat ggattggtta 4740
accacaccag atatgcttgg tgtggcagaa tatagtcctt ttggtggcgc aattttcttg 4800
tacctgtggt agaaagggag cggttgaact gttagtatat attggcaata tcagcaaatt 4860
tgaaagaaaa ttgtcggtga aaaacatacg aaacacaaag gtcgggcctt gcaacgttat 4920
tcaaagtcat tgtttagttg aggaggtagc agcggagtat atgtattcct tttttttgcc 4980
tatggatgtt gtaccatgcc cattctga 5008

<210> SEQ ID NO 20
<211> LENGTH: 4884
<212> TYPE: DNA
<213> ORGANISM: Artificial Sequence
<220> FEATURE:
<223> OTHER INFORMATION: Rhizopus microsporus GA integration construct

<400> SEQUENCE: 20
ctaaattcgg ccttgctcag agactcctgg attttggcta acaacgcagt cccttcgatg 60
catatagcta ggccacaaat tatgccaata acggtccatg ggttgatgtt ttcttgaatt 120
ctttcgtttt tcatgctatt tgcgtcttcc caagtcccag cgttccagta ttcatactgc 180
gcgttagagt ggtagccata agagccggca tattggtaat tttcagtatt aacgttagaa 240
cgtggtgaat acgatgtggt ccagccttgc ctcgttgtgt catatacgat ctttttcttt 300
gggtcacaaa gaatatcata tgcttgagag atgactttaa atctatgtag tttttcgctt 360
gatgttagca gcagcggtga tttactatca ctgttggtaa ccttttctga gctaaatatt 420
tgaatgttat cggaatggtc agggtggtac aattttacat aacgatgata ttttttttt 480
aacgacttct tgtccagttt aggatttcca gatccggcct ttggaatgcc aaaaatatca 540
tagggagttg gatctgccaa ctcaggccat tgttcatccc ttatcgtaag ttttctattg 600
ccatttttat cgttcgctgt agcatactta gctataaaag tgatttgtgg gggacacttt 660
tctacacatg ataagtgcca cttgaataaa aatgggtata cgaacttatg gtgtagcata 720
acaaatatat tgcaagtagt gacctatggt gtgtagatat acgtacagtt agttacgagc 780
ctaaagacac aacgtgtttg ttaattatac tgtcgctgta atatcttctc ttccattatc 840
accggtcatt ccttgcaggg gcggtagtac ccggagaccc tgaacttttc ttttttttt 900
tgcgaaatta aaaagttcat tttcaattcg acaatgagat ctacaagcca ttgttttatg 960
ttgatgagag ccagcttaaa gagttctcga gatctcccga gtttatcatt atcaatactg 1020
ccatttcaaa gaatacgtaa ataattaata gtagtgattt tcctaacttt atttagtcaa 1080
aaaattggcc ttttaattct gctgtaaccc gtacatgccc aaaatagggg gcgggttaca 1140
cagaatatat aacatcatag gtgtctgggt gaacagttta ttcctggcat ccactaaata 1200
taatggagcc cgcttttttt aagctggcat ccagaaaaaa aaagaatccc agcaccaaaa 1260
tattgttttc ttcaccaacc atcagttcat aggtccattc tcttagcgca actacacaga 1320
acaggggcac aaacaggcaa aaaacgggca caacctcaat ggagtgatgc aacctgcttg 1380
gagtaaatga tgacacaagg caattgacct acgcatgtat ctatctcatt ttcttacacc 1440
ttctattacc ttctgctctc tctgatttgg aaaaagctga aaaaaaaggt tgaaaccagt 1500
tccctgaaat tattcccccta tttgactaat aagtatataa agacggtagg tattgattgt 1560
aattctgtaa atctatttct taaacttctt aaattctact tttatagtta gtcttttttt 1620
tagtttaaaa caccaagaac ttagtttcga ataaacacac ataaacaaac aaatctagaa 1680
tgaaacttat gaatccatct atgaaggcat acgttttctt tatcttaagc tacttctctt 1740
tactcgttag ctcagctgcg gtgccaacct ctgccgccgt acaagttgag tcatacaatt 1800
atgacggtac cactttttca ggtagaatat tcgtcaaaaa cattgcctac tcaaaggtcg 1860
taacagttat ctactccgat ggatcagata actggaacaa taacaacaac aaagtttctg 1920
cagcttactc agaagcaatt tctgggtcta actacgaata ctggacattc tccgcaaagt 1980
tatccggaat taaacagttt tatgtcaaat acgaagtttc tggttcaaca tattacgaca 2040
acaacggtac caaaaactac caagtccaag caacctcagc gacatctaca acagctactg 2100
caaccacaac tacagctact ggcacaacaa ctacttctac aggtccaact agtactgcat 2160
ccgtatcatt ccctaccggt aactcaacaa tttcttcctg gataaaaaat caagaggaaa 2220
tcagccgttt tgctatgttg agaaatatca atccacctgg gtctgccaca gggttcatag 2280
ccgcatctct gtccacagcc ggcccagatt actattactc ttggactaga gattcagcac 2340

-continued

```
taacagctaa tgtgatcgct tacgaataca acacaacatt cactggaaac accacccttc   2400
ttaagtactt gaaagattac gttacatttt ctgtcaaaag ccaatctgta tctaccgttt   2460
gtaactgtct gggagaacca aagttcaacg ctgatggtag ttcttttaca ggtccatggg   2520
gcagaccaca aaacgacgga ccagcagaga gagctgttac ttttatgttg attgctgaca   2580
gctacttgac tcaaactaag gacgcatcct acgttaccgg tacattaaag ccagcaatct   2640
tcaaagatct tgattacgta gtttctgttt ggtctaacgg ttgctacgat ttatgggaag   2700
aggttaatgg tgttcatttc tatactctca tggtcatgag aaagggtttg atcttaggtg   2760
ccgacttcgc tgctagaaat ggtgactcta gtagagcttc aacctacaag caaactgcat   2820
caacaatgga atcaaagatc agttcttttt ggtcagattc taacaactac gtccaagttt   2880
ctcaatcagt taccgccgga gtgtcaaaaa agggactaga tgttagtaca ctattggcgg   2940
ccaacattgg tagtctgcct gatggctttt tcactccagg ctccgaaaag atattggcta   3000
cagcagtggc gttagaaaat gcattcgcat ccttgtaccc aattaactct aacctacctt   3060
cttacttggg taactcaatt ggaagatatc ctgaggatac atacaacggt aatggcaact   3120
ctcaggggaa tccatggttc cttgccgtca acgcatacgc agaactttac tacagagcta   3180
ttaaggaatg gattagtaat ggcaaggtga cagtatccaa tatctcacta cctttcttca   3240
aaaagtttga ttcttccgcc acttctggaa agacatacac tgctggtaca tcagatttca   3300
ataacttggc tcagaacatt gctttaggcg ccgatagatt cctgtctact gttaagttcc   3360
acgcatacac taacgggagt ctatcagaag agtacgatag atctaccggt atgagtactg   3420
gggctcgtga tttaacatgg tcccatgctt cattgatcac agtggcgtac gcaaaggccg   3480
gtagtcctgc agcttagtta attaaacagg ccccttttcc tttgtcgata tcatgtaatt   3540
agttatgtca cgcttacatt cacgccctcc tcccacatcc gctctaaccg aaaaggaagg   3600
agttagacaa cctgaagtct aggtccctat ttattttttt atagttatgt tagtattaag   3660
aacgttattt atatttcaaa tttttctttt ttttctgtac aaacgcgtgt acgcatgtaa   3720
cgggcagacg gccggccata acttcgtata atgtatgcta tacgaagtta tggcaacggt   3780
tcatcatctc atggatctgc acatgaacaa acaccagagt caaacgacgt tgaaattgag   3840
gctactgcgc caattgatga caatacagac gatgataaca aaccgaagtt atctgatgta   3900
gaaaaggatt agagatgcta agagatagtg atgatatttc ataaataatg taattctata   3960
tatgttaatt acctttttg cgaggcatat ttatggtgaa ggataagttt tgaccatcaa    4020
agaaggttaa tgtggctgtg gtttcagggt ccataaagct tttcaattca tcttttttt    4080
ttttgttctt ttttttgatt ccggtttctt tgaaattttt ttgattcggt aatctccgag   4140
cagaaggaag aacgaaggaa ggagcacaga cttagattgg tatatatacg catatgtggt   4200
gttgaagaaa catgaaattg cccagtattc ttaacccaac tgcacagaac aaaaacctgc   4260
aggaaacgaa gataaatcat gtcgaaagct acatataagg aacgtgctgc tactcatcct   4320
agtcctgttg ctgccaagct atttaatatc atgcacgaaa agcaaacaaa cttgtgtgct   4380
tcattggatg ttcgtaccac caaggaatta ctggagttag ttgaagcatt aggtcccaaa   4440
atttgtttac taaaaacaca tgtggatatc ttgactgatt tttccatgga gggcacagtt   4500
aagccgctaa aggcattatc cgccaagtac aattttttac tcttcgaaga cagaaaattt   4560
gctgacattg gtaatacagt caaattgcag tactctgcgg gtgtatacag aatagcagaa   4620
tgggcagaca ttacgaatgc acacggtgtg gtgggcccag gtattgttag cggtttgaag   4680
```

-continued caggcggcgg aagaagtaac aaaggaacct agaggccttt tgatgttagc agaattgtca 4740
tgcaagggct ccctagctac tggagaatat actaagggta ctgttgacat tgcgaagagc 4800
gacaaagatt ttgttatcgg ctttattgct caaagagaca tgggtggaag agatgaaggt 4860
tacgattggt tgattatgac acgc 4884

<210> SEQ ID NO 21
<211> LENGTH: 1790
<212> TYPE: DNA
<213> ORGANISM: Artificial Sequence
<220> FEATURE:
<223> OTHER INFORMATION: Integration construct

<400> SEQUENCE: 21
ggaagagctc ctactgcgcc aattgatgac aatacagacg atgataacaa accgaagtta 60
tctgatgtag aaaaggatta gagatgctaa gagatagtga tgatatttca taaataatgt 120
aattctatat atgttaatta cctttttttgc gaggcatatt tatggtgaag gataagtttt 180
gaccatcaaa gaaggttaat gtggctgtgg tttcagggtc cataaagctt ttcaattcat 240
cttttttttt ttgttctttt ttttgattcc ggtttctttg aaattttttt gattcggtaa 300
tctccgagca gaaggaagaa cgaaggaagg agcacagact tagattggta tatatacgca 360
tatgtggtgt tgaagaaaca tgaaattgcc cagtattctt aacccaactg cacagaacaa 420
aaacctgcag gaaacgaaga taaatcatgt cgaaagctac atataaggaa cgtgctgcta 480
ctcatcctag tcctgttgct gccaagctat ttaatatcat gcacgaaaag caaacaaact 540
tgtgtgcttc attggatgtt cgtaccacca aggaattact ggagttagtt gaagcattag 600
gtcccaaaat ttgtttacta aaaacacatg tggatatctt gactgatttt tccatggagg 660
gcacagttaa gccgctaaag gcattatccg ccaagtacaa tttttttactc ttcgaagaca 720 gaaaatttgc tgacattggt aatacagtca aattgcagta ctctgcgggt gtatacagaa 780
tagcagaatg ggcagacatt acgaatgcgc acggtgtggt gggcccaggt attgttagcg 840
gtttgaagca ggcggcggaa gaagtaacaa aggaacctag aggccttttg atgttagcag 900
aattgtcatg caagggctcc ctagctactg gagaatatac taagggtact gttgacattg 960
cgaagagcga caaagatttt gttatcggct ttattgctca aagagacatg ggtggaagag 1020
atgaaggtta cgattggttg attatgacac ccggtgtggg tttagatgac aagggagacg 1080
cattgggtca acagtataga gccgtggatg atgtggtctc tacaggatct gacattatta 1140
ttgttggaag aggactattt gcaaagggaa gggatgctaa ggtagagggt gaacgttaca 1200
gaaaagcagg ctgggaagca tatttgagaa gatgcggcca gcaaaactaa aaaactgtat 1260
tataagtaaa tgcatgtata ctaaactcac aaattagagc ttcaatttaa ttatatcagt 1320
tattacccgg gaatctcggt cgtaatgatt tttataatga cgaaaaaaaa aaattggaaa 1380
gaaaaagctt catggccttt ataaaaagga accatccaat acctcgccag aaccaagtaa 1440
cagtatttta cggggcacaa atcaagaaca ataagacagg actgtaaaga tggacgcatt 1500
gaactccaaa gaacaacaag agttccaaaa agtagtggaa caaaagcaaa tgaaggattt 1560
catgcgtttg ataacttcgt ataatgtatg ctatacgaag ttatgcggcc gccagcacgc 1620
agcacgctgt atttacgtat ttaattttat atatttgtgc atacactact agggaagact 1680
tgaaaaaaac ctaggaaatg aaaaaacgac acaggaagtc ccgtatttac tatttttttcc 1740 ttccttttga tggggcaggg cggaaataga ggataggata agcctactgc 1790

<210> SEQ ID NO 22
<211> LENGTH: 4474
<212> TYPE: DNA
<213> ORGANISM: Artificial Sequence
<220> FEATURE:
<223> OTHER INFORMATION: Rhizopus microsporus GA integration construct

<400> SEQUENCE: 22
gtgtttgtta attatactgt cgctgtaata tcttctcttc cattatcacc ggtcattcct 60
tgcaggggcg gtagtacccg gagaccctga acttttcttt ttttttttgc gaaattaaaa 120
agttcatttt caattcgaca atgagatcta caagccattg ttttatgttg atgagagcca 180
gcttaaagag ttctcgagat ctcccgagtt tatcattatc aatactgcca tttcaaagaa 240
tacgtaaata attaatagta gtgattttcc taactttatt tagtcaaaaa attggccttt 300
taattctgct gtaacccgta catgcccaaa ataggggggcg ggttacacag aatatataac 360
atcataggtg tctgggtgaa cagtttattc ctggcatcca ctaaatataa tggagcccgc 420
tttttttaag ctggcatcca gaaaaaaaaa gaatcccagc accaaaatat tgttttcttc 480
accaaccatc agttcatagg tccattctct tagcgcaact acacagaaca ggggcacaaa 540
caggcaaaaa acgggcacaa cctcaatgga gtgatgcaac ctgcttggag taaatgatga 600
cacaaggcaa ttgacctacg catgtatcta tctcattttc ttacaccttc tattaccttc 660
tgctctctct gatttggaaa aagctgaaaa aaaaggttga aaccagttcc ctgaaattat 720
tcccctattt gactaataag tatataaaga cggtaggtat tgattgtaat tctgtaaatc 780
tatttcttaa acttcttaaa ttctactttt atagttagtc tttttttttag tttaaaacac 840 caagaactta gtttcgaata aacacacata aacaaacaaa tctagaatga aacttatgaa 900
tccatctatg aaggcatacg ttttctttat cttaagctac ttctctttac tcgttagctc 960
agctgcggtg ccaacctctg ccgccgtaca agttgagtca tacaattatg acggtaccac 1020
tttttcaggt agaatattcg tcaaaaacat tgcctactca aaggtcgtaa cagttatcta 1080
ctccgatgga tcagataact ggaacaataa caacaacaaa gtttctgcag cttactcaga 1140
agcaatttct gggtctaact acgaatactg gacattctcc gcaaagttat ccggaattaa 1200
acagttttat gtcaaatacg aagtttctgg ttcaacatat tacgacaaca acggtaccaa 1260
aaactaccaa gtccaagcaa cctcagcgac atctacaaca gctactgcaa ccacaactac 1320
agctactggc acaacaacta cttctacagg tccaactagt actgcatccg tatcattccc 1380
taccggtaac tcaacaattt cttcctggat aaaaaatcaa gaggaaatca gccgttttgc 1440
tatgttgaga aatatcaatc cacctgggtc tgccacaggg ttcatagccg catctctgtc 1500
cacagccggc ccagattact attactcttg gactagagat tcagcactaa cagctaatgt 1560
gatcgcttac gaatacaaca caacattcac tggaaacacc acccttctta agtacttgaa 1620
agattacgtt acattttctg tcaaaagcca atctgtatct accgtttgta actgtctggg 1680
agaaccaaag ttcaacgctg atggtagttc ttttacaggt ccatggggca gaccacaaaa 1740
cgacggacca gcagagagag ctgttacttt tatgttgatt gctgacagct acttgactca 1800
aactaaggac gcatcctacg ttaccggtac attaaagcca gcaatcttca aagatcttga 1860
ttacgtagtt tctgtttggt ctaacggttg ctacgattta tgggaagagg ttaatggtgt 1920
tcatttctat actctcatgg tcatgagaaa gggtttgatc ttaggtgccg acttcgctgc 1980
tagaaatggt gactctagta gagcttcaac ctacaagcaa actgcatcaa caatggaatc 2040
aaagatcagt tctttttggt cagattctaa caactacgtc caagtttctc aatcagttac 2100

-continued

```
cgccggagtg tcaaaaaagg gactagatgt tagtacacta ttggcggcca acattggtag   2160
tctgcctgat ggctttttca ctccaggctc cgaaaagata ttggctacag cagtggcgtt   2220
agaaaatgca ttcgcatcct tgtacccaat taactctaac ctaccttctt acttgggtaa   2280
ctcaattgga agatatcctg aggatacata caacggtaat ggcaactctc aggggaatcc   2340
atggttcctt gccgtcaacg catacgcaga actttactac agagctatta aggaatggat   2400
tagtaatggc aaggtgacag tatccaatat ctcactacct ttcttcaaaa agtttgattc   2460
ttccgccact tctggaaaga catacactgc tggtacatca gatttcaata acttggctca   2520
gaacattgct ttaggcgccg atagattcct gtctactgtt aagttccacg catacactaa   2580
cgggagtcta tcagaagagt acgatagatc taccggtatg agtactgggg ctcgtgattt   2640
aacatggtcc catgcttcat tgatcacagt ggcgtacgca aaggccggta gtcctgcagc   2700
ttagttaatt aaacaggccc cttttccttt gtcgatatca tgtaattagt tatgtcacgc   2760
ttacattcac gccctcctcc cacatccgct ctaaccgaaa aggaaggagt tagacaacct   2820
gaagtctagg tccctattta ttttttata gttatgttag tattaagaac gttatttata   2880
tttcaaattt ttcttttttt tctgtacaaa cgcgtgtacg catgtaacgg gcagacggcc   2940
ggccataact tcgtataatg tatgctatac gaagttatcc ttacatcaca cccaatcccc   3000
cacaagtgat cccccacaca ccatagcttc aaaatgtttc tactcctttt ttactcttcc   3060
agattttctc ggactccgcg catcgccgta ccacttcaaa acacccaagc acagcatact   3120
aaatttcccc tctttcttcc tctagggtgg cgttaattac ccgtactaaa ggtttggaaa   3180
agaaaaaaga gaccgcctcg tttctttttc ttcgtcgaaa aaggcaataa aaatttttat   3240
cacgtttctt tttcttgaaa attttttttt ttgatttttt tctctttcga tgacctccca   3300
ttgatattta agttaataaa tggtcttcaa tttctcaagt ttcagtttcg tttttcttgt   3360
tctattacaa cttttttttac ttcttgctca ttagaaagaa agcatagcaa tctaatctaa   3420
gttttaatta caaaatgcca caatcctggg aagaattggc cgccgacaaa cgtgcccgtt   3480
tggctaaaac cattcctgac gaatggaagg ttcaaacttt gcctgccgaa gattccgtta   3540
ttgatttccc aaagaagtcc ggtattttgt ctgaggctga attgaagatt accgaagcct   3600
ctgctgctga tttggtctcc aagttggccg ctggtgagtt gacttctgtt gaagtcactt   3660
tggctttttg taagagagct gctattgctc aacaattaac caactgtgct cacgaattct   3720
tcccagatgc tgctttagct caagctagag aattagatga atactacgct aagcataaga   3780
gaccagttgg tccattacac ggtttaccaa tctctttaaa ggaccaattg cgtgttaagg   3840
gttacgaaac ctccatgggt tacatttcct ggttaaacaa atacgatgaa ggtgattccg   3900
tcttaaccac catgttgaga aaagctggtg ctgttttcta cgttaagacc tctgtcccac   3960
aaaccttgat ggtctgtgaa accgtcaaca acatcattgg tagaactgtc aatccaagaa   4020
acaaaaattg gtcctgtggt ggttcttctg gtggtgaagg tgctattgtt ggtattagag   4080
gtggtgttat tggtgtcggt actgacattg gtggttccat tagagtccca gctgctttca   4140
actttttata cggtttgaga ccatctcacg gtagattgcc atatgctaaa atggctaact   4200
ctatggaagg tcaagaaacc gttcactccg tcgttggtcc tatcactcac tccgtcgaag   4260
acttgagatt gttcaccaaa tctgtcttgg gtcaagaacc ttggaagtac gactctaagg   4320
tcatccccat gccatggaga caatctgaat ctgacatcat tgcctctaag attaagaatg   4380
gtggtttgaa cattggttat tacaatttcg acggtaacgt cttgccacac ccaccaattt   4440
tacgtggtgt cgaaactacc gttgccgctt tggc                                4474
```

<210> SEQ ID NO 23
<211> LENGTH: 1878
<212> TYPE: DNA
<213> ORGANISM: Artificial Sequence
<220> FEATURE:
<223> OTHER INFORMATION: Integration construct

<400> SEQUENCE: 23
gaagattacc gaagcctctg ctgctgattt ggtctccaag ttggccgctg gtgagttgac 60
ttctgttgaa gtcactttgg ctttttgtaa gagagctgct attgctcaac aattaaccaa 120
ctgtgctcac gaattcttcc cagatgctgc tttagctcaa gctagagaat tagatgaata 180
ctacgctaag cataagagac cagttggtcc attacacggt ttaccaatct ctttaaagga 240
ccaattgcgt gttaagggtt acgaaacctc catgggttac atttcctggt taaacaaata 300
cgatgaaggt gattccgtct taaccaccat gttgagaaaa gctggtgctg ttttctacgt 360
taagacctct gtcccacaaa ccttgatggt ctgtgaaacc gtcaacaaca tcattggtag 420
aactgtcaat ccaagaaaca aaaattggtc ctgtggtggt tcttctggtg gtgaaggtgc 480
tattgttggt attagaggtg gtgttattgg tgtcggtact gacattggtg gttccattag 540
agtcccagct gctttcaact ttttatacgg tttgagacca tctcacggta gattgccata 600
tgctaaaatg gctaactcta tggaaggtca agaaaccgtt cactccgtcg ttggtcctat 660
cactcactcc gtcgaagact tgagattgtt caccaaatct gtcttgggtc aagaaccttg 720
gaagtacgac tctaaggtca tcccaatgcc atggagacaa tctgaatctg acatcattgc 780
ctctaagatt aagaatggtg gtttgaacat tggttattac aatttcgacg gtaacgtctt 840
gccacaccca ccaattttac gtggtgtcga aactaccgtt gccgctttgg ccaaggctgg 900
tcacaccgtt actccatgga ctccatacaa gcatgatttc ggtcatgact tgatttccca 960
catctatgct gctgatggtt ctgccgacgt catgagagac atttctgcct ctggtgagcc 1020
agccatccct aacattaagg acttgttgaa cccaaatatt aaggctgtta acatgaacga 1080
attgtgggac actcatttac aaaagtggaa ctatcaaatg gaatacttgg aaaagtggcg 1140
tgaagctgaa gaaaaagctg gtaaggaatt ggacgctatt atcgctccaa ttactcctac 1200
cgccgctgtc agacacgatc aattcagata ctacggttac gcctccgtta ttaacttatt 1260
ggatttcacc tctgttgtcg tcccagtcac tttcgctgat aagaatattg ataagaagaa 1320
cgaatctttt aaagctgttt ccgaattgga tgctttggtt caagaagaat acgacccaga 1380
ggcttatcac ggtgctcctg ttgctgttca agttattggt agaagattgt ccgaagagag 1440
aactttggct atcgccgaag aagtcggtaa attgttgggt aacgtcgtca ctccataagg 1500
agattgataa gacttttcta gttgcatatc ttttatattt aaatcttatc tattagttaa 1560
ttttttgtaa tttatcctta tatatagtct ggttattcta aaatatcatt tcagtatcta 1620
aaaattcccc tctttttca gttatatctt aacaggcgat aacttcgtat aatgtatgct 1680
atacgaagtt atgcggccgc cagcacgcag cacgctgtat ttacgtattt aattttatat 1740
atttgtgcat acactactag ggaagacttg aaaaaaacct aggaaatgaa aaaacgacac 1800
aggaagtccc gtatttacta ttttttcctt ccttttgatg gggcagggcg gaaatagagg 1860
ataggataag cctactgc 1878

<210> SEQ ID NO 24
<211> LENGTH: 4827
<212> TYPE: DNA

-continued

<213> ORGANISM: Artificial Sequence
<220> FEATURE:
<223> OTHER INFORMATION: Rhizopus microsporus GA integration construct

<400> SEQUENCE: 24

```
ggccgctcca tggagggcac agttaagccg ctaaaggcat tatccgccaa gtacaatttt     60
ttactcttcg aagacagaaa atttgctgac attggtaata cagtcaaatt gcagtactct    120
gcgggtgtat acagaatagc agaatgggca gacattacga atgcacacgg tgtggtgggc    180
ccaggtattg ttagcggttt gaagcaggcg gcggaagaag taacaaagga acctagaggc    240
cttttgatgt tagcagaatt gtcatgcaag ggctccctag ctactggaga atatactaag    300
ggtactgttg acattgcgaa gagcgacaaa gattttgtta tcggctttat tgctcaaaga    360
gacatgggtg gaagagatga aggttacgat tggttgatta tgacacccgg tgtgggttta    420
gatgacaagg gagacgcatt gggtcaacag tatagaaccg tggatgatgt ggtctctaca    480
ggatctgaca ttattattgt tggaagagga ctatttgcaa agggaaggga tgctaaggta    540
gagggtgaac gttacagaaa agcaggctgg gaagcatatt tgagaagatg cggccagcaa    600
aactaaaaaa ctgtattata agtaaatgca tgtatactaa actcacaaat tagagcttca    660
atttaattat atcagttatt acccgggaat ctcggtcgta atgattttta taatgacgaa    720
aaaaaaaaaa ttggaaagaa aaagcttcat ggcctttata aaaaggaacc atccaatacc    780
tcgccagaac caagtaacag tattttacgg ggcacaaatc aagaacaata agacaggact    840
gtaaagatgg acgcattgaa ctccaaagaa caacaagagt tccaaaaagt agtggaacaa    900
aagcaaatga aggatttcat gcgtttgata acttcgtata atgtatgcta tacgaagtta    960
tctcgagggc cagaaaaagg aagtgtttcc ctccttcttg aattgatgtt accctcataa   1020
agcacgtggc ctcttatcga gaaagaaatt accgtcgctc gtgatttgtt tgcaaaaaga   1080
acaaaactga aaaaacccag acacgctcga cttcctgtct tcctgttgat tgcagcttcc   1140
aatttcgtca cacaacaagg tcctagcgac ggctcacagg ttttgtaaca agcaatcgaa   1200
ggttctggaa tggcgggaaa gggtttagta ccacatgcta tgatgcccac tgtgatctcc   1260
agagcaaagt tcgttcgatc gtactgttac tctctctctt tcaaacagaa ttgtccgaat   1320
cgtgtgacaa caacagcctg ttctcacaca ctcttttctt ctaaccaagg gggtggttta   1380
gtttagtaga acctcgtgaa acttacattt acatatatat aaacttgcat aaattggtca   1440
atgcaagaaa tacatatttg gtcttttcta attcgtagtt tttcaagttc ttagatgctt   1500
tctttttctc ttttttacag atcatcaagg aagtaattat ctacttttta caagtctaga   1560
atgaagctaa tgaacccatc tatgaaagct tatgtctttt tcatcttatc atacttctct   1620
ctcctagttt catctgccgc agtgcctaca tctgctgccg tccaagtgga aagttacaat   1680
tacgatggca ctaccttctc cggccgtatc ttcgtgaaaa acattgctta ctcaaaagtt   1740
gttacagtga tttactccga tggttctgat aattggaaca acaataacaa caaagtttca   1800
gcagcgtact ccgaagccat tagtggatct aactacgaat actggacttt ctccgcaaag   1860
ttgtctggta ttaagcaatt ctacgtaaag tacgaagttt caggttcaac atactacgat   1920
aacaatggta ctaaaaacta ccaggtacaa gccacaagcg ctacaagtac aactgccaca   1980
gctacaacta caactgctac agggacaaca actacatcaa ccggtccaac atcaaccgca   2040
tctgtctcct ttccaaccgg taacagtaca atatcatcat ggatcaaaaa ccaagaggaa   2100
atctcaagat ttgcaatgtt gagaaacatc aatccaccag ggtcagcgac tggtttcatc   2160
gccgcttcat tgtccaccgc tgggccagac tactattact cttggactag agactctgca   2220
```

-continued

```
ttgacagcaa acgttatagc ttacgaatac aacacaacct tcactggtaa cactaccttg   2280
ttgaagtatc ttaaagacta cgtcactttt agtgttaagt ctcaatctgt ttctaccgtc   2340
tgtaactgtt taggtgaacc aaagtttaat gcagatggct catcatttac tggtccatgg   2400
ggcagacctc aaaacgatgg accagcagaa agagcagtca cattcatgtt gatcgctgac   2460
tcatacttga cacaaactaa ggatgcttca tacgtgactg gaacactcaa gccagccata   2520
ttcaaagacc tggattatgt tgtttctgtg tggtctaatg gttgctacga tttgtgggag   2580
gaagttaatg gcgtacattt ctacacacta atggttatga gaaagggact aattcttggg   2640
gcagatttcg cagctagaaa tggtgattcc tcaagagcat ctacctacaa gcaaacagca   2700
tctacaatgg aatcaaagat cagctctttc tggtctgact ctaacaacta cgttcaagtt   2760
tcacaatctg tgactgctgg tgtaagtaaa aagggtttag atgtttctac tctgttagct   2820
gcaaacattg gttctttacc agatggcttc tttacaccag gatcagaaaa gattttggca   2880
actgccgttg ccttagagaa tgcattcgct tccctttacc ctattaactc taacttacct   2940
tcatatttgg gtaattcaat tggtagatat ccagaggaca catacaacgg aaacgggaat   3000
tcacagggca acccttggtt cttagccgta aacgcgtacg ccgagttata ctacagagcc   3060
attaaggaat ggatctcaaa tggtaaggta acagtctcta atatctctct tcctttcttt   3120
aaaaagttcg attctagcgc cactagcggc aagacctata cagccggaac aagtgatttc   3180
aataacctcg ctcagaacat agctcttgga gcagacagat ttctgtcaac tgttaaattt   3240
cacgcgtaca caaatggcag cttgtctgaa gagtacgatc gttccaccgg gatgagtact   3300
ggtgctagag atctaacctg gtcccatgca tctcttatca cagttgcata cgcaaaagct   3360
ggatctcctg ctgcgtaatt aattaattta ccagcttact atccttcttg aaaatatgca   3420
ctctatatct tttagttctt aattgcaaca catagatttg ctgtataacg aattttatgc   3480
tattttttta atttggagtt cggtgatgaa agtgtcacag cgaatttcct cacatgtagg   3540
gaccgaattg tttacaagtt ctctgtacca ccatggagac atcaaagatt gaaaatctat   3600
ggaaagatat ggacggtagc aacaagaata tagcacgagc cgcggagttc atttcgttac   3660
ttttgatatc gctcacaact attgcgaagc gcttcagtga aaaaatcata aggaaaagtt   3720
gtaaatatta ttggtagtat tcgtttggta aagtagaggg ggtaattttt cccctttatt   3780
ttgttcatac attcttaaat tgctttgcct ctccttttgg aaagctatac ttcggagcac   3840
tgttgagcga aggctcaggc cggcagcacg cagcacgctg tatttacgta tttaatttta   3900
tatatttgtg catacactac tagggaagac ttgaaaaaaa cctaggaaat gaaaaaaacga   3960
cacaggaagt cccgtattta ctattttttc cttccttttg atggggcagg gcggaaatag   4020
aggataggat aagcctactg cttagctgtt tccgtctcta cttcggtagt tgtctcaatt   4080
gtcgtttcag tattaccttt agagccgcta gacgatggtt gagctatttg ttgagggaaa   4140
actaagttca tgtaacacac gcataacccg attaaactca tgaatagctt gattgcagga   4200
ggctggtcca ttggagatgg tgccttattt tccttatagg caacgatgat gtcttcgtcg   4260
gtgttcaggt agtagtgtac actctgaatc agggagaacc aggcaatgaa cttgttcctc   4320
aagaaaatag cggccatagg catggattgg ttaaccacac cagatatgct tggtgtggca   4380
gaatatagtc cttttggtgg cgcaattttc ttgtacctgt ggtagaaagg gagcggttga   4440
actgttagta tatattggca atatcagcaa atttgaaaga aaattgtcgg tgaaaaacat   4500
acgaaacaca aaggtcgggc cttgcaacgt tattcaaagt cattgtttag ttgaggaggt   4560
```

-continued

```
agcagcggag tatatgtatt cctttttttt gcctatggat gttgtaccat gcccattctg   4620

ctcaagcttt tgttaaaatt atttttcagt attttttctt ccatgttgcg cgttacgaga   4680

acagaagcga cagataaccg caatcataca actagcgcta ctgcggggtg taaaaagcac   4740

aagaactaag ccaagatcac aacagttatc gataaaatag cagtgtttgc atggccattg   4800

agaaggacaa cattggcgtg cggcatg                                       4827


<210> SEQ ID NO 25
<211> LENGTH: 4684
<212> TYPE: DNA
<213> ORGANISM: Artificial Sequence
<220> FEATURE:
<223> OTHER INFORMATION: Rhizopus microsporus GA integration construct

<400> SEQUENCE: 25

ggccgcgaag gtgctattgt tggtattaga ggtggtgtta ttggtgtcgg tactgacatt     60

ggtggttcca ttagagtccc agctgctttc aactttttat acggtttgag accatctcac    120

ggtagattgc catatgctaa aatggctaac tctatggaag gtcaagaaac cgttcactcc    180

gtcgttggtc ctatcactca ctccgtcgaa gacttgagat tgttcaccaa atctgtcttg    240

ggtcaagaac cttggaagta cgactctaag gtcatcccaa tgccatggag acaatctgaa    300

tctgacatca ttgcctctaa gattaagaat ggtggtttga acattggtta ttacaatttc    360

gacggtaacg tcttgccaca cccaccaatt ttacgtggtg tcgaaactac cgttgccgct    420

ttggccaagg ctggtcacac cgttactcca tggactccat acaagcatga tttcggtcat    480

gacttgattt cccacatcta tgctgctgat ggttctgccg acgtcatgag agacatttct    540

gcctctggtg agccagccat ccctaacatt aaggacttgt tgaacccaaa tattaaggct    600

gttaacatga acgaattgtg ggacactcat ttacaaaagt ggaactatca aatggaatac    660

ttggaaaagt ggcgtgaagc tgaagaaaaa gctggtaagg aattggacgc tattatcgct    720

ccaattactc ctaccgccgc tgtcagacac gatcaattca gatactacgg ttacgcctcc    780

gttattaact tattggattt cacctctgtt gtcgtcccag tcactttcgc tgataagaat    840

attgataaga agaacgaatc ttttaaagct gtttccgaat tggatgcttt ggttcaagaa    900

gaatacgacc cagaggctta tcacggtgct cctgttgctg ttcaagttat tggtagaaga    960

ttgtccgaag agagaacttt ggctatcgcc gaagaagtcg gtaaattgtt gggtaacgtc   1020

gtcactccat aagcgaattt cttatgattt atgattttta ttattaaata agttataaaa   1080

aaaataagtg tatacaaatt ttaaagtgac tcttaggttt taaaacgaaa attcttattc   1140

ttgagtaact ctttcctgta ggtcaggttg ctttctcagg tatagcatga ggtcgctctt   1200

attgaccaca cctctaccgg catgccgagc aaatgcctgc aaatcgctcc ccatttcacc   1260

caattgtaga tatgctaact ccagcaatga gttgatgaat ctcggtgtgt attttatgtc   1320

ctcagaggac aacacataac ttcgtataat gtatgctata cgaagttatc tcgagggcca   1380

gaaaaaggaa gtgtttccct ccttcttgaa ttgatgttac cctcataaag cacgtggcct   1440

cttatcgaga aagaaattac cgtcgctcgt gatttgtttg caaaaagaac aaaactgaaa   1500

aaacccagac acgctcgact tcctgtcttc ctgttgattg cagcttccaa tttcgtcaca   1560

caacaaggtc ctagcgacgg ctcacaggtt ttgtaacaag caatcgaagg ttctggaatg   1620

gcgggaaagg gtttagtacc acatgctatg atgcccactg tgatctccag agcaaagttc   1680

gttcgatcgt actgttactc tctctctttc aaacagaatt gtccgaatcg tgtgacaaca   1740

acagcctgtt ctcacacact cttttcttct aaccaagggg gtggtttagt ttagtagaac   1800
```

-continued

```
ctcgtgaaac ttacatttac atatatataa acttgcataa attggtcaat gcaagaaata   1860
catatttggt cttttctaat tcgtagtttt tcaagttctt agatgctttc tttttctctt   1920
ttttacagat catcaaggaa gtaattatct actttttaca agtctagaat gaagctaatg   1980
aacccatcta tgaaagctta tgtctttttc atcttatcat acttctctct cctagtttca   2040
tctgccgcag tgcctacatc tgctgccgtc caagtggaaa gttacaatta cgatggcact   2100
accttctccg gccgtatctt cgtgaaaaac attgcttact caaaagttgt tacagtgatt   2160
tactccgatg gttctgataa ttggaacaac aataacaaca aagtttcagc agcgtactcc   2220
gaagccatta gtggatctaa ctacgaatac tggactttct ccgcaaagtt gtctggtatt   2280
aagcaattct acgtaaagta cgaagtttca ggttcaacat actacgataa caatggtact   2340
aaaaactacc aggtacaagc cacaagcgct acaagtacaa ctgccacagc tacaactaca   2400
actgctacag ggacaacaac tacatcaacc ggtccaacat caaccgcatc tgtctccttt   2460
ccaaccggta acagtacaat atcatcatgg atcaaaaacc aagaggaaat ctcaagattt   2520
gcaatgttga gaaacatcaa tccaccaggg tcagcgactg gtttcatcgc cgcttcattg   2580
tccaccgctg ggccagacta ctattactct tggactagag actctgcatt gacagcaaac   2640
gttatagctt acgaatacaa cacaaccttc actggtaaca ctaccttgtt gaagtatctt   2700
aaagactacg tcacttttag tgttaagtct caatctgttt ctaccgtctg taactgttta   2760
ggtgaaccaa agtttaatgc agatggctca tcatttactg gtccatgggg cagacctcaa   2820
aacgatggac cagcagaaag agcagtcaca ttcatgttga tcgctgactc atacttgaca   2880
caaactaagg atgcttcata cgtgactgga acactcaagc cagccatatt caaagacctg   2940
gattatgttg tttctgtgtg gtctaatggt tgctacgatt tgtgggagga agttaatggc   3000
gtacatttct acacactaat ggttatgaga aagggactaa ttcttggggc agatttcgca   3060
gctagaaatg gtgattcctc aagagcatct acctacaagc aaacagcatc tacaatggaa   3120
tcaaagatca gctctttctg gtctgactct aacaactacg ttcaagtttc acaatctgtg   3180
actgctggtg taagtaaaaa gggtttagat gtttctactc tgttagctgc aaacattggt   3240
tctttaccag atggcttctt tacaccagga tcagaaaaga ttttggcaac tgccgttgcc   3300
ttagagaatg cattcgcttc cctttaccct attaactcta acttaccttc atatttgggt   3360
aattcaattg gtagatatcc agaggacaca tacaacggaa acgggaattc acagggcaac   3420
ccttggttct tagccgtaaa cgcgtacgcc gagttatact acagagccat taaggaatgg   3480
atctcaaatg gtaaggtaac agtctctaat atctctcttc ctttctttaa aaagttcgat   3540
tctagcgcca ctagcggcaa gacctataca gccggaacaa gtgatttcaa taacctcgct   3600
cagaacatag ctcttggagc agacagattt ctgtcaactg ttaaatttca cgcgtacaca   3660
aatggcagct tgtctgaaga gtacgatcgt tccaccggga tgagtactgg tgctagagat   3720
ctaacctggt cccatgcatc tcttatcaca gttgcatacg caaaagctgg atctcctgct   3780
gcgtaattaa ttaatttacc agcttactat ccttcttgaa aatatgcact ctatatcttt   3840
tagttcttaa ttgcaacaca tagatttgct gtataacgaa ttttatgcta ttttttttaat   3900
ttggagttcg gtgatgaaag tgtcacagcg aatttcctca catgtaggga ccgaattgtt   3960
tacaagttct ctgtaccacc atggagacat caaagattga aaatctatgg aaagatatgg   4020
acggtagcaa caagaatata gcacgagccg cggagttcat ttcgttactt ttgatatcgc   4080
tcacaactat tgcgaagcgc ttcagtgaaa aaatcataag gaaaagttgt aaatattatt   4140
```

-continued

```
ggtagtattc gtttggtaaa gtagaggggg taatttttcc cctttatttt gttcatacat   4200

tcttaaattg ctttgcctct ccttttggaa agctatactt cggagcactg ttgagcgaag   4260

gctcaggccg gcagcacgca gcacgctgta tttacgtatt taattttata tatttgtgca   4320

tacactacta gggaagactt gaaaaaaacc taggaaatga aaaaacgaca caggaagtcc   4380

cgtatttact atttttttcct tccttttgat ggggcagggc ggaaatagag gataggataa   4440

gcctactgct tagctgtttc cgtctctact tcggtagttg tctcaattgt cgtttcagta   4500

ttacctttag agccgctaga cgatggttga gctatttgtt gagggaaaac taagttcatg   4560

taacacacgc ataacccgat taaactcatg aatagcttga ttgcaggagg ctggtccatt   4620

ggagatggtg ccttattttc cttataggca acgatgatgt cttcgtcggt gttcaggtag   4680

tagt                                                                4684
```

<210> SEQ ID NO 26
<211> LENGTH: 4909
<212> TYPE: DNA
<213> ORGANISM: Artificial Sequence
<220> FEATURE:
<223> OTHER INFORMATION: Rhizopus delemar GA integration construct

<400> SEQUENCE: 26

```
ctaaattcgg ccttgctcag agactcctgg attttggcta acaacgcagt cccttcgatg     60

catatagcta ggccacaaat tatgccaata acggtccatg ggttgatgtt ttcttgaatt    120

ctttcgtttt tcatgctatt tgcgtcttcc caagtcccag cgttccagta ttcatactgc    180

gcgttagagt ggtagccata agagccggca tattggtaat tttcagtatt aacgttagaa    240

cgtggtgaat acgatgtggt ccagccttgc ctcgttgtgt catatacgat ctttttcttt    300

gggtcacaaa gaatatcata tgcttgagag atgactttaa atctatgtag tttttcgctt    360

gatgttagca gcagcggtga tttactatca ctgttggtaa ccttttctga gctaaatatt    420

tgaatgttat cggaatggtc agggtggtac aattttacat aacgatgata ttttttttt     480

aacgacttct tgtccagttt aggatttcca gatccggcct ttggaatgcc aaaaatatca    540

tagggagttg gatctgccaa ctcaggccat tgttcatccc ttatcgtaag ttttctattg    600

ccatttttat cgttcgctgt agcatactta gctataaaag tgatttgtgg gggacacttt    660

tctacacatg ataagtgcca cttgaataaa aatgggtata cgaacttatg gtgtagcata    720

acaaatatat tgcaagtagt gacctatggt gtgtagatat acgtacagtt agttacgagc    780

ctaaagacac aacgtgtttg ttaattatac tgtcgctgta atatcttctc ttccattatc    840

accggtcatt ccttgcaggg gcggtagtac ccggagaccc tgaacttttc ttttttttt     900

tgcgaaatta aaaagttcat tttcaattcg acaatgagat ctacaagcca ttgttttatg    960

ttgatgagag ccagcttaaa gagttctcga gatctcccga gtttatcatt atcaatactg   1020

ccatttcaaa gaatacgtaa ataattaata gtagtgattt tcctaacttt atttagtcaa   1080

aaaattggcc ttttaattct gctgtaaccc gtacatgccc aaaatagggg gcgggttaca   1140

cagaatatat aacatcatag gtgtctgggt gaacagttta ttcctggcat ccactaaata   1200

taatggagcc cgcttttttt aagctggcat ccagaaaaaa aaagaatccc agcaccaaaa   1260

tattgtttc ttcaccaacc atcagttcat aggtccattc tcttagcgca actacacaga    1320

acaggggcac aaacaggcaa aaaacgggca caacctcaat ggagtgatgc aacctgcttg   1380

gagtaaatga tgacacaagg caattgacct acgcatgtat ctatctcatt ttcttacacc   1440

ttctattacc ttctgctctc tctgatttgg aaaaagctga aaaaaaaggt tgaaaccagt   1500
```

-continued

```
tccctgaaat tattccccta tttgactaat aagtatataa agacggtagg tattgattgt   1560
aattctgtaa atctatttct taaacttctt aaattctact tttatagtta gtcttttttt   1620
tagtttaaaa caccaagaac ttagtttcga ataaacacac ataaacaaac aaatctagaa   1680
tgcagttatt caacttacca cttaaggtat ctttctttct agtcttatct tacttttcat   1740
tgttagtatc agctgcctct ataccaagtt cagcatccgt acaactagat tcatacaatt   1800
acgacggttc aacattctca ggaaagatat acgtgaaaaa tattgcttac agcaaaaagg   1860
ttactgtgat ttacgcagat gggtcagaca actggaataa caatggaaac acaattgctg   1920
cttcctattc tgcccctatt tctggatcta actacgaata ctggactttt tcagcgagta   1980
taaacggaat taaggaattc tatatcaaat atgaagtctc tggtaagacc tactacgata   2040
acaacaactc cgcaaactac caagttagca catcaaagcc aaccacaaca actgctactg   2100
cgacaactac aaccgcacca agcacttcta ctacaacacc tcctagttca tctgagccag   2160
caactttccc aactggtaat tccactattt cttcttggat caaaaaacaa gagggtatct   2220
caagattcgc catgcttaga aatatcaatc ctccaggctc tgcaacagga ttcattgcag   2280
catctttatc aactgcgggg ccagactact actacgcctg gactagagat gcagctttga   2340
catcaaatgt gattgtttat gaatacaaca caactttgtc cggtaacaag acaatcttga   2400
acgtcttgaa ggattatgtg acattctctg tcaagactca atctacatca acagtttgta   2460
actgtctcgg cgaaccaaag ttcaaccctg atggtagtgg ttacactggt gcttggggta   2520
gaccacaaaa cgatggtcca gcagagagag ctacaacttt catcttgttt gctgactctt   2580
acctaacaca aaccaaggat gcaagctacg ttactggaac actaaagcct gcaatcttta   2640
aagacctgga ctatgttgta aacgtttggt caaatggctg cttcgatcta tgggaggaag   2700
tgaacggtgt tcacttctac acattaatgg tcatgagaaa gggactcttg cttggtgcag   2760
actttgctaa gagaaacggt gattctacac gtgcctccac ttactcctcc acagcttcaa   2820
ccattgccaa caaaatctct tctttctggg tcagctcaaa taactggatt caagtttctc   2880
aatcagttac tggtggtgtt tctaaaaagg gcctggatgt gtcaaccttg cttgctgcca   2940
atttgggcag tgttgatgac gggttcttca ccccaggttc tgaaaagatc ctcgccaccg   3000
cagttgccgt tgaagattca tttgctagtt tatacccaat caacaaaaat ctaccatcat   3060
accttggaaa ttcaatcggt agatatccag aggatacata caacggtaat ggaaactctc   3120
agggtaaccc ttggtttctt gcagttacag ggtacgctga actgtactac agagcgatta   3180
aggaatggat tggtaatggc ggcgtaactg ttagttctat ttctctacct ttcttcaaaa   3240
agttcgatag ttctgcaaca tctggtaaaa agtacacagt cggcacttcc gattttaaca   3300
atttagctca gaacatagca ctggcagctg atcgtttctt gagtacagtc caattgcatg   3360
cccataacaa cggtagtttg gctgaagagt ttgatagaac caccggttta tcaaccggcg   3420
ccagagattt aacatggtcc catgcgtctt tgataactgc ttcttacgcc aaggctgggg   3480
caccagctgc ctgattaatt aaacaggccc cttttccttt gtcgatatca tgtaattagt   3540
tatgtcacgc ttacattcac gccctcctcc cacatccgct ctaaccgaaa aggaaggagt   3600
tagacaacct gaagtctagg tccctattta ttttttttata gttatgttag tattaagaac   3660
gttatttata tttcaaattt ttcttttttt tctgtacaaa cgcgtgtacg catgtaacgg   3720
gcagacggcc ggccataact tcgtataatg tatgctatac gaagttatgg caacggttca   3780
tcatctcatg gatctgcaca tgaacaaaca ccagagtcaa acgacgttga aattgaggct   3840
```

-continued actgcgccaa ttgatgacaa tacagacgat gataacaaac cgaagttatc tgatgtagaa 3900
aaggattaga gatgctaaga gatagtgatg atatttcata aataatgtaa ttctatatat 3960
gttaattacc tttttgcga ggcatattta tggtgaagga taagttttga ccatcaaaga 4020
aggttaatgt ggctgtggtt tcagggtcca taaagctttt caattcatct ttttttttt 4080 tgttcttttt tttgattccg gtttctttga aattttttg attcggtaat ctccgagcag 4140
aaggaagaac gaaggaagga gcacagactt agattggtat atatacgcat atgtggtgtt 4200
gaagaaacat gaaattgccc agtattctta acccaactgc acagaacaaa aacctgcagg 4260
aaacgaagat aaatcatgtc gaaagctaca tataaggaac gtgctgctac tcatcctagt 4320
cctgttgctg ccaagctatt taatatcatg cacgaaaagc aaacaaactt gtgtgcttca 4380
ttggatgttc gtaccaccaa ggaattactg gagttagttg aagcattagg tcccaaaatt 4440
tgtttactaa aaacacatgt ggatatcttg actgattttt ccatggaggg cacagttaag 4500
ccgctaaagg cattatccgc caagtacaat tttttactct tcgaagacag aaaatttgct 4560
gacattggta atacagtcaa attgcagtac tctgcgggtg tatacagaat agcagaatgg 4620
gcagacatta cgaatgcaca cggtgtggtg ggcccaggta ttgttagcgg tttgaagcag 4680
gcggcggaag aagtaacaaa ggaacctaga ggcctttga tgttagcaga attgtcatgc 4740
aagggctccc tagctactgg agaatatact aagggtactg ttgacattgc gaagagcgac 4800
aaagattttg ttatcggctt tattgctcaa agagacatgg gtggaagaga tgaaggttac 4860
gattggttga ttatgacacg caggttacga ttggttgatt atgacacgc 4909

<210> SEQ ID NO 27
<211> LENGTH: 4824
<212> TYPE: DNA
<213> ORGANISM: Artificial Sequence
<220> FEATURE:
<223> OTHER INFORMATION: Rhizopus delemar GA integration construct

<400> SEQUENCE: 27
ggccgctcca tggagggcac agttaagccg ctaaaggcat tatccgccaa gtacaatttt 60
ttactcttcg aagacagaaa atttgctgac attggtaata cagtcaaatt gcagtactct 120
gcgggtgtat acagaatagc agaatgggca gacattacga atgcacacgg tgtggtgggc 180
ccaggtattg ttagcggttt gaagcaggcg gcggaagaag taacaaagga acctagaggc 240
cttttgatgt tagcagaatt gtcatgcaag ggctccctag ctactggaga atatactaag 300
ggtactgttg acattgcgaa gagcgacaaa gattttgtta tcggctttat tgctcaaaga 360
gacatgggtg gaagagatga aggttacgat tggttgatta tgacacccgg tgtgggttta 420
gatgacaagg gagacgcatt gggtcaacag tatagaaccg tggatgatgt ggtctctaca 480
ggatctgaca ttattattgt tggaagagga ctatttgcaa agggaaggga tgctaaggta 540
gagggtgaac gttacagaaa agcaggctgg gaagcatatt tgagaagatg cggccagcaa 600
aactaaaaaa ctgtattata agtaaatgca tgtatactaa actcacaaat tagagcttca 660
atttaattat atcagttatt acccgggaat ctcggtcgta atgattttta taatgacgaa 720
aaaaaaaaaa ttggaaagaa aaagcttcat ggcctttata aaaaggaacc atccaatacc 780
tcgccagaac caagtaacag tattttacgg ggcacaaatc aagaacaata agacaggact 840
gtaaagatgg acgcattgaa ctccaaagaa caacaagagt tccaaaaagt agtggaacaa 900
aagcaaatga aggatttcat gcgtttgata acttcgtata atgtatgcta tacgaagtta 960
tctcgagggc cagaaaaagg aagtgtttcc ctccttcttg aattgatgtt accctcataa 1020
agcacgtggc ctcttatcga gaaagaaatt accgtcgctc gtgatttgtt tgcaaaaaga 1080
acaaaactga aaaaacccag acacgctcga cttcctgtct tcctgttgat tgcagcttcc 1140
aatttcgtca cacaacaagg tcctagcgac ggctcacagg ttttgtaaca agcaatcgaa 1200
ggttctggaa tggcgggaaa gggtttagta ccacatgcta tgatgcccac tgtgatctcc 1260
agagcaaagt tcgttcgatc gtactgttac tctctctctt tcaaacagaa ttgtccgaat 1320
cgtgtgacaa caacagcctg ttctcacaca ctcttttctt ctaaccaagg gggtggttta 1380
gtttagtaga acctcgtgaa acttacattt acatatatat aaacttgcat aaattggtca 1440
atgcaagaaa tacatatttg gtcttttcta attcgtagtt tttcaagttc ttagatgctt 1500
tctttttctc tttttacag atcatcaagg aagtaattat ctacttttta caagtctaga 1560
atgcagctgt tcaacttgcc attaaaggtt tcattctttt tggtcctatc atactttagt 1620
ttgttggtgt cagccgcatc tattccatct tcagcatctg tacaattaga ctcctacaat 1680
tacgacggct ctacattcag cggaaagatt tacgtgaaaa atattgcgta cagcaaaaaa 1740
gtaactgtta tctatgccga cggatcagat aactggaaca acaatggaaa cactatcgct 1800
gccagttact ctgcaccaat ttcaggttct aactacgaat attggacatt ctcagcctcc 1860
atcaatggca ttaaggaatt ctacataaag tacgaagttt ccggtaagac ttactacgat 1920
aacaacaatt ctgcaaacta tcaagtatca acatcaaaac ctactaccac caccgccaca 1980
gctacaacta caactgcacc ttcaacatct accacaaccc caccatcttc tagcgaacca 2040
gctacattcc caactggcaa ttctactatt tctagttgga tcaaaaaaca agagggtatt 2100
tccagattcg caatgttgag aaacataaat ccaccaggat cagcaactgg attcatcgca 2160
gcttctttgt ccacagcggg gccagattac tactacgcat ggaccagaga tgctgctttg 2220
acaagtaacg ttattgttta cgaatacaat accactttgt ccggtaacaa gactattctt 2280
aacgtcctaa aggattacgt tacattctct gttaagactc agtctacatc cacagtctgc 2340
aattgtttgg gtgaaccaaa gttcaaccca gatggctctg gatacacagg tgcctggggt 2400
cgtccacaaa acgatgggcc tgccgagaga gccactacat ttatcctatt tgctgactca 2460
taccttacac aaacaaaaga tgcatcctac gtgactggaa cattaaagcc tgcaatcttc 2520
aaagacctgg attacgttgt caacgtgtgg tctaacggct gtttcgatct atgggaagag 2580
gttaacggcg tgcacttcta cactctaatg gtcatgagaa agggtctgtt gttaggtgca 2640
gattttgcta agagaaacgg tgattctaca cgtgcttcta cctactcctc aacagcatca 2700
actattgcga acaagatttc ttcattttgg gtttcaagta ataactggat acaagtatct 2760
caaagcgtta caggggtgt ctcaaaaaag ggtcttgatg tttctacatt actggctgct 2820
aatcttgggt ctgttgatga cggtttcttc acccctggtt ctgaaaagat cctcgctacc 2880
gccgtcgcgg ttgaggatag ttttgcttca ctctatccta taaacaaaaa ccttccttca 2940
tacttaggaa acagtatcgg tagataccca gaggatacat acaatggtaa tggcaattca 3000
cagggaaatc catggttcct tgctgttaca gggtacgcag aactttacta tagagctatt 3060
aaggaatgga tcggcaacgg cggtgtgaca gtttcctcaa tctcattgcc atttttcaaa 3120
aagtttgact ccagcgcgac atctggtaaa aagtatactg tggggacttc tgatttcaac 3180
aatttggctc aaaacattgc cttagctgcc gacagattct tatctaccgt acaactccat 3240
gcacataaca atggtagttt ggcagaggaa tttgatagaa ctacaggact ctctacaggt 3300
gcgagagatt taacttggtc acatgcaagt ttaattacag cctcttacgc aaaggctggt 3360

-continued

```
gctcctgctg cataattaat taatttacca gcttactatc cttcttgaaa atatgcactc   3420

tatatctttt agttcttaat tgcaacacat agatttgctg tataacgaat tttatgctat   3480

tttttaatt tggagttcgg tgatgaaagt gtcacagcga atttcctcac atgtagggac   3540

cgaattgttt acaagttctc tgtaccacca tggagacatc aaagattgaa aatctatgga   3600

aagatatgga cggtagcaac aagaatatag cacgagccgc ggagttcatt tcgttacttt   3660

tgatatcgct cacaactatt gcgaagcgct tcagtgaaaa aatcataagg aaaagttgta   3720

aatattattg gtagtattcg tttggtaaag tagagggggt aatttttccc ctttattttg   3780

ttcatacatt cttaaattgc tttgcctctc cttttggaaa gctatacttc ggagcactgt   3840

tgagcgaagg ctcaggccgg cagcacgcag cacgctgtat ttacgtattt aattttatat   3900

atttgtgcat acactactag ggaagacttg aaaaaaacct aggaaatgaa aaaacgacac   3960

aggaagtccc gtatttacta ttttttcctt ccttttgatg gggcagggcg gaaatagagg   4020

ataggataag cctactgctt agctgtttcc gtctctactt cggtagttgt ctcaattgtc   4080

gtttcagtat tacctttaga gccgctagac gatggttgag ctatttgttg agggaaaact   4140

aagttcatgt aacacacgca taacccgatt aaactcatga atagcttgat tgcaggaggc   4200

tggtccattg gagatggtgc cttattttcc ttataggcaa cgatgatgtc ttcgtcggtg   4260

ttcaggtagt agtgtacact ctgaatcagg gagaaccagg caatgaactt gttcctcaag   4320

aaaatagcgg ccataggcat ggattggtta accacaccag atatgcttgg tgtggcagaa   4380

tatagtcctt ttggtggcgc aattttcttg tacctgtggt agaaagggag cggttgaact   4440

gttagtatat attggcaata tcagcaaatt tgaaagaaaa ttgtcggtga aaaacatacg   4500

aaacacaaag gtcgggcctt gcaacgttat tcaaagtcat tgtttagttg aggaggtagc   4560

agcggagtat atgtattcct tttttttgcc tatggatgtt gtaccatgcc cattctgctc   4620

aagcttttgt taaaattatt tttcagtatt ttttcttcca tgttgcgcgt tacgagaaca   4680

gaagcgacag ataaccgcaa tcatacaact agcgctactg cggggtgtaa aaagcacaag   4740

aactaagcca agatcacaac agttatcgat aaaatagcag tgtttgcatg gccattgaga   4800

aggacaacat tggcgtgcgg catg                                           4824
```

<210> SEQ ID NO 28
<211> LENGTH: 5264
<212> TYPE: DNA
<213> ORGANISM: Artificial Sequence
<220> FEATURE:
<223> OTHER INFORMATION: Rhizopus delemar GA integration construct

<400> SEQUENCE: 28

```
ctaaattcgg ccttgctcag agactcctgg attttggcta acaacgcagt cccttcgatg     60

catatagcta ggccacaaat tatgccaata acggtccatg ggttgatgtt ttcttgaatt    120

ctttcgtttt tcatgctatt tgcgtcttcc caagtcccag cgttccagta ttcatactgc    180

gcgttagagt ggtagccata agagccggca tattggtaat tttcagtatt aacgttagaa    240

cgtggtgaat acgatgtggt ccagccttgc ctcgttgtgt catatacgat ctttttcttt    300

gggtcacaaa gaatatcata tgcttgagag atgactttaa atctatgtag tttttcgctt    360

gatgttagca gcagcggtga tttactatca ctgttggtaa ccttttctga gctaaatatt    420

tgaatgttat cggaatggtc agggtggtac aattttacat aacgatgata ttttttttt    480

aacgacttct tgtccagttt aggatttcca gatccggcct ttggaatgcc aaaaatatca    540

tagggagttg gatctgccaa ctcaggccat tgttcatccc ttatcgtaag ttttctattg    600
```

-continued

```
ccatttttat cgttcgctgt agcatactta gctataaaag tgatttgtgg gggacacttt    660
tctacacatg ataagtgcca cttgaataaa aatgggtata cgaacttatg gtgtagcata    720
acaaatatat tgcaagtagt gacctatggt gtgtagatat acgtacagtt agttacgagc    780
ctaaagacac aacgtgtttg ttaattatac tgtcgctgta atatcttctc ttccattatc    840
accggtcatt ccttgcaggg gcggtagtac ccggagaccc tgaacttttc tttttttttt    900
tgcgaaatta aaaagttcat tttcaattcg acaatgagat ctacaagcca ttgttttatg    960
ttgatgagag ccagcttaaa gagttctcga gatctcccga gtttatcatt atcaatactg   1020
ccatttcaaa gaatacgtaa ataattaata gtagtgattt tcctaacttt atttagtcaa   1080
aaaattggcc ttttaattct gctgtaaccc gtacatgccc aaaatagggg gcgggttaca   1140
cagaatatat aacatcatag gtgtctgggt gaacagttta ttcctggcat ccactaaata   1200
taatggagcc cgcttttttt aagctggcat ccagaaaaaa aaagaatccc agcaccaaaa   1260
tattgtttc ttcaccaacc atcagttcat aggtccattc tcttagcgca actacacaga   1320
acaggggcac aaacaggcaa aaaacgggca caacctcaat ggagtgatgc aacctgcttg   1380
gagtaaatga tgacacaagg caattgacct acgcatgtat ctatctcatt ttcttacacc   1440
ttctattacc ttctgctctc tctgatttgg aaaaagctga aaaaaaaggt tgaaaccagt   1500
tccctgaaat tattccccta tttgactaat aagtatataa agacggtagg tattgattgt   1560
aattctgtaa atctatttct taaacttctt aaattctact tttatagtta gtcttttttt   1620
tagtttaaaa caccaagaac ttagtttcga ataaacacac ataaacaaac aaatctagaa   1680
tgcagttatt caacttacca cttaaggtat ctttctttct agtcttatct tacttttcat   1740
tgttagtatc agctgcctct ataccaagtt cagcatccgt acaactagat tcatacaatt   1800
acgacggttc aacattctca ggaaagatat acgtgaaaaa tattgcttac agcaaaaagg   1860
ttactgtgat ttacgcagat gggtcagaca actggaataa caatggaaac acaattgctg   1920
cttcctattc tgcccctatt tctggatcta actacgaata ctggactttt tcagcgagta   1980
taaacggaat taaggaattc tatatcaaat atgaagtctc tggtaagacc tactacgata   2040
acaacaactc cgcaaactac caagttagca catcaaagcc aaccacaaca actgctactg   2100
cgacaactac aaccgcacca agcacttcta ctacaacacc tcctagttca tctgagccag   2160
caactttccc aactggtaat tccactattt cttcttggat caaaaaacaa gagggtatct   2220
caagattcgc catgcttaga aatatcaatc ctccaggctc tgcaacagga ttcattgcag   2280
catctttatc aactgcgggg ccagactact actacgcctg gactagagat gcagctttga   2340
catcaaatgt gattgtttat gaatacaaca caactttgtc cggtaacaag acaatcttga   2400
acgtcttgaa ggattatgtg acattctctg tcaagactca atctacatca acagtttgta   2460
actgtctcgg cgaaccaaag ttcaaccctg atggtagtgg ttacactggt gcttggggta   2520
gaccacaaaa cgatggtcca gcagagagag ctacaacttt catcttgttt gctgactctt   2580
acctaacaca aaccaaggat gcaagctacg ttactggaac actaaagcct gcaatcttta   2640
aagacctgga ctatgttgta aacgtttggt caaatggctg cttcgatcta tgggaggaag   2700
tgaacggtgt tcacttctac acattaatgg tcatgagaaa gggactcttg cttggtgcag   2760
actttgctaa gagaaacggt gattctacac gtgcctccac ttactcctcc acagcttcaa   2820
ccattgccaa caaaatctct tctttctggg tcagctcaaa taactggatt caagtttctc   2880
aatcagttac tggtggtgtt tctaaaaagg gcctggatgt gtcaaccttg cttgctgcca   2940
```

-continued

```
atttgggcag tgttgatgac gggttcttca ccccaggttc tgaaaagatc ctcgccaccg   3000
cagttgccgt tgaagattca tttgctagtt tatacccaat caacaaaaat ctaccatcat   3060
accttggaaa ttcaatcggt agatatccag aggatacata caacggtaat ggaaactctc   3120
agggtaaccc ttggtttctt gcagttacag ggtacgctga actgtactac agagcgatta   3180
aggaatggat tggtaatggc ggcgtaactg ttagttctat ttctctacct ttcttcaaaa   3240
agttcgatag ttctgcaaca tctggtaaaa agtacacagt cggcacttcc gattttaaca   3300
atttagctca gaacatagca ctggcagctg atcgtttctt gagtacagtc caattgcatg   3360
cccataacaa cggtagtttg gctgaagagt ttgatagaac caccggttta tcaaccggcg   3420
ccagagattt aacatggtcc catgcgtctt tgataactgc ttcttacgcc aaggctgggg   3480
caccagctgc ctgattaatt aaacaggccc cttttccttt gtcgatatca tgtaattagt   3540
tatgtcacgc ttacattcac gccctcctcc cacatccgct ctaaccgaaa aggaaggagt   3600
tagacaacct gaagtctagg tccctattta ttttttttata gttatgttag tattaagaac   3660
gttatttata tttcaaattt ttcttttttt tctgtacaaa cgcgtgtacg catgtaacgg   3720
gcagacggcc ggccataact tcgtataatg tatgctatac gaagttatcc ttacatcaca   3780
cccaatcccc cacaagtgat cccccacaca ccatagcttc aaaatgtttc tactcctttt   3840
ttactcttcc agattttctc ggactccgcg catcgccgta ccacttcaaa acacccaagc   3900
acagcatact aaatttcccc tctttcttcc tctagggtgg cgttaattac ccgtactaaa   3960
ggtttggaaa agaaaaaaga gaccgcctcg tttctttttc ttcgtcgaaa aaggcaataa   4020
aaatttttat cacgtttctt tttcttgaaa aatttttttt ttgatttttt tctctttcga   4080
tgacctccca ttgatattta agttaataaa tggtcttcaa tttctcaagt ttcagtttcg   4140
tttttcttgt tctattacaa cttttttttac ttcttgctca ttagaaagaa agcatagcaa   4200
tctaatctaa gttttaatta caaaatgcca caatcctggg aagaattggc cgccgacaaa   4260
cgtgcccgtt tggctaaaac cattcctgac gaatggaagg ttcaaacttt gcctgccgaa   4320
gattccgtta ttgatttccc aaagaagtcc ggtattttgt ctgaggctga attgaagatt   4380
accgaagcct ctgctgctga tttggtctcc aagttggccg ctggtgagtt gacttctgtt   4440
gaagtcactt tggctttttg taagagagct gctattgctc aacaattaac caactgtgct   4500
cacgaattct tcccagatgc tgctttagct caagctagag aattagatga atactacgct   4560
aagcataaga gaccagttgg tccattacac ggtttaccaa tctctttaaa ggaccaattg   4620
cgtgttaagg gttacgaaac ctccatgggt tacatttcct ggttaaacaa atacgatgaa   4680
ggtgattccg tcttaaccac catgttgaga aaagctggtg ctgttttcta cgttaagacc   4740
tctgtcccac aaaccttgat ggtctgtgaa accgtcaaca acatcattgg tagaactgtc   4800
aatccaagaa acaaaaattg gtcctgtggt ggttcttctg gtggtgaagg tgctattgtt   4860
ggtattagag gtggtgttat tggtgtcggt actgacattg gtggttccat tagagtccca   4920
gctgctttca actttttata cggtttgaga ccatctcacg gtagattgcc atatgctaaa   4980
atggctaact ctatggaagg tcaagaaacc gttcactccg tcgttggtcc tatcactcac   5040
tccgtcgaag acttgagatt gttcaccaaa tctgtcttgg gtcaagaacc ttggaagtac   5100
gactctaagg tcatccccat gccatggaga caatctgaat ctgacatcat tgcctctaag   5160
attaagaatg gtggtttgaa cattggttat tacaatttcg acggtaacgt cttgccacac   5220
ccaccaattt tacgtggtgt cgaaactacc gttgccgctt tggc                    5264
```

<210> SEQ ID NO 29
<211> LENGTH: 5026
<212> TYPE: DNA
<213> ORGANISM: Artificial Sequence
<220> FEATURE:
<223> OTHER INFORMATION: Rhizopus delemar GA integration construct

<400> SEQUENCE: 29
ggccgcgaag gtgctattgt tggtattaga ggtggtgtta ttggtgtcgg tactgacatt 60
ggtggttcca ttagagtccc agctgctttc aactttttat acggtttgag accatctcac 120
ggtagattgc catatgctaa aatggctaac tctatggaag gtcaagaaac cgttcactcc 180
gtcgttggtc ctatcactca ctccgtcgaa gacttgagat tgttcaccaa atctgtcttg 240
ggtcaagaac cttggaagta cgactctaag gtcatcccaa tgccatggag acaatctgaa 300
tctgacatca ttgcctctaa gattaagaat ggtggtttga acattggtta ttacaatttc 360
gacggtaacg tcttgccaca cccaccaatt ttacgtggtg tcgaaactac cgttgccgct 420
ttggccaagg ctggtcacac cgttactcca tggactccat acaagcatga tttcggtcat 480
gacttgattt cccacatcta tgctgctgat ggttctgccg acgtcatgag agacatttct 540
gcctctggtg agccagccat ccctaacatt aaggacttgt tgaacccaaa tattaaggct 600
gttaacatga acgaattgtg ggacactcat ttacaaaagt ggaactatca aatggaatac 660
ttggaaaagt ggcgtgaagc tgaagaaaaa gctggtaagg aattggacgc tattatcgct 720
ccaattactc ctaccgccgc tgtcagacac gatcaattca gatactacgg ttacgcctcc 780
gttattaact tattggattt cacctctgtt gtcgtcccag tcactttcgc tgataagaat 840
attgataaga agaacgaatc ttttaaagct gtttccgaat tggatgcttt ggttcaagaa 900
gaatacgacc cagaggctta tcacggtgct cctgttgctg ttcaagttat tggtagaaga 960
ttgtccgaag agagaacttt ggctatcgcc gaagaagtcg gtaaattgtt gggtaacgtc 1020
gtcactccat aagcgaattt cttatgattt atgattttta ttattaaata agttataaaa 1080
aaaataagtg tatacaaatt ttaaagtgac tcttaggttt taaaacgaaa attcttattc 1140
ttgagtaact ctttcctgta ggtcaggttg ctttctcagg tatagcatga ggtcgctctt 1200
attgaccaca cctctaccgg catgccgagc aaatgcctgc aaatcgctcc ccatttcacc 1260
caattgtaga tatgctaact ccagcaatga gttgatgaat ctcggtgtgt attttatgtc 1320
ctcagaggac aacacataac ttcgtataat gtatgctata cgaagttatc tcgagggcca 1380
gaaaaaggaa gtgtttccct ccttcttgaa ttgatgttac cctcataaag cacgtggcct 1440
cttatcgaga aagaaattac cgtcgctcgt gatttgtttg caaaaagaac aaaactgaaa 1500
aaacccagac acgctcgact tcctgtcttc ctgttgattg cagcttccaa tttcgtcaca 1560
caacaaggtc ctagcgacgg ctcacaggtt ttgtaacaag caatcgaagg ttctggaatg 1620
gcgggaaagg gtttagtacc acatgctatg atgcccactg tgatctccag agcaaagttc 1680
gttcgatcgt actgttactc tctctctttc aaacagaatt gtccgaatcg tgtgacaaca 1740
acagcctgtt ctcacacact cttttcttct aaccaagggg gtggtttagt ttagtagaac 1800
ctcgtgaaac ttacatttac atatatataa acttgcataa attggtcaat gcaagaaata 1860
catatttggt cttttctaat tcgtagtttt tcaagttctt agatgctttc tttttctctt 1920
ttttacagat catcaaggaa gtaattatct actttttaca agtctagaat gcagctgttc 1980
aacttgccat taaaggtttc attctttttg gtcctatcat actttagttt gttggtgtca 2040
gccgcatcta ttccatcttc agcatctgta caattagact cctacaatta cgacggctct 2100

-continued

```
acattcagcg gaaagattta cgtgaaaaat attgcgtaca gcaaaaaagt aactgttatc   2160

tatgccgacg gatcagataa ctggaacaac aatggaaaca ctatcgctgc cagttactct   2220

gcaccaattt caggttctaa ctacgaatat tggacattct cagcctccat caatggcatt   2280

aaggaattct acataaagta cgaagtttcc ggtaagactt actacgataa caacaattct   2340

gcaaactatc aagtatcaac atcaaaacct actaccacca ccgccacagc tacaactaca   2400

actgcacctt caacatctac cacaacccca ccatcttcta gcgaaccagc tacattccca   2460

actggcaatt ctactatttc tagttggatc aaaaaacaag agggtatttc cagattcgca   2520

atgttgagaa acataaatcc accaggatca gcaactggat tcatcgcagc ttctttgtcc   2580

acagcggggc cagattacta ctacgcatgg accagagatg ctgctttgac aagtaacgtt   2640

attgtttacg aatacaatac cactttgtcc ggtaacaaga ctattcttaa cgtcctaaag   2700

gattacgtta cattctctgt taagactcag tctacatcca cagtctgcaa ttgtttgggt   2760

gaaccaaagt tcaacccaga tggctctgga tacacaggtg cctggggtcg tccacaaaac   2820

gatgggcctg ccgagagagc cactacattt atcctatttg ctgactcata ccttacacaa   2880

acaaaagatg catcctacgt gactggaaca ttaaagcctg caatcttcaa agacctggat   2940

tacgttgtca acgtgtggtc taacggctgt ttcgatctat gggaagaggt taacggcgtg   3000

cacttctaca ctctaatggt catgagaaag ggtctgttgt taggtgcaga ttttgctaag   3060

agaaacggtg attctacacg tgcttctacc tactcctcaa cagcatcaac tattgcgaac   3120

aagatttctt cattttgggt ttcaagtaat aactggatac aagtatctca aagcgttaca   3180

gggggtgtct caaaaaaggg tcttgatgtt tctacattac tggctgctaa tcttgggtct   3240

gttgatgacg gtttcttcac ccctggttct gaaaagatcc tcgctaccgc cgtcgcggtt   3300

gaggatagtt ttgcttcact ctatcctata aacaaaaacc ttccttcata cttaggaaac   3360

agtatcggta gatacccaga ggatacatac aatggtaatg gcaattcaca gggaaatcca   3420

tggttccttg ctgttacagg gtacgcagaa ctttactata gagctattaa ggaatggatc   3480

ggcaacggcg gtgtgacagt ttcctcaatc tcattgccat tttcaaaaa gtttgactcc   3540

agcgcgacat ctggtaaaaa gtatactgtg ggacttctg atttcaacaa tttggctcaa   3600

aacattgcct tagctgccga cagattctta tctaccgtac aactccatgc acataacaat   3660

ggtagtttgg cagaggaatt tgatagaact acaggactct ctacaggtgc gagagattta   3720

acttggtcac atgcaagttt aattacagcc tcttacgcaa aggctggtgc tcctgctgca   3780

taattaatta atttaccagc ttactatcct tcttgaaaat atgcactcta tatcttttag   3840

ttcttaattg caacacatag atttgctgta taacgaattt tatgctattt ttttaatttg   3900

gagttcggtg atgaaagtgt cacagcgaat ttcctcacat gtagggaccg aattgtttac   3960

aagttctctg taccaccatg gagacatcaa agattgaaaa tctatggaaa gatatggacg   4020

gtagcaacaa gaatatagca cgagccgcgg agttcatttc gttacttttg atatcgctca   4080

caactattgc gaagcgcttc agtgaaaaaa tcataaggaa aagttgtaaa tattattggt   4140

agtattcgtt tggtaaagta gagggggtaa tttttcccct ttattttgtt catacattct   4200

taaattgctt tgcctctcct tttggaaagc tatacttcgg agcactgttg agcgaaggct   4260

caggccggca gcacgcagca cgctgtattt acgtatttaa ttttatatat ttgtgcatac   4320

actactaggg aagacttgaa aaaaacctag gaaatgaaaa aacgacacag gaagtcccgt   4380

atttactatt ttttccttcc ttttgatggg gcagggcgga aatagaggat aggataagcc   4440

tactgcttag ctgtttccgt ctctacttcg gtagttgtct caattgtcgt ttcagtatta   4500
```

-continued

```
cctttagagc cgctagacga tggttgagct atttgttgag ggaaaactaa gttcatgtaa   4560

cacacgcata acccgattaa actcatgaat agcttgattg caggaggctg gtccattgga   4620

gatggtgcct tattttcctt ataggcaacg atgatgtctt cgtcggtgtt caggtagtag   4680

tgtacactct gaatcaggga gaaccaggca atgaacttgt tcctcaagaa aatagcggcc   4740

ataggcatgg attggttaac cacaccagat atgcttggtg tggcagaata tagtcctttt   4800

ggtggcgcaa ttttcttgta cctgtggtag aaagggagcg gttgaactgt tagtatatat   4860

tggcaatatc agcaaatttg aaagaaaatt gtcggtgaaa aacatacgaa acacaaaggt   4920

cgggccttgc aacgttattc aaagtcattg tttagttgag gaggtagcag cggagtatat   4980

gtattccttt tttttgccta tggatgttgt accatgccca ttctga                  5026
```

GLUCOAMYLASE ENGINEERED YEAST AND FERMENTATION METHODS

CROSS-REFERENCE TO RELATED APPLICATIONS

This application is a Continuation of U.S. patent application Ser. No. 16/976,550, filed Aug. 28, 2020, which is a national phase application of PCT/US2019/019805, filed Feb. 27, 2019, which claims the benefit of U.S. Provisional Patent Application No. 62/636,716, filed Feb. 28, 2018, each of which is hereby incorporated by reference herein in its entirety.

SEQUENCE LISTING

The entire contents of the ASCII text file entitled "N00570_Sequence_Listing_ST25.txt," created on Feb. 27, 2019, and having a size of 123 kilobytes is incorporated herein by reference.

FIELD OF THE INVENTION

The current invention relates to yeast engineered with exogenous glucoamylase nucleic acids and fermentations methods for producing a bioproduct such as ethanol.

BACKGROUND

Many fermentation feedstocks are derived from plant sources (e.g., corn mash) where the carbohydrates are predominantly in the form of starch polymers. The starch polymers in such feedstocks must be treated to low molecular weight sugars that can be consumed by the yeast and used for growth and bioproduct production. Typical treatments include acid and/or enzymatic hydrolysis where the polymer chain is hydrolyzed to generate the sugars that can be used by the yeast. Starch degrading enzymes such as alpha amylases and glucoamylases can be added to convert the polymer to simple sugars. However, such enzyme additions can add significant cost and complexity to the fermentation process.

Heterologous expression and functionality of enzymes in yeast to aid in starch hydrolysis can be challenging, as it is difficult to know if the nucleic acid will be expressed properly and a functional enzyme will form, and if an active form of the enzyme will be secreted from the cell. It is also challenging to engineer yeast for growth and bioproduct production at non-optimal conditions, such as high temperatures, and in high bioproduct titers. For example, while ethanol production by fermentation is a well know industrial process, maintaining ethanol rates, titers, and yields while at the same time engineering the yeast to reduce reliance on supplemental enzymes, growth under non-optimal conditions (e.g., temperature), and minimizing by-product formation can be technically difficult. Increased ethanol concentration and accumulation of undesirable byproducts can also be detrimental to cell health.

SUMMARY OF THE INVENTION

The invention relates to engineered yeast and fermentation methods, wherein the engineered yeast are able to secrete a heterologous glucoamylase (GA) into a fermentation medium and provide glucoamylase activity (E.C. 3.2.1.3) on a fermentation substrate. The invention also relates to methods of for producing bio-derived products, such as ethanol, via fermentation using the engineered yeast.

In one aspect, experimental studies associated with the current application identified fungal glucoamylase genes that, when introduced exogenously into yeast, allowed it to grow well on feedstocks containing low glucose and high starch amounts, and produce high levels of bioproduct. The results indicated that the engineered yeast were able to secrete glucoamylase into the fermentation medium and that the glucoamylase was enzymatically active towards the starch to generate sufficient glucose for growth and bioproduct production. Other benefits associated with the disclosure include improved fermentation and bioproduct production at elevated fermentation temperatures. Yet other benefits associated with the disclosure include reduced amounts of glucose at the end of the fermentation period.

In one aspect, the invention provides an engineered yeast comprising an exogenous nucleic acid encoding a glucoamylase comprising a sequence having 81% or greater sequence identity to SEQ ID NO:1 (*Rhizopus microsporus* glucoamylase). In an embodiment, the engineered yeast is capable of producing ethanol at a rate of 1.0, 1.5, 2.0, 2.5, 3.0, 3.5, 4.0, 4.5, or 5.0 g/L*h or greater during a fermentation process. In another embodiment, the engineered yeast is capable of producing (a) at least 70 g/kg of ethanol in a fermentation medium made from a glucose polymer-containing feedstock having (i) a DE of about 50 or less. In another embodiment, the engineered yeast is capable of producing (a) 90 g/kg or greater, 120 g/kg or greater, 130 g/kg or greater, or 140 g/kg or greater of ethanol in a fermentation medium made from a glucose polymer-containing feedstock having (i) a DE of about 30. In embodiments, the amount of 70 g/kg of ethanol may be produced within 48 hours of inoculation in a fermentation medium with the feedstock. In embodiments, the glucose concentration may not be greater than 5% (wt) in the fermentation medium at the beginning (inoculation) of the fermentation process. In embodiments, the feedstock may provide an amount of glucose polymer-containing feedstock sufficient to produce 70 g/kg ethanol, for example about 20 wt % glucose-polymer feedstock in the medium. In embodiments, the feedstock may have one or more of the following properties: the feedstock is a starch hydrolysate; the glucose-polymer has predominantly α-1,4 linkages; the feedstock substantially excludes cellulosic materials (e.g., less than 20%, 15%, or 10% of cellulosic material).

In an embodiment, the yeast is capable of producing (a) at least 70 g/kg of ethanol in a fermentation medium made from corn mash having a DE of 30±2, wherein fermentation medium comprises about 32% dry weight of corn, and a pH 5.8, 35 ppm CaCl, 1900 ppm urea, 5 ppm ampicillin, wherein the staring yeast concentration is 0.1 (OD600), and fermentation is carried out at 48 hrs at 30° C. with agitation. In more specific embodiments that engineered yeast comprise a glucoamylase having 81%, 82%, 83%, 84%, 85%, 90%, 95%, 96%, 97%, 98%, or 99% or greater sequence identity to SEQ ID NO:1.

In a related embodiment, the invention provides a fermentation method for producing a bioproduct. The method comprises forming a fermentation medium from a glucose polymer-containing feedstock, and then fermenting the fermentation medium using an engineered yeast comprising an exogenous nucleic acid encoding a glucoamylase comprising a sequence having 81% or greater sequence identity to SEQ ID NO:1. Fermentation is carried out over a period to produces the bioproduct, such as ethanol.

In more specific embodiments, ethanol is produced during the fermentation period to an amount of 70 g/kg or greater, 90 g/kg or greater, 120 g/kg or greater, 130 g/kg or greater, or 140 g/kg or greater, in the fermentation medium. In some embodiments, in the fermentation method, the glucose polymer-containing feedstock has a dextrose equivalent (DE) that is not greater than 50. In some embodiments, glucose is not greater than 5 wt % of solids materials in the feedstock. Optionally, supplemental glucoamylase can be introduced into the fermentation methods to increase bioproduct titers.

In some embodiments using the engineered yeast with glucoamylase having 81% or greater sequence identity to SEQ ID NO:1 fermenting is carried out at a temperature in the range of 31° C. to 35° C. for most or all of a fermentation period.

In some embodiments using the engineered yeast with glucoamylase having 81% or greater sequence identity to SEQ ID NO:1, at the end of the fermentation period the glucose concentration in the fermentation medium of not greater than 1.0 g/L.

In another aspect, the invention provides an engineered yeast comprising an exogenous nucleic acid encoding a glucoamylase comprising a sequence having 97% or greater, or 98% or greater sequence identity to SEQ ID NO:4 (*Rhizopus delemar* glucoamylase). In an embodiment, the engineered yeast is capable of producing ethanol at a rate of 1.0, 1.5, 2.0, 2.5, 3.0, 3.5, 4.0, 4.5, or 5.0 g/L*h or greater during a fermentation process. In another embodiment, the engineered yeast is capable of producing (a) at least 70 g/kg of ethanol in a fermentation medium made from a glucose polymer-containing feedstock having (i) a DE of about 30. In embodiments, the amount of 70 g/kg of ethanol may be produced within 48 hours of inoculation in a fermentation medium with the feedstock having. In embodiments, the glucose concentration may not be greater than 5% (wt) in the fermentation medium at the beginning (inoculation) of the fermentation process. In embodiments, the feedstock may provide an amount of glucose polymer-containing feedstock sufficient to produce 70 g/kg ethanol, for example about 20 wt % glucose-polymer feedstock in the medium. In embodiments, the feedstock may have one or more of the following properties: the feedstock is a starch hydrolysate; the glucose-polymer has predominantly α-1,4 linkages; the feedstock substantially excludes cellulosic materials (e.g., less than 20%, 15%, or 10% of cellulosic material).

In a related embodiment, the invention provides a fermentation method for producing a bioproduct. The method comprises forming a fermentation medium from a glucose polymer-containing feedstock, and then fermenting the fermentation medium using an engineered yeast comprising an exogenous nucleic acid encoding a glucoamylase comprising a sequence having 97% or greater sequence identity to SEQ ID NO:4. Fermentation is carried out over a period to produces the bioproduct, such as ethanol.

In more specific embodiments of any of the preceding fermentation, ethanol is produced during the fermentation period to an amount of 70 g/kg or greater, 90 g/kg or greater, 120 g/kg or greater, 130 g/kg or greater, or 140 g/kg or greater, in the fermentation medium. In some embodiments, in the fermentation method, the glucose polymer-containing feedstock has a dextrose equivalent (DE) that is about 30. In some embodiments, glucose is not greater than 5 wt % of solids materials in the feedstock. Optionally, supplemental glucoamylase can be introduced into the fermentation methods to increase bioproduct titers.

In some embodiments using the engineered yeast with glucoamylase having 97% or greater or 98% or greater sequence identity to SEQ ID NO:4, fermenting is carried out at a temperature in the range of 31° C. to 35° C. for most or all of a fermentation period.

In some embodiments using the engineered yeast with glucoamylase having 97% or greater sequence identity to SEQ ID NO:4, at the end of the fermentation period the glucose concentration in the fermentation medium is not greater than 2.0 L, or not greater than 1.0 g/L.

In more specific embodiments of any of the preceding yeast embodiments, the engineered yeast is capable of producing 90 g/kg or greater, 120 g/kg or greater, 130 g/kg or greater, or 140 g/kg or greater of ethanol in a fermentation medium made from a glucose polymer-containing feedstock having (i) a DE of about 30.

BRIEF DESCRIPTION OF THE FIGURE

FIG. 1 shows an alignment of SEQ ID NO:1 to *Rhizopus oryzae* GA, showing the signal sequence (1-25) and starching binding domain (26-131).

DETAILED DESCRIPTION

The aspects of the present invention described below are not intended to be exhaustive or to limit the invention to the precise forms disclosed in the following detailed description. Rather a purpose of the aspects chosen and described is so that the appreciation and understanding by others skilled in the art of the principles and practices of the present invention can be facilitated.

An aspect of the invention relates to engineered yeast that expresses a glucoamylase comprising a sequence having 80%, 81%, 82%, 83%, 84%, 85%, 90%, 95%, 96%, 97%, 98%, or 99% or greater sequence identity to SEQ ID NO:1 (*Rhizopus microsporus* glucoamylase (GA)). Another aspect of the invention relates to engineered yeast that expresses a glucoamylase comprising a sequence having 97%, 98%, or 99% or greater sequence identity to SEQ ID NO:4 (*Rhizopus delemar* glucoamylase (GA)). Engineered yeast of the disclosure are able express and provide glucoamylase enzyme in the culture medium, and the glucoamylases are enzymatically active on glucose polymer substrates such as starch from various plant sources. The glucoamylase activity within the medium can generate mono and disaccharide sugars which can be consumed by the yeast and can be used as a carbon source for the production of a target compound, such as ethanol.

In embodiments of the disclosure, a fermentation medium can be prepared from a feedstock having glucose polymer and minimal glucose. For example, a fermentation medium can be prepared from a starch-containing feedstock having a DE (dextrose equivalent) of 70 or less, 60 or less, 50 or less, 40 or less, 30 or less, 20 or less, 15 or less, 10 or less, or 5 or less. Dextrose equivalent (DE) is a measure of the amount of reducing sugars present in a material (e.g., a sugar product or a starch-containing feedstock), relative to dextrose (a.k.a. glucose), expressed as a percentage on a dry basis. For example, a maltodextrin with a DE of 10 would have 10% of the reducing power of dextrose (which has a DE of 100). A fermentation medium can be prepared from a starch-containing feedstock that does not have a glucose amount that is greater than about 5% wt., or greater than about 4% wt., or greater than about 3% wt., or greater than about 2% wt., or greater than about 1% wt., per total solids in the feedstock. In some fermentation methods the low glucose-containing starch feed stock is added periodically or continuously throughout the fermentation period. The glucoamylases produced by the engineered yeast can be enzymatically active against the starch in the medium and generate glucose which can be used by the yeast for growth and generation of bioproduct. Optionally, the fermentation method can include supplementing the medium with purified glucoamylase, such as glucoamylase obtained from a commercial source, which can further drive enzymatic hydrolysis of the starch and increase growth and titers of bioproduct.

For example, without any commercial glucoamylase enzyme supplementation and using a low glucose feedstock, the engineered yeast of the disclosure can generate an amount of ethanol of about 70 g/kg or greater, such as an amount in the range of about 70 g/kg to about 115 g/kg, about 75 g/kg to about 115 g/kg, about 80 g/kg to about 115 g/kg, about 85 g/kg to about 115 g/kg, about 90 g/kg to about 115 g/kg, about 95 g/kg to about 115 g/kg, about 100 g/kg to about 115 g/kg, or about 105 g/kg to about 115 g/kg of ethanol in the fermentation medium. In embodiments wherein supplemental glucoamylase is added to the medium, greater amounts of ethanol can be produced, such as an amount of 110 g/kg or greater, or 125 g/kg or greater, or 140 g/kg or greater, in the fermentation medium.

In further embodiments, yeast engineered with glucoamylases of the disclosure can exhibit excellent fermentation performance at temperatures greater than standardly used in fermentations (i.e., fermentations at 30° C. using *Saccharomyces cerevisiae* as a host organism). For example, in some embodiments using the engineered yeast of the disclosure, fermenting is carried out at a temperature in the range of 31° C. to 35° C., or 32° C. to 34° C., for most or all of a fermentation period. Even at the higher temperatures, the engineered yeast are able to generate glucoamylase activity in the medium, and promote excellent cell growth and bioproduct production.

In further embodiments, following a period of fermentation, yeast engineered with of glucoamylases of the disclosure can provide a desirable final fermentation medium with high levels of bioproduct and low levels of byproduct. In particular, the final fermentation medium can have high levels of ethanol (e.g., 70 g/kg or greater), under stressful fermentation conditions, such as where low levels of glucose, such as 1.0 g/kg, may be present.

The term "exogenous" as used herein, means that a molecule, such as a nucleic acid, or an activity, such as an enzyme activity, is introduced into the host organism. An exogenous nucleic acid can be introduced in to the host organism by well-known techniques and can be maintained external to the hosts chromosomal material (e.g., maintained on a non-integrating vector), or can be integrated into the host's chromosome, such as by a recombination event. An exogenous nucleic acid can encode an enzyme, or portion thereof, that is either homologous or heterologous to the host organism.

The term "heterologous" refers to a molecule or activity that is from a source that is different than the referenced molecule or organism. Accordingly, a gene or protein that is heterologous to a referenced organism is a gene or protein not found in that organism. For example, a specific glucoamylase gene found in a first fungal species and exogenously introduced into a second fugal species that is the host organism is "heterologous" to the second fungal organism.

The following SEQ ID NOs are associated with the fungal GA amino acid or protein sequences: SEQ ID NO:1: *Rhizopus microsporus* GA amino acid sequence; SEQ ID NO:2: *Rhizopus microsporus* GA nucleic acid sequence #1; SEQ ID NO:3: *Rhizopus microsporus* GA nucleic acid sequence #2; SEQ ID NO:4: *Rhizopus delemar* GA amino acid sequence; SEQ ID NO:5: *Rhizopus delemar* GA nucleic acid sequence #1; and SEQ ID NO:6: *Rhizopus delemar* GA nucleic acid sequence #2.

Table 1 is a table of sequence identity (global protein alignment) between the *Rhizopus microsporus* GA amino acid sequence and GA sequence of other known GAs. The reference molecule is *Rhizopus microsporus* GA, and scoring matrix was BLOSUM 62.

TABLE 1

| GA sequence | Start | End | # Match | # Non-match | % Match |
|---|---|---|---|---|---|
| *Rhizopus microsporus* | 1 | 605 | — | — | 100 |
| *Rhizopus delemar* | 1 | 604 | 488 | 117 | 80 |
| *Rhizopus oryzae* | 1 | 604 | 485 | 120 | 80 |
| *Mucor ambiguus* | 1 | 609 | 416 | 194 | 68 |
| *Mucor circenello* | 1 | 609 | 415 | 198 | 67 |
| *Choanephora cucurbitarum* | 1 | 622 | 402 | 222 | 64 |
| *Phycomyces blakesleeanus* | 1 | 598 | 369 | 243 | 60 |
| *Arthrobotrys oligospora* | 1 | 621 | 204 | 441 | 31 |

*Rhizopus microsporus* GA and *Rhizopus delemar* GA are members of the glucoamylase enzyme family (E.C. 3.2.1.3) and are amylolytic enzymes that hydrolyze 1,4-linked a-D-glucosyl residues successively from the nonreducing end of oligo- and polysaccharide chains with the release of D-glucose. Alternative names for glucoamylases include amyloglucosidase; γ-amylase; lysosomal α-glucosidase; acid maltase; exo-1,4-α-glucosidase; glucose amylase; γ-1,4-glucan glucohydrolase; acid maltase; 1,4-α-D-glucan glucohydrolase.

Glucoamylases such as *Rhizopus microsporus* GA and *Rhizopus delemar* GA can also cleave α-1,6 bonds on amylopectin branching points. As used herein, the term "amylolytic activity" pertains to these enzymatic mechanisms.

Engineered yeast of the disclosure can include variant(s) of the natural sequences of the *Rhizopus microsporus* GA and *Rhizopus delemar* GA glucoamylase polypeptide and can include one or more amino acid variations, providing for a non-natural polypeptide. Polypeptides of the disclosure can be a portion of the naturally occurring *Rhizopus microsporus* GA and *Rhizopus delemar* GA sequence (such as polypeptides that are truncated at its N-terminus, its C-terminus, or both), while the glucoamylase polypeptide retains amylolytic activity.

N-terminal truncations can be produced by altering the position of the ATG start codon, while ensuring the sequence downstream remains in frame. C-terminal variants can be produced by inserting an in-frame premature stop codon. Random methods such as error-prone PCR could also be employed, and could be combined with growth on starch to ensure peptide function.

Variations in the *Rhizopus microsporus* GA (SEQ ID NO:1) and *Rhizopus delemar* GA (SEQ ID NO:4) sequences can be made with information about the primary sequence of these enzymes, through sequence alignments, and in view of information regarding other glucoamylase enzymes as known in the art. Most glucoamylases, including *Rhizopus microsporus* GA and *Rhizopus delemar* GA, are multidomain enzymes. Many glucoamylases, including *Rhizopus microsporus* GA and *Rhizopus delemar* GA, include a starch-binding domain connected to a catalytic domain via an O-glycosylated linker region, based on known crystal structures from similar enzymes.

Glucoamylases may also have a catalytic domain having a configuration of a configured twisted (alpha/alpha)(6)-barrel with a central funnel-shaped active site. Glucoamylases may have a structurally conserved catalytic domain of approximately 450 residues. In some glucoamylases the catalytic domain generally followed by a linker region consisting of between 30 and 80 residues that are connected to a starch binding domain of approximately 100 residues.

Glucoamylase properties may be correlated with their structural features. A structure-based multisequence alignment was constructed using information from catalytic and starch-binding domain models (see, e.g., Coutinho, P. M., and Reilly, P. J., 1994. Protein Eng. 7:393-400 and 749-760). It has been shown that the catalytic and starch binding domains are functionally independent based on structure-function relationship studies, and there are structural similarities in microbial glucoamylases. From other studies, specific glucoamylase residues have been shown to be involved in directing protein conformational changes, substrate binding, thermal stability, and catalytic activity (see, for example, Sierks, M. R., et al. 1993. Protein Eng. 6:75-79; and Sierks, M. R., and Svensson, B. 1993. Biochemistry 32:1113-1117).

Therefore, the correlation between glucoamylase sequence and protein function is understood in the art, and one of skill could design and express variants of amylolytically active glucoamylases having one or more amino acid deletion(s), substitution(s), and/or additions. For example, in some aspects, the glucoamylase portion of the *Rhizopus microsporus* GA and *Rhizopus delemar* GA can contain a truncated version of a naturally occurring glucoamylase, the truncated version having, in the least, a catalytic and optionally a starch-binding domain having amylolytic activity as described herein.

Truncated forms of glucoamylase have been generated and have been shown to have enzymatic activity. For example, Evans et al. (Gene, 91:131; 1990) generated a series of truncated forms of glucoamylase to investigate how much of the O-glycosylated region was necessary for the activity or stability of GAIL a fully active form of the enzyme lacking the raw starch-binding domain. It was found that a significant portion of the C-terminus could be deleted from GAII with insignificant effect on activity, thermal stability, or secretion of the enzyme.

Lin et. al (BMC Biochemistry 8:9, 2007) teaches there was no loss of glucoamylase activity the starch binding domain located between positions 26-131 in the *Rhizopus oryzae* glucoamylase was deleted. Also, Mertens & Skory (Enz. Microbiol. Technology 40: 874-880, 2007) isolated a natural glucoamylase which lacked a starch binding domain.

Various amino acids substitutions associated with causing a change in glucoamylase activity are also known in the art. Substitution(s) of amino acid(s) at various locations in the glucoamylase sequence have been shown to affect properties such as thermo stability, starch hydrolysis activity, substrate usage, and protease resistance. As such, the current disclosure contemplates use of a *Rhizopus microsporus* GA and *Rhizopus delemar* GA sequence that includes one or more amino acids substitution(s) in the glucoamylase portion of the polypeptide, wherein the substitutions differ from the wild type sequence of the glucoamylase.

For example, U.S. Pat. No. 8,809,023 describes a method for reducing the ratio between isomaltose synthesis and starch hydrolysis activity (IS/SH ratio) during the hydrolysis of starch. In particular, a *Trichoderma reesei* glucoamylase (Tr GA) is described (total length of 632 amino acids having an N-terminal having a signal peptide) that is modified at with amino acid positions as follows: D44R and A539R; or D44R, N61I, and A539R. This glucoamylase variant is reported to exhibit a reduced IS/SH ratio compared to said parent glucoamylase during the hydrolysis of starch.

As another example, U.S. Pat. No. 8,592,194 describes glucoamylase variants with increased thermo stability compared to wild type glucoamylase variants. Also described in this disclosure is the *Trichoderma reesei* glucoamylase but instead one or more amino acid substitutions to the native Tr GA sequence at positions 10, 14, 15, 23, 42, 45, 46, 59, 60, 61, 67, 68, 72, 73, 97, 98, 99, 102, 108, 110, 113, 114, 122, 124, 125, 133, 140, 144, 145, 147, 152, 153, 164, 175, 182, 204, 205, 214, 216, 219, 228, 229, 230, 231, 236, 239, 240, 241, 242, 244, 263, 264, 265, 268, 269, 276, 284, 291, 300, 301, 303, 310, 311, 313, 316, 338, 342, 344, 346, 349, 359, 361, 364, 379, 382, 390, 391, 393, 394, 408, 410, 415, 417, and 418. As an example, the current disclosure contemplates creating variants at amino acid locations in SEQ ID NO:1 and SEQ ID NO:4 corresponding to the respective described positions in the TrGA sequence in order to provide variants with increased thermostability.

The determination of "corresponding" amino acids from two or more glucoamylases can be determined by alignments of all or portions of their amino acid sequences. Sequence alignment and generation of sequence identity include global alignments and local alignments, which typically use computational approaches. In order to provide global alignment, global optimization forcing sequence alignment spanning the entire length of all query sequences is used. By comparison, in local alignment, shorter regions of similarity within long sequences are identified.

As used herein, an "equivalent position" means a position that is common to the two sequences (e.g., a template GA sequence and a GA sequence having the desired substitution(s)) that is based on an alignment of the amino acid sequences of one glucoamylase or as alignment of the three-dimensional structures. Thus, either sequence alignment or structural alignment, or both, may be used to determine equivalence.

In some modes of practice, the BLAST algorithm is used to compare and determine sequence similarity or identity. In addition, the presence or significance of gaps in the sequence which can be assigned a weight or score can be determined. These algorithms can also be used for determining nucleotide sequence similarity or identity. Parameters to determine relatedness are computed based on art known methods for calculating statistical similarity and the significance of the match determined. Gene products that are related are expected to have a high similarity, such as greater than 50% sequence identity. Exemplary parameters for determining relatedness of two or more sequences using the BLAST algorithm can be as follows.

Inspection of nucleic acid or amino acid sequences for two nucleic acids or two polypeptides will reveal sequence identity and similarities between the compared sequences. Sequence alignment and generation of sequence identity include global alignments and local alignments which are carried out using computational approaches. An alignment can be performed using BLAST (National Center for Biological Information (NCBI) Basic Local Alignment Search Tool) version 2.2.31 software with default parameters. Amino acid % sequence identity between amino acid sequences can be determined using standard protein BLAST with the following default parameters: Max target sequences: 100; Short queries: Automatically adjust parameters for short input sequences; Expect threshold: 10; Word size: 6; Max matches in a query range: 0; Matrix: BLO- SUM62; Gap Costs: (Existence: 11, Extension: 1); Compositional adjustments: Conditional compositional score matrix adjustment; Filter: none selected; Mask: none selected. Nucleic acid % sequence identity between nucleic acid sequences can be determined using standard nucleotide BLAST with the following default parameters: Max target sequences: 100; Short queries: Automatically adjust parameters for short input sequences; Expect threshold: 10; Word size: 28; Max matches in a query range: 0; Match/Mismatch Scores: 1, −2; Gap costs: Linear; Filter: Low complexity regions; Mask: Mask for lookup table only. A sequence having an identity score of XX % (for example, 80%) with regard to a reference sequence using the NCBI BLAST version 2.2.31 algorithm with default parameters is considered to be at least XX % identical or, equivalently, have XX % sequence identity to the reference sequence.

A global alignment can align sequences with significant identity to, for example, the SEQ ID NO:1 (*Rhizopus microsporus* GA) or SEQ ID NO:4 *Rhizopus delemar* GA glucoamylase in order to determine which corresponding amino acid position(s) in the target sequence (e.g., a glucoamylase ortholog) can be substituted with the one or more of the amino acid if a glucoamylase variant is used.

In some cases, the substitution can be a conservative substitution, such as where one amino acid of a particular type (e.g., polar, non-polar/aliphatic, positively charged/basic, negatively charged/acidic) is replaced with an amino acid of the same type. Exemplary conservative amino acid substitutions of the present disclosure can involve exchange of one aliphatic or hydrophobic amino acid Ala, Val, Leu, or Ile for another; exchange of one hydroxyl amino acid Ser or Thr for the other; exchange of one acidic amino acid Asp or Glu for the other; exchange of one amide amino acid Asn or Gln for the other, exchange of one basic amino acid Lys, Arg, for His for another; exchange of one aromatic amino acid Phe, Tyr, or Trp, for another, and exchange of one small amino acids Ala, Ser, Thr, Met, or Gly for another.

In embodiments of the disclosure, SEQ ID NO:1 has one or more amino acid mutations which causes it to be less than 100% identical to SEQ ID NO:1. For example, the glucoamylase may have multiple amino acid deletion(s), substitution(s), and/or additions causing it to have about 81% or greater identity to SEQ ID NO:1, 82% or greater, 83% or greater, 84% or greater, 85% or greater, 86% or greater, 87% or greater, 88% or greater, 89% or greater, 90% or greater, 91% or greater, 92% or greater, 93% or greater, 94% or greater, 95% or greater, 96% or greater, 97% or greater, 98% or greater, or 99% or greater identity to SEQ ID NO:1. A variant with a single amino acid substitution has 99.8% identity to SEQ ID NO:1.

In exemplary embodiments, more than one location in SEQ ID NO:1 can be changed to provide a variant that has to SEQ ID NO:1 that is less than 80%. For example, changes to the signal sequence and deletion of the starch binding domain can provide a variant with less than 80% identity to SEQ ID NO:1, such as about 75%-80% identity to SEQ ID NO:1.

FIG. 1 shows an alignment of SEQ ID NO:1 to *Rhizopus oryzae* GA, showing the signal sequence (1-25) and starching binding domain (26-131).

Table 2 is a table of sequence identity (BLAST alignment) of a "core" sequence of SEQ ID NO:1 (lacking signal sequence and starch binding domain) GA sequences of other known GAs. Accession CEG69155.1 is the same sequence as SEQ ID NO:1.

TABLE 2

| Source | Accession # | Start | End | Match | NonMatch | % Match |
|---|---|---|---|---|---|---|
| *Rhizopus microsporus* | CEG69155.1 | 132 | 605 | | | |
| *Rhizopus microsporus* | ORE14155.1 | 132 | 605 | 458 | 16 | 96 |
| *Rhizopus delemar* | EIE75378.1 | 132 | 604 | 397 | 77 | 83 |
| *Rhizopus oryzae* | P07683.2 | 132 | 604 | 394 | 80 | 83 |
| *Rhizopus oryzae* | BAH09876.1 | 132 | 604 | 395 | 79 | 83 |
| *Rhizopus oryzae* | ABB77799.1 | 132 | 604 | 396 | 78 | 83 |

In embodiments of the disclosure, SEQ ID NO:4 has one or more amino acid mutations which causes it to be less than 100% identical to SEQ ID NO:4. For example, the glucoamylase may have multiple amino acid deletion(s), substitution(s), and/or additions causing it to have about 98% or greater, or 99% or greater identity to SEQ ID NO:4. A variant with a single amino acid substitution has 99.8% identity to SEQ ID NO:4.

In exemplary embodiments, one or more of locations in SEQ ID NO:1 or SEQ ID NO:4 are changed to provide a variant SEQ ID NO:1 and SEQ ID NO:4 also generally include a native "signal sequence." Various other terms may be used to indicate a "signal sequence" as known in the art, such as where the word "signal" is replaced with "secretion" or "targeting" or "localization" or "transit" or leader," and the word "sequence" is replaced with "peptide" or "signal." Generally, a signal sequence is a short amino acid stretch (typically in the range of 5-30 amino acids in length) that is located at the amino terminus of a newly synthesized protein. Most signal peptides include a basic N-terminal region (n-region), a central hydrophobic region (h-region) and a polar C-terminal region (c-region) (e.g., see von Heijne, G. (1986) Nucleic Acids Res. 14, 4683-4690).

In SEQ ID NO:1 and SEQ ID NO:4 the predicted signal sequence is from amino acid 1 to 25 of SEQ ID NO:1 and from amino acid 1 to 25 of SEQ ID NO:4, respectively. A signal sequence can target the protein to a certain part of the cell, or can target the protein for secretion from the cell. For example, it has been shown that the native N-terminal signal sequence of the *S. diastaticus* Glucoamylase STAI gene can target it to the endoplasmic reticulum of the secretory apparatus (for example, see Yamashita, I. et al., (1985) J. Bacteriol. 161, 567-573).

Glucoamylase enzymes of the disclosure can use the native signal sequences of SEQ ID NO:1 and SEQ ID NO:4, or variants thereof, or can be modified to include a heterologous signal sequences. In one aspect, the current invention provides the partial or full replacement of the native signal sequence of SEQ ID NO:1 and SEQ ID NO:4 with a secretion signal based on a sequence at the N-terminal portion of An aa, Sc FAKS, Sc AKS, Sc MFα1, Sc IV, Gg LZ, and Hs SA as described in U.S. Provisional Patent Application 62/371,681 (published as WO2018027131) and PCT Application No. PCT/US2016/016822 (published as WO2016127083), both of which are hereby incorporated by reference in their entirety.

These secretion signals can be used as a replacement to the native secretion signal of the SEQ ID NO:1 and SEQ ID NO:4, or can be used in addition to the native secretion signal. In view of the addition of the heterologous secretion signal, the proteins may be referred to as "fusion proteins," and annotated as follows: [An aa-SS]-[Rm GA], [Sc IV-SS]-[Rd GA], etc.

Possible heterologous N-terminal replacement sequences for the N-terminal of SEQ ID NO:1 and SEQ ID NO:4 include the following. Sc-FAKS is a sequence of 90 amino acids derived from the N-terminal portion of the *Saccharomyces cerevisiae* peptide mating pheromone α-factor (e.g., see Brake, A., et al., Proc. Natl. Acad. Sci., 81:4642-4646, 1984; Kurjan, J. & Herskowitz, I., Cell 30:933-943, 1982). Sc-MFα1 is amino acids 20-89 Sc-FAKS. Sc IV a 19 amino acid N-terminal signal peptide of a sucrose hydrolase enzyme (e.g, see, Carlson M., et al. (1983) Mol. Cell. Biol. 3:439-447). Gg LZ (also known as egg white lysozyme) is an 18 amino acid N-terminal signal peptide of a glycoside hydrolase enzyme (e.g, see, Jigami et al. (1986) Gene 43:273-279). Hs SA is an 18 amino acid N-terminal signal peptide of a serum (e.g, see, Kober et al. (2013) Biotechnology and Bioengineering; 110:1164-1173.). Sc MFα2 is derived from the N-terminus the *Saccharomyces cerevisiae* mating factor alpha 2 gene (Sc MFα2). Sc PHO5 is derived from the N-terminus of the *Saccharomyces cerevisiae* repressible acid phosphatase (Meyhack et al., EMBO J. 6:675-680, 1982).

Molecular techniques can be performed to create a nucleic acid sequence that is a template for the expression of genes encoding SEQ ID NO:1 or SEQ ID NO:4, or variants thereof. As a general matter, a nucleic acid is prepared to encode a protein comprising SEQ ID NO:1 or SEQ ID NO:4, or variants thereof.

In other aspects, the SEQ ID NO:1 or SEQ ID NO:4, or variants thereof optionally comprises additional sequence that is not present in the native glucoamylase polypeptide. The additional sequence, in some aspects, can provide functionality to the glucoamylase that is not present in the native polypeptide. Additional functionalities include, for example, protease sites or binding sites for other proteins or materials, or linker regions.

Nucleic acids sequences encoding SEQ ID NO:1 or SEQ ID NO:4, or variants thereof, as well as any regulatory sequence (e.g., terminator, promoter, etc.) and vector sequence (e.g., including a selection marker, integration marker, replication sequence, etc.) can, in some modes of practice, be prepared using known molecular techniques. General guidance for methods for preparing DNA constructs (e.g., for the DNA constructs including nucleic acids encoding SEQ ID NO:1 or SEQ ID NO:4 or a variant thereof) can be found in Sambrook et al Molecular Cloning, A Laboratory Manual, Cold Spring Harbor Laboratory Press, Cold Spring Harbor, N.Y., 1989; and Ausubel et al. Current Protocols in Molecular Biology, Greene Publishing and Wiley-Interscience, New York, N.Y., 1993. PCR techniques can be used for modifying nucleic acids encoding SEQ ID NO:1 or SEQ ID NO:4, to optionally introduce one or more mutations in the sequence to provide a variant.

PCR techniques are described in, for example, Higuchi, (1990) in PCR Protocols, pp. 177-183, Academic Press; Ito et al (1991) Gene 102:67-70; Bernhard et al (1994) Bioconjugate Chem. 5:126-132; and Vallette et al (1989) Nuc. Acids Res. 17:723-733. The techniques may optionally include site-directed (or oligonucleotide-mediated) mutagenesis, PCR mutagenesis, and cassette mutagenesis of an earlier prepared DNA encoding a glucoamylase polypeptide.

Alternatively, nucleic acid molecules can be generated by custom gene synthesis providers such as ATUM (Menlo Park, CA) or GeneArt (Life Technologies, Thermo Fisher Scientific).

An expression vector can be constructed to include the glucoamylase nucleic acid sequence operably linked to expression control sequences functional in the host organism. Expression vectors applicable for use in the host organisms include, for example, plasmids, episomes and artificial chromosomes. The vectors can include selection sequences or markers operable for stable integration into a host chromosome. Additionally, the vectors can include one or more selectable marker genes and appropriate expression control sequences. Selectable marker genes also can be included that, for example, provide resistance to antibiotics or toxins, complement auxotrophic deficiencies, or supply critical nutrients not in the culture medium. Expression control sequences can include constitutive and inducible promoters, transcription enhancers, transcription terminators, and the like which are well known in the art.

In some aspects, the nucleic acid can be codon optimized. The nucleic acid template can be the native DNA sequence that codes for the glucoamylase, or the template can be a codon-optimized version that is optimized for expression in a desired host cell. Databases that provide information on desired codon uses in particular host organisms are known in the art.

The DNA construct comprising the glucoamylase nucleic acid can be operably linked to a promoter sequence, wherein the promoter sequence is functional in a host cell of choice. In some aspects, the promoter shows transcriptional activity in a fungal host cell and may be derived from genes encoding proteins either homologous or heterologous to the host cell. In some aspects, the promoter is useful for expression in *S. cerevisiae*. Examples of well-known constitutive promoters include, but are not limited to the cytochrome c promoter (pCYC), translational elongation factor promoter (pTEF), the glyceraldehyde-3-phosphate dehydrogenase promoter (pGPD/TDH3), the phosphoglycerate kinase promoter (PGK), and the alcohol dehydrogenase promoter (pADH). Optionally, an additional factor that controls expression such as an enhancer or the like may also be included on the vector.

The expression vector including the glucoamylase gene can also include any termination sequence functional in the host cell. For example, the termination sequence and the promoter sequence can be from the same cell, or the termination sequence is homologous to the host cell. The termination sequence can correspond to any promoter that is used.

The DNA construct may be introduced into a host cell using a vector. The vector may be any vector which when introduced into a host cell is stably introduced. In some aspects, the vector is integrated into the host cell genome and is replicated. Vectors include cloning vectors, expression vectors, shuttle vectors, plasmids, phage particles, cassettes and the like. In some aspects, the vector is an expression vector that comprises regulatory sequences operably linked to the glucoamylase coding sequence. SEQ ID NOs as described herein can be assembled in the cell by the transformation of multiple smaller DNA fragments (e.g., "SEQ ID NO sub-fragments") with overlapping homology that in total constitute a particular SEQ ID NO. For example, the integration of a desired SEQ ID NO, or portion thereof, at a gene locus in the cell can be accomplished by the co-transformation of two to five DNA sub-fragments, which are subjected to recombination with each other and integration into a genetic locus in the cell having homology to portions of the sub-fragments.

The DNA construct comprising the glucoamylase gene can further include a selectable marker, thereby facilitating the selection in a host cell. For example, the selectable marker can be for transformed yeast. Examples of yeast selectable marker include markers commonly used for selecting for transformed yeast cells. Auxotrophic markers can be used using a gene that controls an auxotrophy, meaning that the gene enables yeast to produce a nutrient required for the growth of the yeast. Examples genes that control auxotrophies include leucine auxotrophy (LEU2), histidine auxotrophy (HIS3), uracil auxotrophy (URA3, URA5), and tryptophan auxotrophy (TRP1).

The DNA construct may be one which is integrated into the genome and replicated together with the chromosome(s) into which it has been integrated. For example, a yeast cell may be transformed with the DNA construct encoding the glucoamylase, and integrating the DNA construct, in one or more copies, in the host chromosome(s). This integration is generally considered to be an advantage, as the DNA sequence is more likely to be stably maintained. Integration of the DNA constructs into the host chromosome may be performed according to conventional methods, such as by homologous or heterologous recombination.

Engineered yeast of the disclosure can include having multiple copies (two or more) of the gene encoding SEQ ID NO:1 or SEQ ID NO:4, or variants thereof. For example, the engineered yeast can be an engineered *Saccharomyces* that has at least first, second, third, and fourth exogenous nucleic acids each including a sequence encoding at least one SEQ ID NO:1 or SEQ ID NO:4, or variants thereof. If the engineered yeast includes multiple copies of a gene encoding the glucoamylase gene, the nucleic acid sequences of the copies can be the same or different from one another. Exemplary methods and yeast strains that have been engineered to include multiple copies of glucoamylase genes are described in International Application serial no. PCT/US16/24249, filed Mar. 25, 2016 (Miller, et al.), which is hereby incorporated by reference in its entirety.

The engineered yeast can also optionally include introduction of exogenous nucleic acid sequences, changes to regulatory elements that either upregulate or down regulate expression of genes; increase in gene copy numbers, and deletions or mutations that eliminate expression, reduce expression, or increase expression or activity of a gene or gene product. The heterologous modification can include one or more of the following: the use of a promoter that is different than the native promoter of the desired gene; the use of a terminator that is different than the native terminator of the desired gene; the introduction of the gene at a location in the genome that is different than its native location; the introduction of multiple copies of the desired gene.

An additional genetic modification that can be included in the engineered yeast is the alteration or introduction of an enzyme activity that converts a low molecular weight non-glucose sugar to glucose. For example, one optional additional genetic modification affects or introduces isomaltase activity in the engineered yeast during growth on glucose. Isomaltase can convert isomaltose to glucose by hydrolyzing the 1,6 ether linkage in isomaltose. An isomaltase may also exhibit cross activity for hydrolyzing the 1,4 ether linkages in maltose. The genetic modification can cause isomaltase activity to be introduced into the cell, cause an increased amount of isomaltase in the cell, and/or cause an increase in isomaltase activity.

In some embodiments further to the glucoamylase gene, the engineered cell includes a heterologous isomaltase gene, or an isomaltase gene under the control of a heterologous promoter that provides increased expression in the cell, or present in multiple copies in the cell. For example, an isomaltase (IMA) gene under the control of a heterologous promoter, such as a PDC promoter can be engineered into the yeast.

Examples of isomaltase genes that can be introduced into an engineered yeast include, but are not limited to *Saccharomyces cerevisiae* IMA1 (P53051), *Saccharomyces cerevisiae* IMA2 (Q08295), *Saccharomyces cerevisiae* IMA3 (POCW40), *Saccharomyces cerevisiae* IMA4 (POCW41), *Saccharomyces cerevisiae* IMA5 (P40884), *Bacillus subtilis* malL (006994), *Bacillus cereus* malL (P21332), *Bacillus coagulans* malL (Q45101), *Bacillus* sp. malL (P29093), etc. Preferably the isomaltase gene encodes for a polypeptide having greater than 80%, 85%, 90%, 95%, 98% or 99% sequence identity with the amino acid sequence of accession number NP 011803.3 (*Saccharomyces cerevisiae* IMA1).

In some embodiments, the engineered yeast can further include a genetic modification that provides a starch-degrading polypeptide that is different than the glucoamylase. For example, the genetic modification can be one that introduces a nucleic acid encoding a different polysaccharide-degrading enzyme, such as an exogenous or modified alpha-amylase, a betaamylase, a pullulanase, or an isoamylase. The genetic modification may also be one that increases the amount of an endogenous or an exogenous starch-degrading polypeptide in the cell, such as by placing the gene under control of a strong promoter, or providing the gene in multiple copies in the cell, such as multiple copies of the gene integrated into the genome, or multiple copies present on a non-chromosomal construct (e.g., a plasmid).

In some embodiments, the engineered yeast can further include a genetic modification that provides an exogenous or modified sugar transporter gene (such as an isomaltose transporter); See, for example, commonly assigned U.S. application Ser. No. 62/268,932 filed Dec. 17, 2015, entitled "Sugar Transporter-Modified Yeast Strains and Methods for Bioproduct Production," published as WO2017106739, which is hereby incorporated by reference in its entirety.

Various host cells can be transformed with a nucleic acid encoding SEQ ID NO:1 or SEQ ID NO:43, or a variant thereof. In some aspects, the nucleic acid including the glucoamylase gene is present in a bacterial cell. The bacterial cell can be used, for example, for propagation of the nucleic acid sequence or for production of quantities of the polypeptide.

In other aspects, the host cell is a eukaryotic cell, such as a fungal cell.

In other aspects, the heterologous glucoamylase can be purified for use in an enzyme composition, either alone or in combination with other enzymes.

In some aspects, the host cell has tolerance to a higher amount of a bioderived product, such as ethanol, in the fermentation medium. In some aspects, the host cell is an "industrial yeast" which refers to any yeasts used conventionally in ethanol fermentation. Examples include sake yeasts, shochu yeasts, wine yeasts, beer yeasts, baker's yeasts, and the like. Sake yeasts demonstrate high ethanol fermentability and high ethanol resistance and genetic stability. Typically, an industrial yeast has high ethanol resistance and preferably is viable at ethanol concentrations of 10% or greater.

In exemplary aspects, the yeast including the glucoamylase gene is a *S. cerevisiae* yeast. Some *S. cerevisiae* strains have high tolerance to ethanol. Various strains of ethanol tolerant yeast are commercially available, such as RED STAR™ and ETHANOL RED™ yeast (Fermentis/Lesaffre, USA), FALI™ (Fleischmann's Yeast, USA), SUPERSTART and THERMOSACC™ yeast (Ethanol Technology, Wis., USA), BIOFERM™ AFT and XR (NABC-North American Bioproducts Corporation, GA, USA), GERT STRAND (Gert Strand AB, Sweden), SUPERSTART™ (Alltech), ANGEL™ (Angel Yeast Ltd, China) and FERMIOL™ (DSM Specialties).

Industrial yeasts are typically prototrophic and therefore do not have an auxotrophic marker suitable for selecting for a transformant. If the yeast does not have the genetic background that would otherwise facilitate retention of the glucoamylase gene of SEQ ID NO:1 or SEQ ID NO:4, or variant thereof, within the cell upon transformation, the host cell can be engineered to introduce one or more genetic mutation(s) to establish use of a marker gene in association with and to maintain the glucoamylase gene in the cell. For example, a commercially available ethanol tolerant yeast cell can be genetically modified prior to introducing the glucoamylase gene in the cell.

A marker for a different auxotrophy can be provided by disrupting the gene that controls the auxotrophy. In one mode of practice, an ethanol tolerant strain of yeast is engineered to disrupt copies of one or more genes that control auxotrophies, such as LEU2, HIS3, URA3, URA5, and TRP1. In the case of providing uracil auxotrophy, for example, a normal ura3 gene of an ethanol tolerant yeast can be replaced with an ura3⁻ fragment obtained from a uracil auxotrophic mutant (for example, a *Saccharomyces cervisiae* MT-8 strain) to disrupt the normal ura3 gene. In the case of a ura3 gene-disrupted strain, the presence/absence of a marker can be easily identified or selected by taking advantage of the fact that a ura3 gene-disrupted strain is able to grow in a medium containing 5-fluoroorotic acid (5-FOA) while a normal ura3 strain (wild-type yeast or usual industrial yeast) is not able to grow. In the case of a lys2 gene-disrupted strain, the presence/absence of a marker can be easily identified or selected by taking advantage of the fact that a lys2 gene-disrupted strain is able to grow in a medium containing α-aminoadipic acid while a normal lys2 strain (wild-type yeast or usual industrial yeast) is not able to grow. Methods for disrupting an auxotrophy-controlling gene and for selectively separating auxotrophy-controlling gene mutants may be used depending on the auxotrophy employed. Alternatively, one can employ dominant selection markers, such as the amdS from *Aspergillus nidulans* (U.S. Pat. No. 5,876,988), which allows for growth on acetamide as the sole nitrogen source; or ARO4-OFP, which allows for growth in the presence of fluoro-phenylalanine (Fukuda et. al.). These markers can be used repeatedly using the recyclable cre-loxP system, or alternatively can be used to create auxotrophic strains that allow additional markers to be utilized.

After the host cell has been engineered to provide a desired genetic background for introduction of the glucoamylase gene, the gene construct is introduced into a cell to allow for expression. Methods for introducing a gene construct into a host cell include transformation, transduction, transfection, co-transfection, electroporation. In particular, yeast transformation can be carried out using the lithium acetate method, the protoplast method, and the like. The gene construct to be introduced may be incorporated into a chromosome in the form of a plasmid, or by insertion into the gene of a host, or through homologous recombination with the gene of a host. The transformed yeast into which the gene construct has been introduced can be selected with a selectable marker (for example, an auxotrophic marker as mentioned above). Further confirmation can be made by measuring the activity of the expressed protein.

The transformation of exogenous nucleic acid sequences including the glucoamylase gene can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The engineered yeast of the disclosure can be provided in any suitable form. In some aspects, the non-natural yeast is dehydrated to form a dry yeast composition. The dry yeast composition can have increased shelf life over wet compositions.

Fermentation using a host cell expressing the glucoamylase gene can be performed in a fermentation medium made from a feedstock derived from a starch and/or sugar containing plant material, referring to a starch and/or sugar containing plant material derivable from any plant and plant part, such as tubers, roots, stems, leaves and seeds. Starch and/or sugar comprising plant material can be obtained from cereal, such as barley, wheat, maize, rye, sorghum, millet, barley, potatoes, cassava, or rice, and any combination thereof. The starch- and/or sugar comprising plant material can be processed, such as by methods such as milling, malting, or partially malting. In some aspects, the starch material is from corn flour, milled corn endosperm, sorghum flour, soybean flour, wheat flour, biomass derived starch, barley flour, and combinations thereof. Starch-containing feedstocks used to form a fermentation medium can be made from any of these plant materials.

In some aspects, a feedstock used to form a fermentation medium includes a treated starch. For example, the fermentation medium can include a partially hydrolyzed starch. The partially hydrolyzed starch can include high molecular weight dextrins and high molecular weight maltodextrins. Collectively, starch, dextrins, maltodextrins, and any other polymerized form a glucose are glucose polymers. Partially hydrolyzed starches and preparation thereof are well known in the art. Partially hydrolyzed starches can be prepared by heating the starch with an acid such as hydrochloric or sulfuric acid at a high temperature and then neutralizing the hydrolysis mixture with a suitable base such as sodium carbonate. Alternatively, partially hydrolyzed starches can be prepared by an enzymatic process, such as by adding alpha-amylase to a starch preparation. An alpha amylase can cause the endohydrolysis of (1→4)-alpha-D-glucosidic linkages in polysaccharides containing three or more (1→4)-alpha-linked D-glucose units. A partially hydrolyzed starch product can be used that have amounts of starch and starch degradation products within desired ranges. Partially hydrolyzed starch includes preparations having minimal hydrolysis (e.g., a DE of 5, having little dextrose) to preparations having substantial hydrolysis (e.g., a DE of 95, predominantly dextrose).

The feedstock can be a "liquefact", which is corn starch that has undergone liquefaction, with a dextrose equivalents in the range of about 10 to about 15. A corn wet milling process can be used to provide steep-water, which can be used for fermentation. Corn kernels can be steeped and then milled, and separated into their major constituent fractions. Light steep water is a byproduct of the steeping process, and contains a mixture of soluble proteins, amino acids, organic acids, carbohydrates, vitamins, and minerals.

In some aspects, the feedstock can be dry grind corn, i.e., most or all of the corn kernel components are included in the fermentation feedstock. The dry-grind corn process is the most common technology for converting corn to ethanol in the U.S. Some aspects of dry-grind processing differ from the wet milling process (which uses liquefact), including, but not limited to adding urea to provide sufficient nitrogen for fermentation. The primary aspects of dry-grind processes for producing ethanol are well known in the art.

Feedstocks derived from any of the plant materials described herein generally include a "glucose polymer" which refers to those polymers including two or more glucose residues. Shorter glucose polymers including glucose dimers (e.g., maltose), trimers (e.g., triose), and those up to about 10 glucose units, which may also be referred to as "glucose oligomers." Feedstocks of hydrolyzed starch preparations with a DE in the range of about 2 to about 20 include predominantly maltodextrins, which include glucose polymers having a DP of 3 (540 Da) to over about 5000 ($10^6$ Da). For example, a starch preparation with a DE 2 includes most maltodextrins in the range of 200,000 to about 1×105 Da, and DEs in the range of about 10 to about 20 have most maltodextrins in the range of about 540 to about 100,000 Da. Degree of polymerization (DP) refers to the number of sugar monomer residues in a glucose polymer.

Based on the DE of the partially hydrolyzed starch, the concentrations (% wt) of glucose (DP 1), maltose (DP 2), triose (DP 3), and longer glucose polymers of DP 4+ can be known in the composition. Table 3 provides concentrations (% wt) of various meric forms of glucose at various DE points, as understood in the art.

TABLE 3

| DE | Glucose (DP 1) | Maltose (DP 2) | Triose (DP 3) | DP 4-6 | DP 7+ |
|---|---|---|---|---|---|
| 5 | <1 | 1 | 2 | 7 | 90 |
| 10 | <1 | 3 | 4 | 15 | 78 |
| 15 | <1 | 6 | 7 | 21 | 66 |
| 20 | <1 | 8 | 9 | 29 | 53 |
| | | | | DP 4+ | |
| 28 | 8 | 8 | 11 | 73 | |
| 36 | 14 | 11 | 10 | 65 | |
| 43 | 19 | 14 | 12 | 55 | |
| 53 | 28 | 18 | 13 | 41 | |
| 63 | 36 | 31 | 13 | 20 | |
| 66 | 40 | 35 | 8 | 17 | |
| 95 | 95 | 3 | 0.5 | 1.5 | |
| 100 | 100 | 0 | 0 | 0 | |

Benefits of the engineered yeast of the current disclosure allow use of fermentation mediums made from feedstocks with low DEs, such as feedstocks having a DE of less than about 40, less than about 30, less than about 20, less than about 15, or less than about 10. Such feedstocks may require the need for using exogenous starch-degrading enzymes to generate glucose for cell growth and bioproduct formation. However, starch-containing feedstocks with higher DEs can be used in methods with engineered yeast of the disclosure, and the engineered yeast can still provide fermentation benefits. For example, methods of the invention may use s feedstock including partially hydrolyzed starch having a DE of not greater than about 75, or not greater than about 70, and greater than about 35, or greater than about 40, and more preferably in the range of about 45 to about 65. A DE in the range of about 45 to about 65 means that glucose is present in the feed composition in the range of about 19% to about 40% (wt), maltose in the range of about 14 to about 35% (wt), triose in the range of about 8 to about 12% (wt), and glucose polymers having a DP of 4 or greater in the range of about 17% to about 55%. The percentages are based on the total amount of all "meric" forms of glucose in the composition. Fermentation and addition of starch-containing feedstocks can be carried out to provide glucose and glucose polymer within desired ranges as expressed as a percentage of the total amount of all "meric" forms of glucose in the composition.

In aspects of the disclosure, given production and secretion of the glucoamylase from the engineered yeast into the fermentation medium, the fermentation method may omit addition of purified or enriched commercial glucoamylase into the medium, or at least allow significantly less commercial glucoamylase to be used in a fermentation method. For example, the engineered yeast of the disclosure can allow addition of commercial glucoamylase to be eliminated or at least reduced by about 50%, 60%, 70%, 80%, 90%, or 95%. 100% reduction can be attained using the yeast described herein, especially if a longer fermentation period, for example 60 hours is used. Typically, amounts of glucoamylase in the range of about 0.014-0.071 AGU/g DS would be used in fermentation methods that do not use a glucoamylase-secreting engineered yeast.

The benefits of using yeast engineered to express a glucoamylase enzyme according to SEQ ID NO:1 or SEQ ID NO:4, can be understood by fermenting the yeast in a fermentation medium made from a liquified corn mash having a low DE, such as not greater than about 50, not greater than about 35, not greater than about 30, or not greater than about 25, or not greater than about 20, or not greater than about 15, such as in the range of about 2 to about 20, about 2 to about 15, or about 5 to about 5, and fermenting the medium to generate ethanol. The feedstock used to prepare the fermentation medium may optionally be described in terms of glucose concentration as an overall percentage of fermentable carbohydrates (glucose and glucose polymers) in the feedstock. For example, the fermentation medium can be made from a starch feedstock having a glucose concentration of about 2% or less, or about 1% or less, such as in the range of about 0.1% to about 2%, 0.1% to about 1.5%, or to about 0.1% to about 1%. At the end of the fermentation period, the ethanol concentration is 70 g/kg or greater in the fermentation media.

To determine if a yeast expressing a glucoamylase is capable of producing an ethanol concentration of 70 g/kg or great in the fermentation media at the end of a fermentation period, the following test can be conducted: First a fermentation medium using a starch feedstock having a DE of 30+/−2 is produced by preparing a corn mash (or liquefied corn mash) using a predetermined amount of yellow dent #2 corn that is milled and passed through a US #20 sieve. Overs (twice-ground corn that was retained on a US #20 sieve) are added back at a X:Y ratio of overs to sieved corn (0.020 overs/total corn mass ratio). The moisture content is measured by the halogen moisture balance method to determine the dry weight of the milled corn. Water is added to create a 32% slurry (w/w, dry weight basis). Concentrated sulfuric acid is added to reach a pH between 5.7-5.9. Calcium chloride dihydrate powder is added to achieve a Calcium concentration of 35 ppm. Amylase (Liquozyme™ Novozymes Liquozyme Supra 2.2X) is added based on the corn dry starch weight at a dosage ratio of 2.84 kg/ton dry basis starch dosage and the slurry is transferred to a Buchi Rotovapor R-220 flask equipped with an oil bath preset at 85° C. The reaction is allowed to proceed for 2 hours, stopping once the dextrose equivalents (DE) reaches 30+/−2 by reducing the temperature to between 34-36° C. The pH is adjusted to 5.0 with additional concentrated sulfuric acid. The DE is determined by using an osmometer (Advanced™ Model 3D3 and Precion system Model Osmette XL™) Sugar and oligocarbohydrates contents are determined using HPLC with Aminex HPX-87H column (300 mm×7.8 mm) at 60 C, 0.01N sulfuric acid mobile phase, 0.6 mL/min flow rate. To the starch feedstock a 50% urea solution and 10% ampicillin solution are added, targeting a final concentration of 1900 ppm and 5 ppm, respectively. A single fermentation typically contains 50 g of corn mash, 190 ul of 50% urea, and 2.5 ul of 10% ampicillin. A typical fermentation vessel is a baffled 250 ml shake flask fitted with an air-lock. The air lock should contain four to five milliliters of canola oil. The flask is inoculated to a starting $OD_{600}$ of 0.1, using a cell slurry made by scraping a fresh YPD plate into 1 ml of sterile water, Inoculate the fermentation medium with an engineered yeast that is ethanol tolerant (e.g., ETHANOL REDO) having an exogenous nucleic acid that expresses SEQ ID NO:1 or SEQ ID NO:4 to an $OD_{600}$ of 0.1. Fermentation is carried out in flasks at 30° C. with shaking in an orbital shaker at 100 rpm for approximately 48 hours. At 48 hours, as sample is analyzed for the concentration of ethanol, and optionally other compounds such as glucose, by high performance liquid chromatography with refractive index detector.

Without any commercial glucoamylase supplementation and using the feedstock described above, typical ethanol titers in the range of about 115 g/kg to about 135 g/kg can be observed using an engineered yeast expressing a glucoamylase of SEQ ID NO:1 or SEQ ID NO:4, or a variant thereof. Greater ethanol titers can be achieved with modifications to the yeast and/or the fermentation conditions. For example, in some embodiments wherein supplemental commercial glucoamylase is added to the medium, greater amounts of ethanol can be produced, such as an amount of 110 g/kg or greater, or 125 g/kg or greater, or 140 g/kg or greater, in the fermentation medium. In addition to the higher final ethanol titers, the fermentation rate can also be increased as free glucose may no longer be limiting the fermentation. Addition of the commercial glucoamylase further acts on starch polymers to create more glucose in the fermentation medium, resulting in increased cell growth and higher ethanol titers.

To achieve an ethanol concentration of 110 g/kg or greater in the fermentation media at the end of a fermentation period, the following test can be conducted. Prepare a starch feedstock and fermentation media as previously described. Supplement the fermentation medium with commercial glucoamylase enzyme (Spirizyme Fuel HS, Novozymes) to provide an additional glucoamylase activity in the medium. 0.097 AGU/g DS, or 30% of the dose required for the wild type can provide a benefit. Glucoamylase activity (AGU) is defined as the amount of enzyme which hydrolyzes 1 micromole maltose per minute under the standard conditions 37° C., using 23.2 mM maltose in 100 mM acetate buffer pH 4.3, using a reaction time of 5 minutes. Innoculate the fermentation medium with an engineered yeast that is ethanol tolerant (e.g., ETHANOL REDO) having an exogenous nucleic acid that expresses SEQ ID NO:1 or SEQ ID NO:4. Carry out fermentation for a period of 48 hours at 30° C. With the commercial glucoamylase supplementation and using a low glucose feedstock, typical ethanol titers in the range of about 110 g/kg to about 160 g/kg can be observed.

Test 1 is a method as described in the preceding paragraphs when done at 30° C. without commercial GA supplementation, Test 2 is a method as described in the preceding paragraphs when done at 30° C. with 0.097 AGU/g DS GA supplementation. Test 3 is a method as described in the preceding paragraphs when done at 33.3° C. without commercial GA supplementation. Test 4 is a method as described in the preceding paragraphs when done at 33.3° C. with 0.0.097DS GA supplementation. A preferred yeast is one that can produce a minimum of 70 g/kg in Test 1 AGU/g (all of the GA strains) and a minimum of 130 g/kg in test 4 (the 2×Rmic and 4×Rdel strains).

In further embodiments, following a period of fermentation, yeast engineered with of glucoamylases of the disclosure can provide a desirable final fermentation medium with high levels of bioproduct (e.g., ethanol) and low levels of byproduct. For example, the final fermentation medium can have high levels of glucose (e.g., 70 g/kg or greater, 90 g/kg or greater, 110 g/kg or greater, 125 g/kg or greater, or 140 g/kg or greater), and low levels of glucose, such as 1.0 g/kg or less (e.g., 0.9 g/kg or less, 0.8 g/kg or less, 0.7 g/kg or less, 0.6 g/kg or less, or 0.5 g/kg or less). In the final fermentation medium with high ethanol titers, low glucose is beneficial as it improves downstream processes, such as separation of components (e.g., ethanol) in the final fermentation medium.

The fermentation medium includes water and preferably includes nutrients, such as a nitrogen source (such as proteins), vitamins and salts. A buffering agent can also be present in the fermentation medium. Other components may also be present in the fermentation broth after a period of fermentation, such as fermentation products which can accumulate as the fermentation progresses, and other metabolites. Optionally, the fermentation broth can be buffered with a base such as calcium hydroxide or calcium carbonate, ammonia or ammonium hydroxide, sodium hydroxide, or potassium hydroxide in order to maintain a pH at which the organism functions well.

The fermentation medium can optionally include one or more of the following enzymes that are different than the glucoamylase of SEQ ID NO:1 or SEQ ID NO:4, or variant thereof. Exemplary other enzymes include alpha amylases, beta-amylases, peptidases (proteases, proteinases, endopeptidases, exopeptidases), pullulanases, isoamylases, cellulases, hemicellulases, endo-glucanases and related beta-glucan hydrolytic accessory enzymes, xylanases and xylanase accessory enzymes, acetolactate decarboxylases, cyclodextrin glycotransferases, lipases, phytases, laccases, oxidases, esterases, cutinases, granular starch hydrolyzing enzymes and other glucoamylases. These other enzymes can optionally be added to the fermentation medium or the starch-containing feedstock, such as by using a purified commercial preparation of the enzymes. Alternatively, one or more of the other enzymes can be secreted from the engineered yeast expressing SEQ ID NO:1 or SEQ ID NO:4, or from a different engineered cell.

The engineered yeast of the current disclosure can optionally be described in terms of the engineered yeast's specific growth rate. The growth rate of yeast can be defined by L=log(numbers) where numbers is the number of yeast cells formed per unit volume (mL), versus T (time).

The fermentation is carried out under conditions so that fermentation can occur. Although conditions can vary depending on the particular organism and desired fermentation product, typical conditions include a temperature of about 20° C. or greater, and more typically in the range of about 30° C. or greater. During fermentation the reaction mixture can be mixed or agitated. In some modes of practice, the mixing or agitation can occur by the mechanical action of sparging gas to the fermentation broth. Alternatively, direct mechanical agitation such as by an impellor or by other means can be used during fermentation.

The disclosure also provides non-natural yeast that have the ability to grow, and/or can produce a fermentation product at temperatures that are greater than those in which yeast, such as *Saccharomyces cerevisiae*, typically are used in fermentation processes. For example, *S. cerevisiae* typically have optimal growth at a temperature of about 30° C. However, engineered yeast of the disclosure can grow and provide excellent bioproduct (e.g., ethanol) titers at higher temperatures, and can also provide low residual glucose. For example, in some embodiments using the engineered yeast of the disclosure, fermenting is carried out at a temperature in the range of 31° C. to 35° C., or 32° C. to 34° C., for most or all of a fermentation period. Even at the higher temperatures, the engineered yeast are able to generate glucoamylase activity in the medium, and promote excellent cell growth and bioproduct production.

During a fermentation process the fermentation medium can reach an elevated temperature such as about 32° C. or about 32° C. or greater during one or more time(s) during the fermentation process. The temperature can be elevated during part of the fermentation period, or during the entire fermentation period. The temperature can be elevated for 5 minutes of greater, 10 minutes of greater, 30 minutes or greater, 1 hour or greater, 2 hours or greater, 5 hours or greater, or 10 hours or greater. The time of elevated temperature can also be expressed as a total of the overall fermentation period, such as about 0.1% to 100%, about 0.1% to about 75%, about 0.1% to about 50%, about 0.1% to about 25%, about 0.1% to about 10%, about 0.1% to about 5%, about 0.1% to about 2.5%, about 0.1% to about 1%, or about 0.1% to about 0.5% of the fermentation period.

The engineered yeast can also provide a commercially relevant titer of ethanol during or after the period of elevated temperature. For example, during or after the period of elevated temperature, for example, the ethanol titer can be in the range of about 110 g/L to about 170 g/L, in the range of about 125 g/L to about 170 g/L, or in the range of about 140 g/L to about 170 g/L. Accordingly, the engineered yeast described herein can produce ethanol at a commercially useful titer during or after a period of high temperature that would typically cause issues in other currently available yeast strains used in ethanol-producing fermentation processes. Such issues include but are not limited to: death to a significant percentage of yeast cells; deleterious effects on the ability of the yeast to reproduce; and/or reduction or elimination of the ability of the yeast to produce a fermentation product.

Miller et al. (both WO2016127083, filed Feb. 6, 2015, and PCT/US17/045493, filed Aug. 4, 2017, which are hereby incorporated by reference in their entirety) describes the utility of swapping the leader sequence on several glucoamylases, but also highlights the need for additional modifications to the host to achieve acceptable ethanol/glucose titers at the elevated temperatures. Specifically, Miller describes the effect of expressing the Mfalpha2-*R. oryzae* GA on ethanol and residual glucose titers at two different temperatures, 30° C. and 33.3° C. Temperature is a well-known antagonist to healthy ethanol fermentations, and producers spend a significant amount of capital and operating cost in terms of cooling capacity to keep their fermenters in the safe zone, typically less than 34° C. Heterologous protein production is also a well described stressor in engineered organisms, as energy directed towards cell growth and maintenance is diverted to non-natural production processes as described in Mattanovich et. al (Journal of Biotechnology 113, 2004). Alleviating the burden of heterologous protein production has been an area of intense focus over the past several decades, in all aspects of biotechnology (e.g. pharma, industrial enzymes, etc), and is not limited to the yeast *Saccharomyces cerevisiae*. Classical techniques and targeted pathway engineering, two primary methods to overcome the obstacles of producing protein and maintaining healthy host performance have resulted in some success (Payne et. al 2008, Gasser et. al 2007, Valkonen et. al 2003). These results also indicate that there is no one solution to the problem, and a solution for one protein may not work for another.

In some cases, fermentation is carried out in industrial capacity fermenters in order to achieve commercial scale economic benefits and control. In an aspect, the fermentation is carried out in a fermenter that has a capacity of about 10,000 liters or more.

The pH of the fermentation medium can be adjusted to provide optimal conditions for glucoamylase activity, cell growth, and fermentation activity to provide a desired product, such as ethanol. For example, pH of the solution can be adjusted to in the range of 3 to 5.5. In one mode of practice, the pH of the fermentation medium is in the range of 4 to 4.5.

As noted above, the present fermentation process using genetically modified yeast expressing SEQ ID NO:1 or SEQ ID NO:4, or a variant thereof, and capable of secreting the enzyme produced into the fermentation medium. These enzymes are therefore directly exposed to the broth conditions and affect the carbohydrate composition in the fermentation medium. In the fermentation medium the glucoamylase can cause hydrolysis and release of D-glucose from the non-reducing ends of the starch or related oligo- and polysaccharide molecules by cleaving alpha(1,4) and alpha-(1,6) glucosidic bonds.

Starch may also be acted on by one or more other amylases (e.g., alpha-amylase) present in the fermentation medium. For example, if alpha-amylase is present in the fermentation medium it can cause partial hydrolysis of precursor starch and cause a partial breakdown of the starch molecules by hydrolyzing internal alpha-(1,4)-linkages.

In some modes of practice, the fermentation is carried out as a single batch until completion. In other modes of practice, the fermentation is carried out as a fed batch fermentation process. In this mode of practice, a first portion of a total amount of starch material to be fermented is added to the fermentation medium wherein the glucoamylase enzyme acts on the starch to cause formation of glucose to be used as a substrate for fermentation. Additional starch material can be added in one or more portions to provide more substrate for the glucoamylase enzyme in the medium. The addition of starch can be regulated and the formation of glucose can be monitored to provide efficient fermentation.

In some modes of practice, the fermentation is carried out in a continuous mode of operation. In this mode, multiple fermenters operate in series in which a starch hydrolysate is supplied in the first fermenter, which is fed to second fermenter and so on until the starch hydrolysate is converted to ethanol. Continuous operation can be operated using between 2-7 fermenters.

In some modes of practice, a portion of the total amount of starch material is added to the fermentation broth using a variable rate addition system. Examples of such systems include a variable speed pump or a metering valve (such as a throttle valve) operably connected to a pump, which pump or valve can be utilized to vary the amount of starch material introduced into the fermentation broth over time. In some modes of practice, during the addition of a portion of the starch material, glucose concentration is monitored by a real-time monitoring system.

Real-time monitoring systems include systems that directly monitor glucose concentration and systems that indirectly monitor glucose concentration. Examples of real-time monitoring systems that typically directly monitor glucose concentration include systems based on infrared (IR) spectroscopy, near-infrared (NIR) spectroscopy systems, Fourier transform infrared (FTIR) systems, systems based on refractive index, automated enzyme based measurement systems such as a YSI 2950 Biochemistry Analyzer sold by YSI Life Sciences systems, high performance liquid chromatography (HPLC) based systems, gas chromatography (GC) based systems, and other real-time monitoring systems known to one of skill in the art. Additionally real-time monitoring systems that indirectly monitor/measure the glucose concentration of a fermentation process can be developed by determining the typical carbon distribution in a particular fermentation process and correlating the glucose concentration present in the fermentation broth to another parameter exhibited by the fermentation, such as, for example, a correlation of the glucose level present in the fermentation broth with a measurement of the carbon dioxide evolution rate and the amount of carbon dioxide present in an off-gas stream from the fermentation vessel. The carbon dioxide can be readily measured through use of a mass spectrometer or other suitable instrumental technique for measuring the components of the off-gas stream. In a preferred aspect, the glucose concentration is monitored by a real-time monitoring system using infrared spectroscopy. In another one aspect, the glucose concentration is monitored by a real-time monitoring system using near-infrared spectroscopy. The real time monitoring systems interface with equipment that controls the introduction of starch material into the fermentation broth to modulate the formation of glucose to a desired concentration in the fermentation broth.

During the fermentation process a sample of the fermentation medium can be taken to determine the amount of glucoamylase activity in the medium. The amount of glucoamylase activity in the medium can be referred to as extracellular glucoamylase activity as it corresponds to glucoamylase secreted from the engineered yeast. In some modes of measuring, the amount of glucoamylase activity in the medium can be determined by the amount of glucoamylase activity per amount of biomass per volume of medium.

Measuring the glucoamylase activity in the fermentation medium can be another way of reflecting the benefits of using yeast engineered to express a glucoamylase enzyme according to SEQ ID NO:1 or SEQ ID NO:4. Such a test can be carried out by using a fermentation medium made from a low DE feedstock, high DE feedstock, or anything in between. During the fermentation process a sample of medium is taken and the biomass amount and the enzyme activity are determined. As used herein "biomass" refers to the weight of the engineered yeast, which can be measured in grams of dried cell weight per liter of medium (DCW/L).

In some modes of practice, the fermentation period is about 30 hours or greater, about 40 hours or greater, about 50 hours or greater, or about 60 hours or greater, such as a period of time in the range of about 40 to about 120 hours, or 50 to about 110 hours.

The fermentation product (also referred to herein as a "bio-derived product" or "bioproduct") can be any product that can be prepared by enzymatic degradation of a starch material by the glucoamylase, formation of glucose, and fermentation of glucose. In some aspects, the fermentation product is selected from the group consisting of: amino acids, organic acids, alcohols, diols, polyols, fatty acids, fatty acid alkyl esters (such as fatty acid methyl or ethyl esters (for example C6 to C12 fatty acid methyl esters (preferably C8 to C10 fatty acid methyl esters))), monacyl glycerides, diacyl glycerides, triacyl glycerides, and mixtures thereof. Preferred fermentation products are organic acids, amino acids, fatty acid alkyl esters (such as fatty acid methyl esters (for example C8 to C12 fatty acid methyl esters (preferably C8 to C10 fatty acid methyl esters))), and their salts thereof, and especially where the organic acid is selected from the group consisting of hydroxyl carboxylic acids (including mono-hydroxy and dihydroxy mono-, di-, and tri-carboxylic acids), monocarboxylic acids, dicarboxylic acids, and tricarboxylic acids and mixtures thereof. Examples of fermentation products that are prepared by the present process are organic acids or amino acids such as lactic acid, citric acid, malonic acid, hydroxy butyric acid, adipic acid, lysine, keto-glutaric acid, glutaric acid, 3-hydroxy-proprionic acid, succinic acid, malic acid, fumaric acid, itaconic acid, muconic acid, methacrylic acid, acetic acid, methyl hexanoate, methyl octanoate, methyl nonanoate, methyl decanoate, methyl dodecanoate, ethyl hexanoate, ethyl octanoate, ethyl nonanoate, ethyl decanoate, ethyl dodecanoate, and mixtures thereof and derivatives thereof and salts thereof. In a preferred aspect, a fermentation method of the disclosure produces ethanol as the bioproduct.

The fermentation product can have an excellent ratio of bioproduct (e.g., ethanol) to residual glucose, which is beneficial as it improves downstream processes, such as separation of components (e.g., ethanol) in the final fermentation medium. For example, the amount of glucose in the fermentation medium is 1.0 g/kg or less, 0.9 g/kg or less, 0.8 g/kg or less, 0.7 g/kg or less, 0.6 g/kg or less, 0.5 g/kg or less, 0.4 g/kg or less, 0.3 g/kg or less, or 0.2 g/kg or less, such as a glucose amount in the range of about 0.05 g/kg to about 1.0 g/kg, or about 0.05 g/kg to about 0.5 g/kg. The final fermentation medium can have an ethanol:glucose (wt/wt) ratio of about 70:1 (wt/wt) or greater, about 100:1 (wt/wt) or greater, about 150:1 (wt/wt) or greater, about 200:1 (wt/wt) or greater, about 250:1 (wt/wt) or greater, or about 300:1 (wt/wt) or greater, such as in the range of about 75:1 (wt/wt) to about 750:1 (wt/wt), or about 100:1 (wt/wt) to about 500:1 (wt/wt).

The fermentation product is recovered from the fermentation broth. The manner of accomplishing this will depend on the particular product. However, in some modes of practice, the organism is separated from the liquid phase, typically via a filtration step or centrifugation step, and the product recovered via, for example, distillation, extraction, crystallization, membrane separation, osmosis, reverse osmosis, or other suitable technique.

The present process provides the ability to make fermentation products on a production scale level with excellent yields and purity. In an aspect, the process is carried out in fermentation broth quantities of at least 25,000 gallons. In an aspect, the batch process is carried out in to produce batches of at least 25,000 gallons of final fermentation broth. In some aspects the process is a continuous process, performed in vessels of at least 200,000 gallons.

In some aspects, a genetically modified yeast expressing SEQ ID NO:1 or SEQ ID NO:4, or a variant thereof, can be used for conversion processes, such as for the production of dextrose for fructose syrups, specialty sugars and in alcohol and other end-product (e.g., organic acid, ascorbic acid, and amino acids). Production of alcohol from the fermentation of starch substrates using glucoamylases of the disclosure can include the production of fuel alcohol or potable alcohol.

Ethanol mass yield can be calculated by dividing the ethanol concentration by the total glucose consumed. Since glucose can be present as free glucose or tied up in oligomers, one needs to account for both. To determine the total glucose present at the beginning and end of fermentation, a total glucose equivalents measurement is determined. Total glucose equivalence measurement is as follows. Glucose is measured with HPLC using RI detection. Separation is completed with a Bio Rad 87H column using a 10 mM H2SO4 mobile phase. Glucose is measured in triplicate for each sample. An acid hydrolysis is performed in triplicate in 6% (v/v) trifluoroacetic acid at 121° C. for 15 minutes. The resulting glucose after hydrolysis is measured by the same HPLC method. The total glucose equivalents present in each sample is the amount of glucose measured after acid hydrolysis. The total glucose consumed is calculated by subtracting the total glucose equivalents present at the end of fermentation from the total glucose equivalents present at the beginning of the fermentation.

Use of the engineered yeast of the current disclosure may also provide benefits with regards to increased titers, reduced volatile organic acids (VOCs), and reduced fusel oil compounds (volatile organic acids, higher alcohols, aldehydes, ketones, fatty acids and esters).

The fermentation product may be first treated with one or more agents via a treatment system. The treated fermentation product can then be sent to a distillation system. In the distillation system, the fermentation product can be distilled and dehydrated into ethanol. In some aspects, the components removed from the fermentation medium include water, soluble components, oil and unfermented solids. Some of these components can be used for other purposes, such as for an animal feed product. Other co-products, for example, syrup can be recovered from the stillage.

The present disclosure also provides a method for the production of a food, feed, or beverage product, such as an alcoholic or non-alcoholic beverage, such as a cereal- or malt-based beverage like beer or whiskey, such as wine, cider, vinegar, rice wine, soya sauce, or juice, said method comprising the step of treating a starch and/or sugar containing plant material with a composition as described herein. In another aspect, the invention also relates to a kit comprising a glucoamylase of the current disclosure, or a composition as contemplated herein; and instructions for use of said glucoamylase or composition. The invention also relates to a fermented beverage produced by a method using the glucoamylase.

After the fermentation process is complete, materials present in the fermentation medium can be of use. In some aspects, after a fermentation process has been completed, or while a fermentation process is ongoing, some or all of a bioproduct can be removed from the fermentation medium to provide a refined composition comprising non-bioproduct solids. The non-bioproduct solids can include the non-natural yeast, feedstock material in the medium that is not utilized by the yeast, as well as fermentation co-products. These materials can provide sources of carbohydrates and proteins that are useful as supplements to improve the nutritional content of a feed composition. The feed material can be a co-product from a fermentation process such as stillage (whole stillage, thin stillage, etc.) or composition prepared therefrom including dried distillers grains (DDG), distillers dry grains with solubles (DDGS), distillers wet grains (DWG), and distillers solubles (DS).

A fermentation medium, optionally with some or all of the target bioproduct removed, can be further treated, such as to remove water, or to cause precipitation or isolation of the non-bioproduct solids from the medium. In some cases the medium is treated by freeze drying or oven drying. After treatment the refined composition may be in the form of, for example, a liquid concentrate, a semi-wet cake, or a dry solid. The refined composition can be used as a feed composition itself, or an ingredient in the preparation of a feed composition. In preferred preparations, the feed composition is a livestock feed composition such as for sheep, cattle, pigs, etc.

The solids in the fermentation medium can provide a source of one or more amino acids. Introduced into an animal feed, the fermentation co-product can provide an enhanced amino acid content with regard to one or more essential amino acids. Essential amino acids can include histidine, isoleucine, lysine, methionine, phenylalanine, threonine, and tryptophan. These amino acids can be present in the feed composition as free amino acids or can be derived from proteins or peptides rich in the amino acids. The solids in the fermentation medium can provide a source of one or more prebiotics, which are nondigestible food substances, such as nondigestible oligosaccharides, that selectively stimulate the growth of favorable species of bacteria in the gut, thereby benefitting the host. The solids in the fermentation medium can provide a source of phytases, β-glucanases, proteases, and xylanases.

Table 4 includes strains used in the experimental studies associated with the disclosure.

TABLE 4

| Strain ID | Strain Description |
|---|---|
| Strain 1 | Wild Type |
| Strain 1-1 | Ura3Δ |
| Strain 1-2 | 2× Mfa2-*R. oryzae* GA |
| Strain 1-3 | 4× Mfa2-*R. oryzae* GA |
| Strain 1-4 | 1× *R. microsporus* GA |
| Strain 1-5 | 2× *R. microsporus* GA |
| Strain 1-6 | 2× *R. microsporus* GA |
| Strain 1-7 | 4× *R. microsporus* GA |
| Strain 1-8 | 2× *R. delemar* GA |
| Strain 1-9 | 4× *R. delemar* GA |

Example 1

Screening a Diverse Library of Glucoamylase Enzymes for Growth on Starch

Heterologous expression of a functional glucoamylase in *Saccharomyces cerevisiae* was first demonstrated circa 1993, using the *Aspergillus niger* glucoamylase. Other uses of glucoamylase in *Saccharomyces cerevisiae* have been reported, but still represent only a very small fraction of the number of public sequence information for these proteins. To that aim, over 1,000 enzymes were expressed and tested from a diverse set of organisms to identify enzymes that confer the desired trait of high glucoamylase expression while maintaining ethanol rate, titer, and yield.

A DNA library was constructed containing 1037 genes encoding glucoamylases, alpha-amylases, amylopullulanases, or other starch hydrolyzing enzymes by cloning synthetically created open reading frames into a *Saccharomyces cerevisiae* episomal plasmid. The enzymes encoded by these genes were sourced from four distinct classes including: 1) enzymes that were annotated with a glucoamylase EC number (which included both glucoamylases and α-amylases), 2) enzymes that were annotated as having both α-1,6 and α-1,4 glycosidase activity 3) structural homologs of previously identified functional fungal glucoamylases expressed in *Saccharomyces cerevisiae*, and finally 4) starch hydrolyzing enzymes from ruminant gut microbiomes. Each enzyme in the library was screened with its native leader as well as one substituted with the *Saccharomyces cerevisiae* Mfα2 leader. In total, 1,773 plasmids were successfully transformed into Strain 1-1 (described in previous application). Resulting transformants were tested for growth on starch containing media, using iodine staining to reveal zones of clearing. A total of 245 strains were able to produce zones of clearing, indicating that they contained plasmids with genes encoding heterologous enzymes capable of generating starch hydrolyzing activity when expressed in a yeast. These 245 were further screened for ethanol production as described below. The remaining genes encoded by the remaining 1528 plasmids were deemed not to be sufficiently active to warrant further testing.

Secondary Screening for Ethanol Production in Deep Well Microtiters

Ethanol production was measured using deep well microtiter plates containing 0.5 mL of media. The fermentation medium consists of 725 g partially hydrolyzed corn starch in the form of liquifact, 150 g filtered light steep water, 125 g sterile water, 25 g glucose, and 1 g urea. Partially hydrolyzed corn starch is provided by Cargill's Eddyville, Iowa corn wet mill (DS 30-37%, DE 5-15). Light steep water is also provided from Cargill's Eddyville, Iowa corn wet mill (free available nitrogen 2000-2500 ppm). Light steep water is centrifuged at 8,000 RPM, and the resulting supernatant is filter sterilized using 0.2 micron filters to produce filtered light steep water. Strains are inoculated to an $OD_{600}$ of 0.1 and the plate is incubated at 30° C. with shaking in an orbital shake at 1000 rpm. Samples are taken and analyzed for relevant metabolite concentrations at the end of fermentation by HPLC.

Selected results from the screening of the 245 strains is shown in Table 5. Most of the strains did not demonstrate commercially relevant ethanol titers (e.g., *Aspergillus kawachii, Aspergillus terreus, Thermomyces lanuginosus*, and Mfα2-*Neurospora crassa* are representative of such strains). However, two strains (*Rhizopus delemar* and *Rhizopus* microspores) demonstrated ethanol titers greater than commercially relevant strains known in the art (Mfa2-*Rhizopus oryzae* and *Saccharomycopsis fibuligera*).

TABLE 5

| Enzyme Source, Accession # | SEQ ID NO | Ethanol titer (g/L) at 61.25 hours |
|---|---|---|
| *Rhizopus delemar*, I1BGP8 | SEQ ID NO 7 | 100.08 |
| *Rhizopus microsporus*, A0A0C7BD37 | SEQ ID NO 8 | 107.82 |
| Mfα2-*Rhizopus oryzae*, Q2VC81 | SEQ ID NO 9 | 99.50 |
| *Saccharomycopsis fibuligera*, Q8TFE5 | SEQ ID NO 10 | 89.64 |
| *Aspergillus kawachii*, G7XVA6 | SEQ ID NO 11 | 33.70 |
| *Aspergillus terreus*, Q0CPK9 | SEQ ID NO 12 | 34.20 |
| *Thermomyces lanuginosus*, Q58HN1 | SEQ ID NO 13 | 35.00 |
| Mfα2-*Neurospora crassa*, A0A0B0E9D9 | SEQ ID NO 14 | 37.90 |

Example 2

Construction of Strains Expressing the MFalpha2-*R. oryzae* GA.

Creation of a ura3Δ auxotrophic base strain is previously described in (CAR0233P1 Strain 1-3), referred to as Strain 1-1 herein. Strain 1-1 is transformed with SEQ ID NO: 15 and SEQ ID NO: 16. SEQ ID NO: 15 contains the following elements: homology to integration locus A (3986 bp), a ScTDH3 promoter (992-1673 bp), a *Rhizopus oryzae* glucoamylase with modified signal sequence (1680-3476 bp), a ScCYC1 terminator (3485-3708 bp), a loxP recombination site (3717-3750 bp), a ScURA3 promoter (3751-4257 bp), the upstream portion of the ScURA3 (4258-4861 bp). SEQ ID NO: 16 contains the following elements: downstream portion of the ScURA3 (7-606 bp), a ScURA3 terminator (607-927 bp), a loxP recombination site (928-961 bp), a ScPGK1 promoter (968-1554 bp), a *Rhizopus oryzae* glucoamylase with modified signal sequence (1561-3357 bp), a ScGAL10 terminator (3366-3836 bp), and homology to integration locus A (3838-4748 bp). Transformants are selected on synthetic complete media lacking uracil. (ScD-Ura). Resulting transformants are streaked for single colony isolation on ScD-Ura. A single colony is selected. Correct integration of SEQ ID NO: 15 and SEQ ID NO: 16 into one allele of integration locus A is verified by PCR in the single colony. A PCR verified isolate is designated Strain 1-2 (yNS220).

Strain 1-2 is transformed with SEQ ID NO: 17, 18 and 19. SEQ ID NO: 17 contains the following elements: homology to integration locus A (3-986 bp), a ScTDH3 promoter (9921673 bp). SEQ ID NO: 18 contains the following elements: a ScTDH3 promoter (6-687 bp), a *Rhizopus oryzae* glucoamylase with modified signal sequence (694-2490), a ScCYC1 terminator (2499-2722 bp), a loxP recombination site (2731-2674 bp), a ScTEF1 promoter (2765-3220 bp), and the upstream portion of the *Aspergillus nidulans* acetamidase (3221-4260). SEQ ID NO: 19 contains the following elements: the downstream portion of the *Aspergillus nidulans* acetamidase (7-1032 bp), a ScADH1 terminator (1033-1335 bp), a loxP recombination site (1336-1369 bp), a ScPGK1 promoter (1376-1962 bp), a *Rhizopus oryzae* glucoamylase with modified signal sequence (1969-3765 bp), a ScGAL10 terminator (3774-4244 bp), and homology to integration locus A (4246-5008 bp). Transformants are selected on Yeast Nitrogen Base (without ammonium sulfate or amino acids) containing 20 g/L glucose and 1 g/L acetamide as the sole nitrogen source. Resulting transformants are streaked for single colony isolation on Yeast Nitrogen Base (without ammonium sulfate or amino acids) containing 20 g/l glucose and 1 g/L acetamide as the sole nitrogen source. A single colony is selected. Correct integration of SEQ ID NO 17, 18 and 19 into the second allele of locus A is verified by PCR in the single colony. A PCR verified isolate is designated Strain 1-3.

Example 3

Construction of Strains Expressing the *Rhizopus microsporus* GA.

Strain 1-1 is transformed with SEQ ID NO: 20 and SEQ ID NO: 21. SEQ ID NO: 20 contains the following elements: homology to integration locus A (3-986 bp), a ScTDH3 promoter (992-1673 bp), a *Rhizopus microsporus* glucoamylase (1680-3497 bp), a ScCYC1 terminator (3506-3729 bp), a loxP recombination site (3738-3771 bp), a ScURA3 promoter (3772-4278 bp), the upstream portion of the ScURA3

(4279-4882 bp). SEQ ID NO: 21 contains the following elements: A portion of the ScURA3 promoter (11-446), a ScURA3 (447-1250 bp), a ScURA3 terminator (1251-1570 bp), a loxP recombination site (1571-1604 bp), and homology to integration locus A (1613-1790 bp). Transformants are selected on synthetic complete media lacking uracil. (ScD-Ura). Resulting transformants are streaked for single colony isolation on ScD-Ura. A single colony is selected. Correct integration of SEQ ID NO: 20 and SEQ ID NO: 21 into one allele of integration locus A is verified by PCR in the single colony. A PCR verified isolate is designated Strain 1-4.

Strain 1-4 is transformed with SEQ ID NO: 22 and SEQ ID NO: 23. SEQ ID NO: 22 contains the following elements: homology to integration locus A (1-193 bp), a ScTDH3 promoter (199-880 bp), a *Rhizopus microsporus* glucoamylase (887-2704 bp), a ScCYC1 terminator (2713-2936 bp), a loxP recombination site (2945-2978 bp), a ScTEF1 promoter (2979-3434 bp), and the upstream portion of the *Aspergillus nidulans* acetamidase (3435-4474 bp). SEQ ID NO 23 contains the following elements: the downstream portion of the *Aspergillus nidulans* acetamidase (1-1498 bp), a ScTEF1 terminator (1499-1658 bp), a loxP recombination site (1692-1659 bp), and homology to integration locus A (1701-1878). Transformants are selected on Yeast Nitrogen Base (without ammonium sulfate or amino acids) containing 20 g/L glucose and 1 g/L acetamide as the sole nitrogen source. Resulting transformants are streaked for single colony isolation on Yeast Nitrogen Base (without ammonium sulfate or amino acids) containing 20 g/l glucose and 1 g/L acetamide as the sole nitrogen source. A single colony is selected. Correct integration of SEQ ID NO: 22 and SEQ ID NO: 23 into the second allele of locus A is verified by PCR in the single colony. A PCR verified isolate is designated Strain 1-5.

Strain 1-1 is transformed with SEQ ID NO: 20 and SEQ ID NO: 24. SEQ ID NO: 24 contains the following elements: downstream portion of the ScURA3 (7-606 bp), a ScURA3 terminator (607-927 bp), a loxP recombination site (928-961 bp), a ScPGK1 promoter (9681554 bp), a *Rhizopus microsporus* glucoamylase (1561-3378 bp), a ScGAL10 terminator (3387-3857 bp), and homology to integration locus A (3859-4823 bp). Transformants are selected on synthetic complete media lacking uracil. (ScD-Ura). Resulting transformants are streaked for single colony isolation on ScD-Ura. A single colony is selected. Correct integration of SEQ ID NO: 20 and SEQ ID NO: 24 into one allele of integration locus A is verified by PCR in the single colony. A PCR verified isolate is designated Strain 1-6.

Strain 1-6 is transformed with SEQ ID NO: 22 and SEQ ID NO: 25. SEQ ID NO: 25 contains the following elements: the downstream portion of the *Aspergillus nidulans* acetamidase (7-1032 bp), a ScADH1 terminator (1033-1335 bp), a loxP recombination site (1336-1369 bp), a ScPGK1 promoter (1376-1962 bp), a *Rhizopus microsporus* glucoamylase (1969-3786 bp), a ScGAL10 terminator (3795-4265 bp), and homology to integration locus A (4267-4684 bp). Transformants are selected on Yeast Nitrogen Base (without ammonium sulfate or amino acids) containing 20 g/L glucose and 1 g/L acetamide as the sole nitrogen source. Resulting transformants are streaked for single colony isolation on Yeast Nitrogen Base (without ammonium sulfate or amino acids) containing 20 g/l glucose and 1 g/L acetamide as the sole nitrogen source. A single colony is selected. Correct integration of SEQ ID NO: 22 and SEQ ID NO: 25 into the second allele of locus A is verified by PCR in the single colony. A PCR verified isolate is designated Strain 1-7.

Example 4

Construction of Strains Expressing the *Rhizopus delemar* GA.

Strain 1-1 is transformed with SEQ ID NO: 26 and SEQ ID NO: 27. SEQ ID NO: 26 contains the following elements: homology to integration locus A (3-986 bp), a ScTDH3 promoter (992-1673 bp), a *Rhizopus delemar* glucoamylase (1698-3494 bp), a ScCYC1 terminator (3503-3726 bp), a loxP recombination site (3735-3768 bp), a ScURA3 promoter (3769-4275 bp), the upstream portion of the ScURA3 (4276-4879 bp). SEQ ID NO: 27 contains the following elements: downstream portion of the ScURA3 (7-606 bp), a ScURA3 terminator (607-927 bp), a loxP recombination site (928-961 bp), a ScPGK1 promoter (968-1554 bp), a *Rhizopus delemar* glucoamylase (1561-3375 bp), a ScGAL10 terminator (3384-3854 bp), and homology to integration locus A (3856-4820). Transformants are selected on synthetic complete media lacking uracil. (ScD-Ura). Resulting transformants are streaked for single colony isolation on ScDUra. A single colony is selected. Correct integration of SEQ ID NO: 26 and SEQ ID NO: 27 into one allele of integration locus A is verified by PCR in the single colony. A PCR verified isolate is designated Strain 1-8.

Strain 1-8 is transformed with SEQ ID NO: 28 and SEQ ID NO: 29. SEQ ID NO: 28 contains the following elements: homology to integration locus A (1-986 bp), a ScTDH3 promoter (992-1673 bp), a *Rhizopus delemar* glucoamylase (1680-3494 bp), a ScCYC1 terminator (3503-3726 bp), a loxP recombination site (3735-3768 bp), a ScTEF1 promoter (3769-4224 bp), and the upstream portion of the *Aspergillus nidulans* acetamidase (4225-5264 bp). SEQ ID NO: 29 contains the following elements: the downstream portion of the *Aspergillus nidulans* acetamidase (7-1032 bp), a ScADH1 terminator (1033-1335 bp), a loxP recombination site (1336-1369 bp), a ScPGK1 promoter (1376-1962 bp), a *Rhizopus delemar* glucoamylase (1969-3783 bp), a ScGAL10 terminator (3792-4262 bp), and homology to integration locus A (4264-5026 bp). Transformants are selected on Yeast Nitrogen Base (without ammonium sulfate or amino acids) containing 20 g/L glucose and 1 g/L acetamide as the sole nitrogen source. Resulting transformants are streaked for single colony isolation on Yeast Nitrogen Base (without ammonium sulfate or amino acids) containing 20 g/l glucose and 1 g/L acetamide as the sole nitrogen source. A single colony is selected. Correct integration of SEQ ID NO: 28 and SEQ ID NO: 29 into the second allele of locus A is verified by PCR in the single colony. A PCR verified isolate is designated Strain 1-9.

Example 5

Characterization of Strains in 32% DS Corn Mash at 30° C. (Test #1 and #2).

Strain 1, 1-3, 1-5, 1-7, 1-9 are struck to a YPD plate and incubated at 30° C. until single colonies are visible (1-2 days). Cells from the YPD plate are scraped into pH 7.0 phosphate buffer and the optical density (OD600) is measured. Optical density is measured at wavelength of 600 nm with a 1 cm path length using a model Genesys20 spectrophotometer (Thermo Scientific). A shake flask is inoculated with the cell slurry to reach an initial OD600 of 0.1. Immediately prior to inoculating the following materials are added to each flask: 50 grams of liquified corn mash (32% DS, DE 30+/−2) is added to a 250 mL baffled shake flask sealed with air-lock containing 4 mls of sterilized canola oil, 190 ul of 500 g/L filter-sterilized urea, and 2.5 ul of 100 mg/ml of filter sterilized ampicillin.

0.324 AGU/g DS (70 µl of a 1:10 dilution) of glucoamylase (Spirizyme Fuel HS, Novozymes) is added to flasks containing the control Strain 1, and either zero or 0.097 AGU/g DS (21 µL of a 1:10 dilution of glucoamylase (Spirizyme Fuel HS™, Novozymes is added to the remaining flasks depending on the "Test". Spirizyme Fuel HS™ is estimated to have approximately 769 AGU/g enzyme, however over time the activity can change 10-20% (i.e., the activity of the enzyme typically decreases over time). Duplicate flasks for each strain are incubated at 30° C. with shaking in an orbital shaker at 100 rpm for approximately 48 hours. At 48 hours, 1 ml samples are taken and analyzed for ethanol and glucose concentrations in the broth by high performance liquid chromatography with refractive index detector. Selected results are shown in Table 6.

TABLE 6

| | Test #1 Final EtOH titer (g/kg) | Test #1 Residual Glucose (g/kg) |
|---|---|---|
| Strain 1, with 0.324 AGU/g DS | 133.6 +/− 1.6 | 0.4 +/− 0.1 |
| Strain 1-3, no supplementation | 132.5 +/− 0.3 | 0.2 +/− 0.0 |
| Strain 1-5, no supplementation | 120.9 +/− 1.3 | 0.5 +/− 0.1 |
| Strain 1-7, no supplementation | 134.1 +/− 4.8 | 0.2 +/− 0.0 |
| Strain 1-9, no supplementation | 119.8 +/− 1.9 | 0.9 +/− 0.0 |
| | Test #2 Final EtOH titer (g/kg) | Test #2 Residual Glucose (g/kg) |
| Strain 1, with 0.324 AGU/g DS | 133.6 +/− 1.6 | 0.4 +/− 0.1 |
| Strain 1-3, no supplementation | 130.7 +/− 2.7 | 0.2 +/− 0.1 |
| Strain 1-5, no supplementation | 132.9 +/− 0.2 | 0.3 +/− 0.0 |
| Strain 1-7, no supplementation | 135.0 +/− 1.2 | 0.3 +/− 0.0 |
| Strain 1-9, no supplementation | 131.9 +/− 0.5 | 0.2 +/− 0.1 |

Example 6

Characterization of Strains in 32% DS Corn Mash at 33.3° C. (Test #3 and #4).

Strain 1, 1-3, 1-5, 1-7, 1-9 are struck to a YPD plate and incubated at 30° C. until single colonies are visible (1-2 days). Cells from the YPD plate are scraped into pH 7.0 phosphate buffer and the optical density ($OD_{600}$) is measured. Optical density is measured at wavelength of 600 nm with a 1 cm path length using a model Genesys20 spectrophotometer (Thermo Scientific). A shake flask is inoculated with the cell slurry to reach an initial $OD_{600}$ of 0.1. Immediately prior to inoculating the following materials are added to each flask: 50 grams of liquified corn mash is added to a 250 mL baffled shake flask sealed with air-lock containing 4 mls of sterilized canola oil, 190 ul of 500 g/L filter-sterilized urea, and 2.5 ul of 100 mg/ml of filter sterilized ampicillin 0.324 AGU/g DS (70 µl of a 1:10 dilution) of glucoamylase (Spirizyme Fuel HS™, Novozymes) is added to flasks containing the control Strain 1, and either zero or 0.097 AGU/g DS (21 µl of a 1:10 dilution) of glucoamylase (Spirizyme Fuel HS™, Novozymes) is added to the remaining flasks, depending on the "Test". Spirizyme Fuel HS™ is estimated to have approximately 326 AGU/g enzyme. Duplicate flasks for each strain are incubated at 33.3° C. with shaking in an orbital shake at 100 rpm for approximately 48 hours. At 48 hours, 1 ml samples are taken and analyzed for ethanol and glucose concentrations in the broth by high performance liquid chromatography with refractive index detector. Selected results are shown in Table 7.

TABLE 7

| | Test #3 Final EtOH titer (g/kg) | Test #3 Residual Glucose (g/kg) |
|---|---|---|
| Strain 1, with 0.324 AGU/g DS | 135.8 +/− 0.4 | 0.8 +/− 0.1 |
| Strain 1-3, no supplementation | 124.1 +/− 4.4 | 6.0 +/− 0.0 |
| Strain 1-5, no supplementation | 132.8 +/− 1.2 | 0.2 +/− 0.0 |
| Strain 1-7, no supplementation | 131.2 +/− 2.4 | 2.6 +/− 0.2 |
| Strain 1-9, no supplementation | 132.9 +/− 1.2 | 0.2 +/− 0.0 |
| | Test #4 Final EtOH titer (g/kg) | Test #4 Residual Glucose (g/kg) |
| Strain 1, with 0.324 AGU/g DS | 135.8 +/− 0.4 | 0.8 +/− 0.1 |
| Strain 1-3 with 0.097 AGU/g DS | 129.5 +/− 3.6 | 3.3 +/− 0.0 |
| Strain 1-5, with 0.097 AGU/g DS | 132.8 +/− 0.3 | 0.4 +/− 0.2 |
| Strain 1-7, with 0.097 AGU/g DS | 129.5 +/− 0.9 | 7.9 +/− 0.2 |
| Strain 1-9, with 0.097 AGU/g DS | 134.5 +/− 1.5 | 0.9 +/− 0.1 |

Example 7

Characterization of Strains in 34% DS Corn Mash at 33.3° C.

Strains 1, 1-3, 1-6, and 1-9 are struck to a YPD plate and incubated at 30° C. until single colonies are visible (1-2 days). Cells from the YPD plate are scraped into pH 7.0 phosphate buffer and the optical density ($OD_{600}$) is measured. Optical density is measured at wavelength of 600 nm with a 1 cm path length using a model Genesys20 spectrophotometer (Thermo Scientific). A shake flask is inoculated with the cell slurry to reach an initial $OD_{600}$ of 0.1. Immediately prior to inoculating the following materials are added to each flask: 50 grams of liquified corn mash is added to a 250 mL baffled shake flask sealed with air-lock containing 4 mls of sterilized canola oil, 190 ul of 500 g/L filter-sterilized urea, and 2.5 ul of 100 mg/ml of filter sterilized ampicillin 0.324 AGU/g DS (70 µl of a 1:10 dilution) of glucoamylase (Spirizyme Fuel HS™, Novozymes) is added to flasks containing the control Strain 1, and either zero or 0.032 AGU/g DS, 0.065 AGU/g DS, 0.097 AGU/g DS, or 0.162 AGU/gDS. (7 µl, 14 µl, 21 µl, or 35 µl of a 1:10 dilution) is added to the remaining flasks. Spirizyme Fuel HS™ is estimated to have approximately 326 AGU/g enzyme. Duplicate flasks for each strain are incubated at 33.3° C. with shaking in an orbital shake at 100 rpm for approximately 48 hours. At various intervals, the flasks are opened and samples are analyzed for ethanol and glucose concentrations in the broth by high performance liquid chromatography with refractive index detector. Selected results are shown in Table 8.

TABLE 8

| | Final EtOH titer (g/kg) | Residual Glucose (g/kg) |
|---|---|---|
| Strain 1, 0.324 AGU/g DS dose | 137.0 +/− 2.8 | 1.2 +/− 0.3 |
| Strain 1-3, no supplementation | 123.2 +/− 1.1 | 12.1 +/− 0.5 |
| Strain 1-3, 0.032 AGU/g DS dose | 122.3 +/− 3.2 | 14.8 +/− 0.8 |
| Strain 1-3, 0.065 AGU/g DS dose | 123.4 +/− 4.2 | 16.8 +/− 0.0 |
| Strain 1-3, 0.097 AGU/g dose DS | 130.1 +/− 1.4 | 14.6 +/− 0.3 |
| Strain 1-6, no GA dose | 133.9 +/− 5.1 | 0.2 +/− 0.1 |
| Strain 1-6, 0.032 AGU/g dose DS | 137.5 +/− 3.7 | 0.6 +/− 0.0 |
| Strain 1-6, 0.097 AGU/g dose DS | 138.8 +/− 0.2 | 1.0 +/− 0.0 |
| Strain 1-6, 0.162AGU/gDS dose | 138.4 +/− 2.8 | 2.0 +/− 0.7 |
| Strain 1-9, no supplementation | 135.1 +/− 0.3 | 1.2 +/− 0.1 |
| Strain 1-9, 0.032 AGU/g DS dose | 136.2 +/− 5.4 | 1.4 +/− 0.2 |

TABLE 8-continued

| | Final EtOH titer (g/kg) | Residual Glucose (g/kg) |
|---|---|---|
| Strain 1-9, 0.097 AGU/g DS dose | 135.7 +/− 1.0 | 4.8 +/− 0.9 |
| Strain 1-9, 0.162 AGU/gDS dose | 136.0 +/− 2.0 | 6.1 +/− 0.3 |

Example 8

Characterization of a Strain in 32% DS Corn Mash Having a DE of 30+/−2 at a Temperature of 30° C.

A strain is struck to a YPD plate (20 g/L yeast peptone, 10 g/L yeast extract, 20 g/L glucose, and 20 g/L agar) and incubated at 30° C. until single colonies are visible (1-2 days). Cells from the YPD plate are scraped into pH 7.0 phosphate buffer to create a cell slurry and the optical density ($OD_{600}$) is measured. Optical density is measured at wavelength of 600 nm with a 1 cm path length using a model Genesys20 spectrophotometer (Thermo Scientific). A shake flask is inoculated with the cell slurry to reach an initial $OD_{600}$ of 0.1 Immediately prior to inoculating the following materials are added to each flask: 50 grams of liquified corn mash (32% DS, DE 30) is added to a 250 mL baffled shake flask sealed with air-lock containing 4 mls of sterilized canola oil, 190 ul of 500 g/L filter-sterilized urea, and 2.5 ul of 100 mg/ml of filter sterilized ampicillin. The shake flask, airlock, canola oil is weighed prior to the addition of the fermentation media and cells, which is subtracted from the total weight of the flask to give the starting media volume. At various time points in the fermentation, the flasks are removed and the weight recorded. The mass loss (grams) at any timepoint is calculated by subtracting the mass at T1 from the original mass at T0. The mass loss (grams) is converted to a mass loss (percentage) by dividing the mass loss at any given time point by the original starting mass. The percentage mass loss can be converted to g/kg ethanol by the following equation (the starting mass of the fermentation media. Ethanol (g/kg)=(Percent mass loss+0.0016)/0.0009/1.042.

EXEMPLARY EMBODIMENTS

A. An engineered yeast comprising an exogenous nucleic acid encoding a glucoamylase comprising a sequence having 81% or greater sequence identity to SEQ ID NO:1, wherein the yeast is capable of producing ethanol at a rate of 1 g/L*h or greater during a fermentation process.

B. An engineered yeast comprising an exogenous nucleic acid encoding a glucoamylase comprising a sequence having 81% or greater sequence identity to SEQ ID NO:1, wherein the yeast is capable of producing (a) at least 70 g/kg of ethanol in a fermentation medium made from a glucose polymer-containing feedstock having (i) a DE of not greater than 50.

C. An engineered yeast comprising an exogenous nucleic acid encoding a glucoamylase comprising a sequence having 81% or greater sequence identity to SEQ ID NO:1, wherein the yeast is capable of producing (a) at least 70 g/kg of ethanol in a fermentation medium made from corn mash having a DE of 30+/−2, wherein the fermentation medium comprises 32% dry wt corn, and a pH 5.8, 35 ppm CaCl, 1900 ppm urea, 5 ppm ampicillin, wherein the staring yeast concentration is 0.1 (OD600), and fermentation is carried out at 48 hrs at 30° C. with agitation.

D. The engineered yeast of any of embodiments A-C wherein the glucoamylase comprises a sequence having 85% or greater sequence identity to SEQ ID NO:1.

E. The engineered yeast of embodiment D wherein the glucoamylase comprises a sequence having 90% or greater sequence identity to SEQ ID NO:1.

F. The engineered yeast of embodiment E wherein the glucoamylase comprises a sequence having 95%, 96%, 97%, 98%, or 99%, or greater sequence identity to SEQ ID NO:1.

G. An engineered yeast comprising an exogenous nucleic acid encoding a glucoamylase comprising a sequence having 97% or greater sequence identity to SEQ ID NO:4, wherein the yeast is capable of producing ethanol at a rate of 1 g/L*h or greater during a fermentation process.

H. An engineered yeast comprising an exogenous nucleic acid encoding a glucoamylase comprising a sequence having 97% or greater sequence identity to SEQ ID NO:4, wherein the yeast is capable of producing (a) at least 70 g/kg of ethanol in a fermentation medium made from a glucose polymer-containing feedstock having (i) a DE of not greater than 50.

I. An engineered yeast comprising an exogenous nucleic acid encoding a glucoamylase comprising a sequence having 81% or greater sequence identity to SEQ ID NO:4, wherein the yeast is capable of producing (a) at least 70 g/kg of ethanol in a fermentation medium made from corn mash having a DE of 30, wherein the corn mash is present in a fermentation medium having 32% wt corn mash, and a pH 5.8, 35 ppm CaCl, 1900 ppm urea, 5 ppm ampicillin, wherein the staring yeast concentration is 0.1 (OD600), and fermentation is carried out at 48 hrs at 30° C. with agitation.

J. The engineered yeast of any of embodiments G-I wherein the glucoamylase comprises a sequence having 98% or greater sequence identity to SEQ ID NO:4.

K. The engineered yeast of embodiment J wherein the glucoamylase comprises a sequence having 99% or greater sequence identity to SEQ ID NO:4.

L. The engineered yeast of any of the above embodiments wherein there are 2-8 copies of the exogenous nucleic acid in the cell.

M. The engineered yeast of embodiment L wherein there are 2-6 copies of the exogenous nucleic acid in the cell.

N. The engineered yeast of embodiment M wherein there are 4 copies of the exogenous nucleic acid in the cell.

O. The engineered yeast of any of the above embodiments wherein the exogenous nucleic acid is under the control of a promoter selected from the group consisting of a phosphoglycerate kinase (PGK) promoter nucleic acid sequence, cytochrome c promoter (pCYC) nucleic acid sequence, translational elongation factor promoter (pTEF) nucleic acid sequence, glyceraldehyde-3phosphate dehydrogenase promoter (pGPD/TDH3) nucleic acid sequence, the phosphoglycerate kinase promoter (PGK) nucleic acid sequence, and the alcohol dehydrogenase promoter (pADH) nucleic acid sequence.

P. The engineered yeast of any of the above embodiments which is a species of *Saccharomyces.*

Q. The engineered yeast of embodiment P which is *Saccharomyces cerevisiae.*

R. The engineered yeast of any of the above embodiments which is tolerant to growth in fermentation medium having a concentration of ethanol of greater than 90 g/L.

S. The engineered yeast of any of the above embodiments which is tolerant to growth at temperatures in the range of greater than 31° C.-35° C.

T. The engineered yeast of embodiment S which is tolerant to growth in at temperatures in the range of greater than 32° C.-34° C.

U. The engineered yeast of any one of the above embodiments that produces a greater amount of ethanol than a parent strain that does not include the exogenous nucleic acid under the same fermentation conditions.

V. A fermentation method for producing a fermentation product, comprising a step of: forming a fermentation medium from a glucose polymer-containing feedstock; and fermenting the fermentation medium using an engineered yeast comprising an exogenous nucleic acid encoding a glucoamylase comprising a sequence having 81% or greater sequence identity to SEQ ID NO:1, wherein fermenting produces the bioproduct.

W. A fermentation method for producing a fermentation product, comprising a step of: forming a fermentation medium from a glucose polymer-containing feedstock; and fermenting the fermentation medium using an engineered yeast comprising an exogenous nucleic acid encoding a glucoamylase comprising a sequence having 97% or greater sequence identity to SEQ ID NO:4, wherein fermenting produces the bioproduct.

X. The fermentation method of embodiments V or W wherein the glucose polymer-containing feedstock or the fermentation medium, at the beginning of fermentation, has a DE of about 50 or less.

Y. The fermentation method of embodiments V or W wherein the fermentation medium, at the beginning of fermentation, has a glucose concentration of about 30 g/kg or less.

Z. The fermentation method of embodiments V or W wherein glucose polymer-containing feedstock comprises glucose polymer having a degree of polymerization of 4 or greater and present in an amount of 75% weight or greater total fermentable carbohydrates in the feedstock.

AA. The fermentation method of any of embodiments V-Z wherein glucose polymer-containing feedstock is obtained from corn.

BB. The fermentation method of embodiment AA wherein glucose polymer-containing feedstock is obtained from corn mash.

CC. The fermentation method of any of embodiments V-BB wherein fermenting is carried out for a fermentation time of at least 30 hours.

DD. The fermentation method of embodiment CC wherein fermenting is carried out for a fermentation time in the range of 30-100 hours.

EE. The fermentation method of embodiment DD wherein fermenting is carried out for a fermentation time in the range of 40-60 hours.

FF. The fermentation method of any of embodiments V-EE wherein said fermenting is carried out at a temperature in the range of 31° C. to 35° C. for most or all of a fermentation period.

GG. The fermentation method of embodiment FF wherein the fermenting is carried out at a temperature in the range of 32° C. to 34° C. for most or all of the fermentation period.

HH. The fermentation of any of embodiments V-GG wherein ethanol is produced to a concentration of 70 g/L or greater in the medium.

II. The fermentation of embodiment HH wherein ethanol is produced to a concentration of 90 g/L or greater in the medium.

JJ. The method of embodiment II wherein said fermenting provides ethanol in the range of 90 g/L to 150 g/L.

KK. The method of embodiment JJ wherein said fermenting provides ethanol in the range of 110 g/L to 150 g/L.

LL. The fermentation method of any of embodiments V-KK wherein the fermentation medium has an amount of glucose of not greater than 1.0 g/L at the end of the fermentation period.

MM. The fermentation method of embodiment LL wherein the fermentation medium has an amount of glucose of not greater than 0.8 g/L at the end of the fermentation period.

NN. The fermentation method of any of embodiments V-MM comprising adding supplemental glucoamylase to the feedstock, or supplemental glucoamylase to the medium during the fermentation period.

OO. An engineered yeast comprising an exogenous nucleic acid encoding a glucoamylase comprising a sequence having 81% or greater sequence identity to SEQ ID NO:1, wherein the yeast is capable of producing at least 70 g/kg of ethanol in the fermentation process of Example 8.

PP. An engineered yeast comprising an exogenous nucleic acid encoding a glucoamylase comprising a sequence having 97% or greater sequence identity to SEQ ID NO:4, wherein the yeast is capable of producing at least 70 g/kg of ethanol in the fermentation process of Example 8.

What is claimed is:

1. An engineered yeast comprising an exogenous nucleic acid encoding a glucoamylase comprising a sequence having 97% or greater sequence identity to SEQ ID NO:4, wherein the yeast is capable of producing ethanol at a rate of 1 g/L*h or greater during a fermentation process.

2. The engineered yeast of claim 1, wherein the glucoamylase comprises a sequence having 98% or greater sequence identity to SEQ ID NO:4.

3. The engineered yeast of claim, wherein the glucoamylase comprises a sequence having 99% or greater sequence identity to SEQ ID NO:4.

4. The engineered yeast of claim 1, wherein there are 2-8 copies of the exogenous nucleic acid in the cell.

5. The engineered yeast of claim 1, wherein the engineered yeast a *Saccharomyces cerevisiae* yeast.

6. The engineered yeast of claim 1, wherein the yeast is tolerant to growth in a fermentation medium having a concentration of ethanol of greater than 90 g/L.

7. The engineered yeast of claim 1, wherein the yeast is tolerant to growth at temperatures in the range of greater than 31° C.-35° C.

8. A fermentation method for producing a bioproduct, comprising:

forming a fermentation medium from a glucose polymer-containing feedstock; and fermenting the fermentation medium using an engineered yeast comprising an exogenous nucleic acid encoding a glucoamylase comprising a sequence having 97% or greater sequence identity to SEQ ID NO:4, wherein fermenting produces a bioproduct.

9. The fermentation method of claim 8, wherein the glucose polymer-containing feedstock or the fermentation medium, at the beginning of fermentation, has a dextrose equivalent ("DE") of about 50 or less.

10. The fermentation method of claim 8, wherein the glucose polymer-containing feedstock comprises glucose polymer having a degree of polymerization of 4 or greater and present in an amount of 75% weight or greater total fermentable carbohydrates in the feedstock.

11. The fermentation of claim 8, wherein ethanol is produced to a concentration of 70 g/L or greater in the medium.

12. The fermentation method of claim 8, comprising adding supplemental glucoamylase to the feedstock, or supplemental glucoamylase to the medium during the fermentation period.

13. An engineered yeast comprising an exogenous nucleic acid encoding a glucoamylase comprising (i) a sequence at least 97% identical to amino acids 26-604 of SEQ ID NO:4 and (ii) a heterologous N-terminal signal sequence.

14. The engineered yeast of claim 13, wherein the yeast is capable of producing ethanol at a rate of 1 g/L*h or greater during a fermentation process.

15. The engineered yeast of claim 13, wherein the glucoamylase comprises a sequence at least 98% identical to amino acids 26-604 of SEQ ID NO:4.

16. The engineered yeast of claim 13, wherein the glucoamylase comprises a sequence at least 99% identical to amino acids 26-604 of SEQ ID NO:4.

17. The engineered yeast of claim 13, wherein the heterologous N-terminal signal sequence is selected from the group consisting of Sc FAKS, Sc AKS, Sc MFal, Sc IV, Gg LZ, and Hs SA signal sequences.

18. The engineered yeast of claim 13, wherein the yeast is a *Saccharomyces cerevisiae* yeast.

* * * * *

UNITED STATES PATENT AND TRADEMARK OFFICE
CERTIFICATE OF CORRECTION

PATENT NO. : 11,939,619 B2
APPLICATION NO. : 17/657241
DATED : March 26, 2024
INVENTOR(S) : Chris Miller et al.

It is certified that error appears in the above-identified patent and that said Letters Patent is hereby corrected as shown below:

In the Specification

In Column 2, Line 53 delete "(OD600)" and insert -- ($OD_{600}$) --, therefor.
In Column 7, Line 40 delete "GAIL" and insert -- GAII, --, therefor.
In Column 11, Line 13 delete "(e.g," and insert -- (e.g., --, therefor.
In Column 11, Line 16 delete "(e.g," and insert -- (e.g., --, therefor.
In Column 11, Line 18 delete "(e.g," and insert -- (e.g., --, therefor.
In Column 11, Line 48 delete "al" and insert -- al. --, therefor.
In Column 14, Line 10 delete "(006994)," and insert -- (O06994), --, therefor.
In Column 15, Lines 26-27 delete "cervisiae" and insert -- cerevisiae --, therefor.
In Column 19, Line 5 delete "XL™)" and insert -- XL™). --, therefor.
In Column 19, Line 20 delete "REDO)" and insert -- RED®) --, therefor.
In Column 19, Line 60 delete "REDO)" and insert -- RED®) --, therefor.
In Column 22, Line 4 delete "(e.g." and insert -- (e.g., --, therefor.
In Column 25, Line 12 delete "H2SO4" and insert -- $H_2SO_4$ --, therefor.
In Column 30, Line 62 delete "(OD600)" and insert -- ($OD_{600}$) --, therefor.
In Column 30, Line 66 delete "(OD600)" and insert -- ($OD_{600}$) --, therefor.
In Column 31, Line 9 delete "dilution" and insert -- dilution) --, therefor.
In Column 32, Line 38 delete "ampicillin" and insert -- ampicillin. --, therefor.
In Column 33, Line 23 delete "0.1" and insert -- 0.1. --, therefor.
In Column 33, Line 66 delete "(OD600)" and insert -- ($OD_{600}$) --, therefor.
In Column 34, Line 32 delete "(OD600)" and insert -- ($OD_{600}$) --, therefor.

In the Claims

In Column 121, Claim 3, Line 1 delete "claim," and insert -- claim 1, --, therefor.

Signed and Sealed this
Nineteenth Day of November, 2024

Katherine Kelly Vidal
*Director of the United States Patent and Trademark Office*